United States Patent
Wang (12)

(10) Patent No.: US 10,300,123 B2
(45) Date of Patent: May 28, 2019

(54) SYNTHETIC PEPTIDE-BASED MARKER VACCINE AND DIAGNOSTIC SYSTEM FOR EFFECTIVE CONTROL OF PORCINE REPRODUCTIVE AND RESPIRATORY SYNDROME (PRRS)

(75) Inventor: Chang Yi Wang, Cold Spring Harbor, NY (US)

(73) Assignee: UNITED BIOMEDICAL, INC., Hauppauge, NY (US)

( * ) Notice: Subject to any disclaimer, the term of this patent is extended or adjusted under 35 U.S.C. 154(b) by 0 days.

(21) Appl. No.: 14/370,010

(22) PCT Filed: Dec. 30, 2011

(86) PCT No.: PCT/US2011/068133
§ 371 (c)(1),
(2), (4) Date: Jun. 30, 2014

(87) PCT Pub. No.: WO2013/101195
PCT Pub. Date: Jul. 4, 2013

(65) Prior Publication Data
US 2014/0335118 A1    Nov. 13, 2014

(51) Int. Cl.
*A61K 39/12* (2006.01)
*G01N 33/569* (2006.01)
(Continued)

(52) U.S. Cl.
CPC .............. *A61K 39/12* (2013.01); *C12N 7/00* (2013.01); *G01N 33/56983* (2013.01);
(Continued)

(58) Field of Classification Search
None
See application file for complete search history.

(56) References Cited

U.S. PATENT DOCUMENTS

| 5,498,538 A | 3/1996 | Kay et al. |
| 6,025,468 A | 2/2000 | Wang |

(Continued)

FOREIGN PATENT DOCUMENTS

| CN | 1259141 | 7/2000 |
| CN | 101845083 | 9/2010 |

(Continued)

OTHER PUBLICATIONS

Campbell. Laboratory Techniques in Biochemistry and Molecular Biology. vol. 13, 1984. Elsevier. Monoclonal Antibody Technology. The Production and Characerization of Rodent and Human Hybridomas. p. 1-33.*

(Continued)

*Primary Examiner* — Michelle S Horning
(74) *Attorney, Agent, or Firm* — Locke Lord, LLP; Brandon T. Schurter

(57) ABSTRACT

A peptide-based marker vaccine against Porcine Reproductive and Respiratory Syndrome (PRRS) and a set of immunodiagnostic tests for the prevention, monitoring and control of Porcine Reproductive and Respiratory Syndrome Virus (PRRSV) are disclosed. Vaccine formulations according to various embodiments of the invention contain a mixture of peptides derived from PRRSV GP2, GP3, GP4, or GP5 proteins; each peptide individually contains a B cell PRRSV neutralizing/receptor binding epitope which is individually linked to an artificial T helper epitope for enhancement of the respective peptide's immunogenicity; and which can be supplemented with a mixture of peptides representing the T helper epitopes derived from the PRRSV GP4, GP5, M and Nucleocapsid proteins to provide cell mediated immunity. Such viral peptide compositions are prepared in an acceptable delivery system as vaccine formulations and can pro- (Continued)

vide cross protection of PRRSV antibody free pigs from infection upon PRRSV challenge.

18 Claims, 9 Drawing Sheets

Specification includes a Sequence Listing.

(51) Int. Cl.
    *C12N 7/00*     (2006.01)
    *A61K 39/00*     (2006.01)

(52) U.S. Cl.
    CPC .. *A61K 2039/545* (2013.01); *A61K 2039/552* (2013.01); *A61K 2039/55516* (2013.01); *A61K 2039/55566* (2013.01); *A61K 2039/6031* (2013.01); *A61K 2039/627* (2013.01); *A61K 2039/70* (2013.01); *C12N 2770/10034* (2013.01); *G01N 2333/08* (2013.01)

(56) References Cited

U.S. PATENT DOCUMENTS

| | | |
|---|---|---|
| 6,713,301 B1 | 3/2004 | Wang |
| 2003/0027979 A1 | 2/2003 | Wang |
| 2004/0009897 A1 | 1/2004 | Sokoll |
| 2004/0224327 A1 | 11/2004 | Meulenberg et al. |
| 2008/0008722 A1 | 1/2008 | Chang et al. |
| 2009/0148475 A1 | 6/2009 | Harris et al. |
| 2010/0035276 A1 | 2/2010 | Murtaugh et al. |

FOREIGN PATENT DOCUMENTS

| | | |
|---|---|---|
| JP | 2002-518463 | 6/2002 |
| WO | 1998/050426 | 11/1998 |
| WO | 1999/066952 | 12/1999 |
| WO | 1999/066957 | 12/1999 |

OTHER PUBLICATIONS

GenBank: AF035409 Porcine reproductive and respiratory syndrome virus (Year: 1998).*
Bassaganya-Riera, J, et al. "Impact of immunizations with porcine reproductive and respiratory syndrome virus on lymphoproliferative recall responses of CD8+ T cells." Viral Immunol. 17: 25-37, (2004).
Bautista, E.M, et al. "Cell-mediated immunity to porcine reproductive and respiratory syndrome virus in swine." Viral Immunol. 10: 83-94, (1997).
Chen, C-M. "Effects of PCV2 infection in a transgenic SPF pig farm in Taiwan." 13th AAAP Anim. Sci. Congr. Hanoi, Vietnam. Proceedings, p. 420, Sep. 22-26, 2008.
Das, PB, et al. "The Minor Envelope Glycoproteins GP2a and GP4 of Porcine Reproductive and Respiratory Syndrome Virus Interact with the Receptor CD163." J. Virol. 84:1731-1740, (2010).
Diaz, I, et al. "In silico prediction and ex vivo evaluation of potential T-cell epitopes in glycoproteins 4 and 5 and nucleocapsid protein of genotype-I (European) of porcine reproductive and respiratory syndrome virus." Vaccine 27: 5603-5611, (2009).
Finstad, CL, et al. "Synthetic luteinizing hormone releasing hormone (LHRH) vaccine for effective androgen deprivation and its application to prostate cancer immunotheray." Vaccine 22:1300-1313, (2004).
Fuerst, TR, et al. "Eukaryotic transient-expression system based on recombinant vaccinia virus that synthesizes bacteriophage T7 RNA polymerase." Proc. Natl. Acad. Sci. USA 83:8122-8126, (1986).
Gorbalenya, A, et al. "Nidovirales: evolving the largest RNA virus genome." Virus Res. 117:17-37; DOI: 10.1016/j.virusres.2006.01.017, (2006).
Harlow, E., "Antibodies: a Laboratory Manual." Chapter 14 Immunoassays, pp. 555-612. Cold Spring Harbor Laboratory, Cold Spring Harbor, NY, (1988).
Hseuh, PR, et al. "Highly Specific SARS Antibody Test for Serosurveillance." Emerg. Infect. Diseases, 10:1558-1562, (2004).
Lopez Fuertes, L, et al. "Analysis of cellular immune response in pigs recovered from porcine respiratory and reproductive syndrome infection." Virus Res. 64: 33-42, (1999).
Lopez, OJ, et al. "Role of neutralizing antibodies in PRRSV protective immunity." Vet Immunol Immunopathol 102:155-63, (2004).
Lopez, OJ, et al. "Protection against porcine reproductive and respiratory syndrome virus (PRRSV) infection through passive transfer of Prrsv-neutralizing antibodies is dose dependent." Clin Vaccine Immunol 14:269-75, (2007).
Mateu, E., "The challenge of PRRS immunology." Vet. J. 177 (3), 345-351, (2008).
Tian K., et al. "Emergence of Fatal PRRSV Variants: Unparalleled Outbreaks of Atypical PRRS in China and Molecular Dissection of the Unique Hallmark." PLoS ONE 2(6): e526, (2007).
Uniprotkb. O56258 (O56258_PRRSV). Feb. 11, 2011 (online). Retrieved online Jun. 13, 2012 from http://www.uniprot.org/uniprot/O56258.
Vanhee, M, et al. "Characterization of antigenic regions in the porcine reproductive and respiratory syndrome virus by the use of peptide-specific serum antibodies." Vaccine. 29:4794-4804, (2011).
Wang, CY, et al. "Synthetic Peptide-based Vaccine and Diagnostic System for Effective Control of FMD." Biologicals, 29: 221-228, (2001).
Wang, CY, et al. "Effective Synthetic peptide vaccine for foot-and-mouth disease in swine." Vaccine. 20:2603-2610, (2002).
Wang, CY, et al. "Synthetic AIDS vaccine by targeting HIV receptor." Vaccine, 21: 89-97, (2002).
Wang, CY, et al. "Synthetic IgE peptide vaccine for immunotherapy for allergy." Vaccine, 21:1580-1590, (2003).
Wang, CY, et al. "Site-specific peptide vaccines for immunotherapy and immunization against chronic diseases, cancer, infectious diseases, and for veterinary applications." (Review Article) Vaccine, 23:2049-2056, (2005).
Wang, CY, et. al. "Site Specific UBITh Amyloid-β Vaccine for Immunotherapy of Alzheimer's Disease." Vaccine, 25: 3041-3052, (2007).
Wang, YX, et al. "Identification of immunodominant T-cell epitopes in membrane protein of highly pathogenic porcine reproductive and respiratory syndrome virus." Virus Research, 158(1-2):108-115 doi: 10.1016/j.virusres.2011.03.018, (2011).
International Search Report and Written Opinion of the International Searching Authority, issued in corresponding PCT Application No. PCT/US2011/068133, dated Jun. 29, 2012.
De Lima, M, et al.: "Serologic marker candidates identified among B-cell linear epitopes of Nsp2 and structural proteins of a North American strain of porcine reproductive and respiratory syndrome virus"; Virology, vol. 353, No. 2, p. 410-421 (2006).
De Lima, M, et al.: "Development of a porcine reproductive and respiratory syndrome virus differentiable (DIVA) strain through deletion of specific immunodominant epitopes"; Vaccine, vol. 26, No. 29-30, pp. 3594-3600 (2008).
Faaberg, KS, et al.: "Neutralizing Antibody Responses of Pigs Infected With Natural GP5 N-Glycan Mutants of Porcine Reproductive and Respiratory Syndrome Virus", Viral Immunology, vol. 19, No. 2, pp. 294-304 (2006).
Fang, L, et al.: "Enhanced immunogenicity of the modified GP5 of procine reproductive and respiratory syndrome virus"; Virus Genes, vol. 32, No. 1, pp. 5-11 (2006).
GenBank datebases, NCBI. Accession No. AAD32105, May 25, 1995 [on line], [searched on Oct. 23, 2015], internet, <URL: http://www.ncbi.nlm.nih.gov/protein/AAD32105.1>.
GenBank datebases, NCBI. Accession No. ABL60899, Jul. 18, 2007 [on line], [searched on Oct. 23, 2015], internet, <URL: http://www.ncbi.nlm.nih.gov/protein/ABL60899.1>.
GenBank datebases, NCBI. Accession No. ABL60900, Jul. 18, 2007 [on line], [searched on Oct. 23, 2015], internet, <URL: http://www.ncbi.nlm.nih.gov/protein/ABL60900.1>.

(56) References Cited

OTHER PUBLICATIONS

GenBank datebases, NCBI. Accession No. ABL60901, Jul. 18, 2007 [on line], [searched on Oct. 23, 2015], internet, <URL: http://www.ncbi.nlm.nih.gov/protein/ABL60901.1>.

GenBank datebases, NCBI. Accession No. ABL60902, Jul. 18, 2007 [on line], [searched on Oct. 23, 2015], internet, <URL: http://www.ncbi.nlm.nih.gov/protein/ABL60902.1>.

Pyo, H, et al.: "Serodiagnosis of porcine reproductive and respiratory syndrome virus infection with the use of glycoprotein 5 antigens", Canadian Journal of Veterinary Research=Revue Canadienne De Recherche Veterinaire, pp. 223-227 (2010).

Ostrowski, M, et al.: "Identification of neutralizing and nonneutralizing epitopes in the porcine reproductive and respiratory syndrome virus GP5 ectodomain", Journal of Virology, vol. 76, No. 9, pp. 4241-4250 (2002).

Plagemann, PGW, et al.: "The primary neutralization epitope of porcine respiratory and reproductive syndrome virus strain VR-23332 is located in the middle of the GP5 ectodomain", Archives of Virology, vol. 147, pp. 2327-2347 (2002).

Plagemann, PGW: "The primary GP5 neutralization epitope of North American isolates of porcine reproductive and respiratory syndrome virus", Veterinary Immunology and Immunopathology, vol. 102, No. 3, pp. 263-275 (2004).

Van Woensel, PA, et al.: "Effect on viraemia of an American and a European serotype PRRSV vaccine after challenge with European wild-type strains of the virus" Vet. Rec., vol. 142, No. 19, pp. 510-512 (1998).

Vashisht, K, et al.: "Identification of immunodominant T-cell epitopes present in glycoprotein 5 of the North American genotype of porcine reproductive and respiratory syndrome virus" Vaccine, vol. 26, No. 36, p. 4747-4753 (2008).

Search Report issued in corresponding Taiwanese Application No. 101150920, dated Jun. 5, 2014.

Supplementary European Search Report issued in corresponding European Application No. EP 11878842.1, dated Jul. 10, 2015.

Zheng, Q., et al. "Co-expressing GP5 and M proteins under different promoters in recombinant modified vaccinia virus ankara (rMVA)-based vaccine vector enhanced the humoral and cellular immune responses of porcine reproductive and respiratory syndrome virus (PRRSV)"; Virus Genes, 35(3):585-595 (2007).

Jiang, W., et al. "Recombinant adenovirus expressing GP5 and M fusion proteins of porcine reproductive and respiratory syndrome virus induce both humoral and cell-mediated immune responses in mice"; Veterinary Immunology and Immunopathology, 113(1-2):169-180 (2006).

Chia, M-Y., et al. "Immunogenicity of recombinant GP5 protein of porcine reproductive and respiratory syndrome virus expressed in tobacco plant"; Veterinary Immunology and Immunopathology, 135(3-4):234-242 (2010).

* cited by examiner

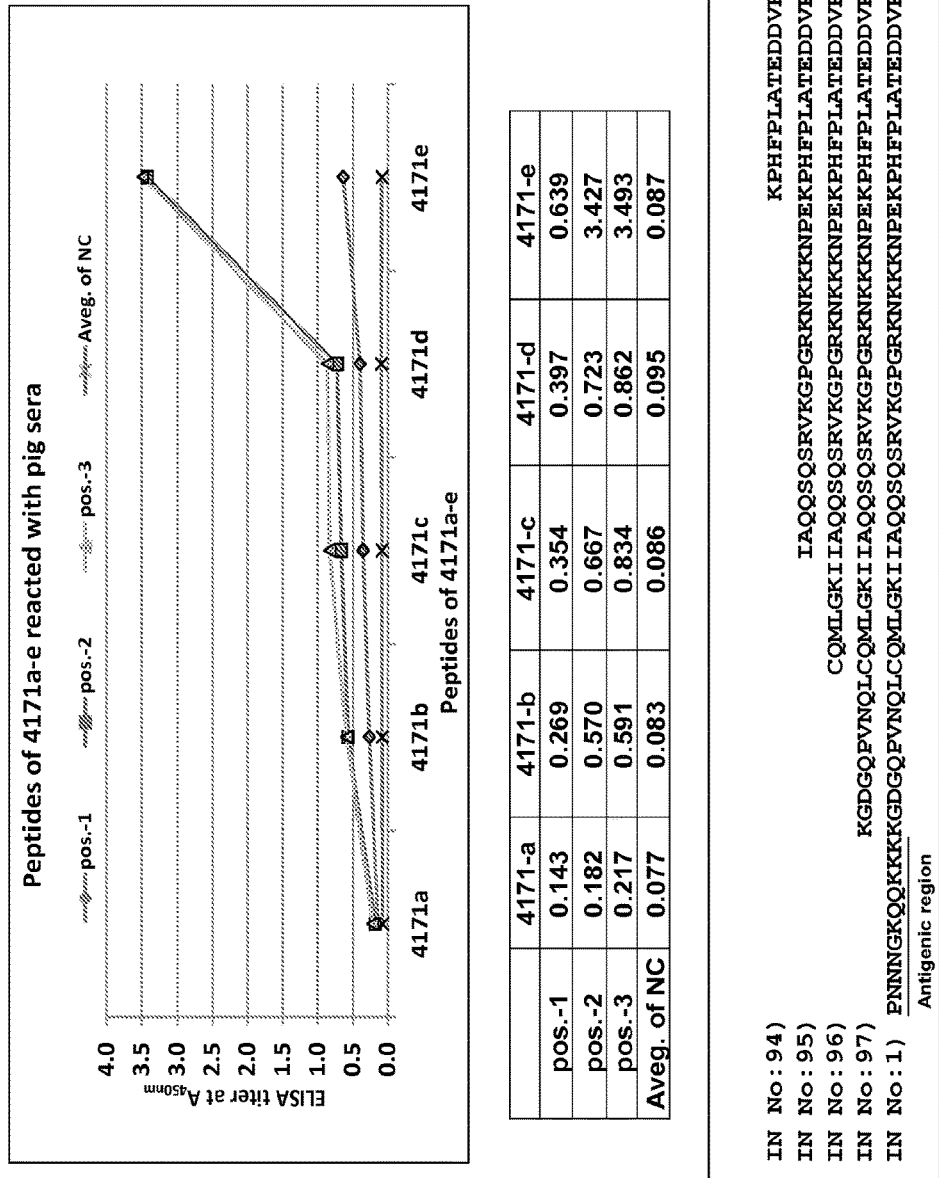

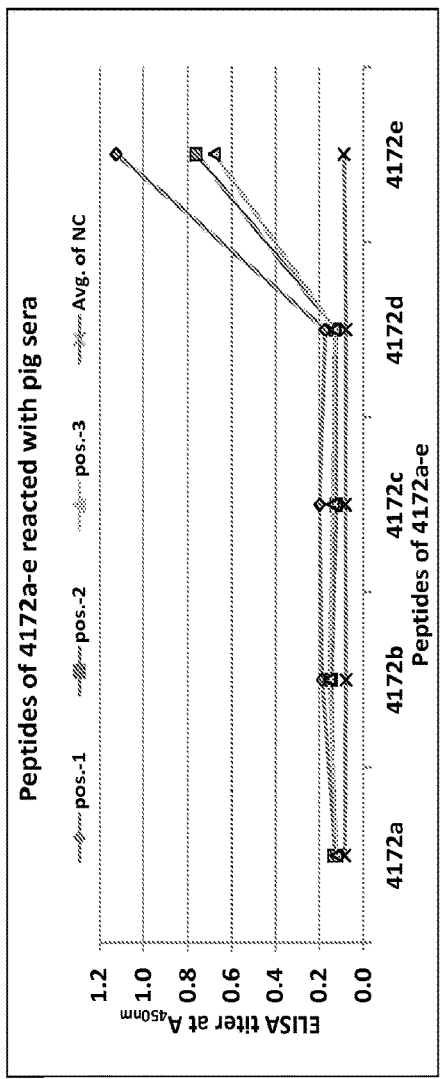

Figure 2B

|  | 4172a | 4172b | 4172c | 4172d | 4172e |
|---|---|---|---|---|---|
| pos.-1 | 0.128 | 0.187 | 0.199 | 0.173 | 1.126 |
| pos.-2 | 0.134 | 0.145 | 0.123 | 0.127 | 0.762 |
| pos.-3 | 0.122 | 0.155 | 0.139 | 0.131 | 0.679 |
| Avg. of NC | 0.084 | 0.078 | 0.082 | 0.079 | 0.088 |

|  |  | ELISA for infected pigs |
|---|---|---|
| (4172a) (SEQ ID No: 98) | VRLIRVTAPPSA | (-) |
| (4172b) (SEQ ID No: 99) | CILSDSGRISYTVEFSLPTHHTVRLIRVTAPPSA | (-) |
| (4172c) (SEQ ID No: 100) | QTAFNQGAGTCILSDSGRISYTVEFSLPTHHTVRLIRVTAPPSA | (-) |
| (4172d) (SEQ ID No: 101) | PSERQLCLSSIQTAFNQGAGTCILSDSGRISYTVEFSLPTHHTVRLIRVTAPPSA | (-) |
| (4172e) (SEQ ID No:2) | <u>EKPHFPLATEDDVRHHFT</u>PSERQLCLSSIQTAFNQGAGTCILSDSGRISYTVEFSLPTHHTVRLIRVTAPPSA | (+) |
|  | Antigenic region |  |

Figure 3

```
MD001  MPNNNGKQQKKKK----GDGQPVNQLCQMLGKIIAQQSQSRVKGPGRKNKKKNPEKPHFP  56
JXA1   MPNNNGKQQKKKK----GNGQPVNQLCQMLGKIIAQQNQSRGKGPGKKNRKKNPEKPHFP  56
NA     MPNNNGKQQKRKK----GDGQPVNQLCQMLGKIIAQQNQSRGKGPGKKNKKKNPEKPHFP  56
EU     MAGRNRSQKKKKNPAPMGNDQPVNQLCQLLGAMMKSRRQ---QPRGGQAKKRKPEKPHFP  57

MD001  LATEDDVRHHFTPSERQLCLSSIQTAFNQGAGTCILSDSGRISYTVEFSLPTHHTVRLIR  116
JXA1   LATEDDVRHHFTPSERQLCLSSIQTAFNQGAGTCALSDSGRISYTVEFSLPTQHTVRLIR  116
NA     LATEDDVRHHFTPSERQLCLSSIQTAFNQGAGTCTLSDSGRISYTVEFSLPTHHTVRLIR  116
EU     LAAEDDVRHHLTQTERSLCLQSIQTAFNQGAGVASLSSSGKVSFQVEFMLPVAHTVRLIR  117

MD001  VTAPPSA-------  123  (SEQ ID No 3)
JXA1   ATASPSA-------  123  (SEQ ID No 4)
NA     VTASPSA-------  123  (SEQ ID No 5)
EU     VTSTSASQDAN---  128  (SEQ ID No 6)
```

Figure 6A

UBI PRRSV Peptide Marker Vaccine Formulations elicit specific high titer antibodies in PRRSV infected pigs in the presence of antibodies to PRRSV NC protein (S/C>2)

PRRSV GP2, GP(2/3) or GP(3/4) based formulations - Sera collected at 0, 4 and 6 wpi after 0 and 4 wpi immunizations

Figure 6B

UBI PRRSV Peptide Marker Vaccine Formulations elicit specific high titer antibodies in PRRSV infected pigs in the presence of antibodies to PRRSV NC protein (S/C>2)

PRRSV GP4, GP(3/4) or GP5 based formulations - Sera collected at 0, 4 and 6 wpi after 0 and 4 wpi immunizations

SEQUENCE LISTING

<160> NUMBER OF SEQ ID NOS: 101

<210> SEQ ID NO 1
<211> LENGTH: 70
<212> TYPE: PRT
<213> ORGANISM: Porcine reproductive and respiratory syndrome virus
<220> FEATURE:
<221> NAME/KEY: PEPTIDE
<222> LOCATION: (1)..(70)
<223> OTHER INFORMATION: PRRSV MD001/TW/AAC98536/nucleocapsid protein
      (P2-E71).

<400> SEQUENCE: 1

Pro Asn Asn Asn Gly Lys Gln Gln Lys Lys Lys Gly Asp Gly Gln
1               5                   10                  15

Pro Val Asn Gln Leu Cys Gln Met Leu Gly Lys Ile Ile Ala Gln Gln
            20                  25                  30

Ser Gln Ser Arg Val Lys Gly Pro Gly Arg Lys Asn Lys Lys Lys Asn
        35                  40                  45

Pro Glu Lys Pro His Phe Pro Leu Ala Thr Glu Asp Val Arg His
    50                  55                  60

His Phe Thr Pro Ser Glu
65                  70

<210> SEQ ID NO 2
<211> LENGTH: 73
<212> TYPE: PRT
<213> ORGANISM: Porcine reproductive and respiratory syndrome virus
<220> FEATURE:
<221> NAME/KEY: PEPTIDE
<222> LOCATION: (1)..(73)
<223> OTHER INFORMATION: PRRSV MD001/TW/AAC98536/nucleocapsid protein
      (E51-A123)

<400> SEQUENCE: 2

Glu Lys Pro His Phe Pro Leu Ala Thr Glu Asp Val Arg His His
1               5                   10                  15

Phe Thr Pro Ser Glu Arg Gln Leu Cys Leu Ser Ser Ile Gln Thr Ala
            20                  25                  30

Phe Asn Gln Gly Ala Gly Thr Cys Ile Leu Ser Asp Ser Gly Arg Ile
        35                  40                  45

Ser Tyr Thr Val Glu Phe Ser Leu Pro Thr His His Thr Val Arg Leu
    50                  55                  60

Ile Arg Val Thr Ala Pro Pro Ser Ala
65                  70

<210> SEQ ID NO 3
<211> LENGTH: 123
<212> TYPE: PRT
<213> ORGANISM: Porcine reproductive and respiratory syndrome virus
<220> FEATURE:
<221> NAME/KEY: PEPTIDE
<222> LOCATION: (1)..(123)
<223> OTHER INFORMATION: PRRSV MD001 isolate/AAC98536/nucleocapsid
      protein (M1-A123)

<400> SEQUENCE: 3

Met Pro Asn Asn Asn Gly Lys Gln Gln Lys Lys Lys Gly Asp Gly
1               5                   10                  15

Gln Pro Val Asn Gln Leu Cys Gln Met Leu Gly Lys Ile Ile Ala Gln
            20                  25                  30

Gln Ser Gln Ser Arg Val Lys Gly Pro Gly Arg Lys Asn Lys Lys Lys
        35                  40                  45

-continued

Asn Pro Glu Lys Pro His Phe Pro Leu Ala Thr Glu Asp Asp Val Arg
            50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Ile Leu Ser Asp Ser Gly
                85                  90                  95

Arg Ile Ser Tyr Thr Val Glu Phe Ser Leu Pro Thr His His Thr Val
             100                 105                 110

Arg Leu Ile Arg Val Thr Ala Pro Pro Ser Ala
         115                 120

<210> SEQ ID NO 4
<211> LENGTH: 123
<212> TYPE: PRT
<213> ORGANISM: Porcine reproductive and respiratory syndrome virus
<220> FEATURE:
<221> NAME/KEY: PEPTIDE
<222> LOCATION: (1)..(123)
<223> OTHER INFORMATION: PRRSV JXA1 isolate/ACN93875/nucleocapsid
      protein (M1-A123).

<400> SEQUENCE: 4

Met Pro Asn Asn Asn Gly Lys Gln Gln Lys Lys Lys Gly Asn Gly
 1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Arg Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Ala Leu Ser Asp Ser Gly
                85                  90                  95

Arg Ile Ser Tyr Thr Val Glu Phe Ser Leu Pro Thr Gln His Thr Val
             100                 105                 110

Arg Leu Ile Arg Ala Thr Ala Ser Pro Ser Ala
         115                 120

<210> SEQ ID NO 5
<211> LENGTH: 123
<212> TYPE: PRT
<213> ORGANISM: Porcine reproductive and respiratory syndrome virus
<220> FEATURE:
<221> NAME/KEY: PEPTIDE
<222> LOCATION: (1)..(123)
<223> OTHER INFORMATION: PRRSV North American strain of VR-2332
      /AAD12131/nucleocapsid protein (M1-A123).

<400> SEQUENCE: 5

Met Pro Asn Asn Asn Gly Lys Gln Gln Lys Arg Lys Lys Gly Asp Gly
 1               5                  10                  15

Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
     50                  55                  60

His His Phe Thr Pro Ser Glu Arg Gln Leu Cys Leu Ser Ser Ile Gln

```
                65                  70                  75                  80
Thr Ala Phe Asn Gln Gly Ala Gly Thr Cys Thr Leu Ser Asp Ser Gly
                    85                  90                  95
Arg Ile Ser Tyr Thr Val Glu Phe Ser Leu Pro Thr His His Thr Val
                100                 105                 110
Arg Leu Ile Arg Val Thr Ala Ser Pro Ser Ala
                115                 120

<210> SEQ ID NO 6
<211> LENGTH: 128
<212> TYPE: PRT
<213> ORGANISM: Porcine reproductive and respiratory syndrome virus
<220> FEATURE:
<221> NAME/KEY: PEPTIDE
<222> LOCATION: (1)..(128)
<223> OTHER INFORMATION: PRRSV EU isolate 08V204/Belgium/GU737266/
      nucleocapsid protein (M1-N128).

<400> SEQUENCE: 6

Met Ala Gly Arg Asn Arg Ser Gln Lys Lys Lys Asn Pro Ala Pro
1               5                   10                  15
Met Gly Asn Asp Gln Pro Val Asn Gln Leu Cys Gln Leu Leu Gly Ala
                20                  25                  30
Met Met Lys Ser Arg Arg Gln Gln Pro Arg Gly Gly Gln Ala Lys Lys
                35                  40                  45
Arg Lys Pro Glu Lys Pro His Phe Pro Leu Ala Ala Glu Asp Asp Val
            50                  55                  60
Arg His His Leu Thr Gln Thr Glu Arg Ser Leu Cys Leu Gln Ser Ile
65                  70                  75                  80
Gln Thr Ala Phe Asn Gln Gly Ala Gly Val Ala Ser Leu Ser Ser Ser
                    85                  90                  95
Gly Lys Val Ser Phe Gln Val Glu Phe Met Leu Pro Val Ala His Thr
                100                 105                 110
Val Arg Leu Ile Arg Val Thr Ser Thr Ser Ala Ser Gln Asp Ala Asn
                115                 120                 125

<210> SEQ ID NO 7
<211> LENGTH: 71
<212> TYPE: PRT
<213> ORGANISM: Porcine reproductive and respiratory syndrome virus
<220> FEATURE:
<221> NAME/KEY: PEPTIDE
<222> LOCATION: (1)..(71)
<223> OTHER INFORMATION: PRRSV European strain/08V204/Belgium/GU737266/
      nucleocapsid protein (A2-E72).

<400> SEQUENCE: 7

Ala Gly Arg Asn Arg Ser Gln Lys Lys Lys Asn Pro Ala Pro Met
1               5                   10                  15
Gly Asn Asp Gln Pro Val Asn Gln Leu Cys Gln Leu Leu Gly Ala Met
                20                  25                  30
Met Lys Ser Arg Arg Gln Gln Pro Arg Gly Gly Gln Ala Lys Lys Arg
                35                  40                  45
Lys Pro Glu Lys Pro His Phe Pro Leu Ala Ala Glu Asp Asp Val Arg
            50                  55                  60
His His Leu Thr Gln Thr Glu
65                  70

<210> SEQ ID NO 8
<211> LENGTH: 78
```

```
<212> TYPE: PRT
<213> ORGANISM: Porcine reproductive and respiratory syndrome virus
<220> FEATURE:
<221> NAME/KEY: PEPTIDE
<222

```
1               5                   10                  15

Phe Trp Cys

<210> SEQ ID NO 12
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: PRRSV JXA1 isolate/ACN93872/envelope protein
      GP4 (C52-C69).

<400> SEQUENCE: 12

Cys Leu Arg His Gly Asp Ser Ser Ser Pro Thr Ile Arg Lys Ser Ser
1               5                   10                  15

Gln Cys

<210> SEQ ID NO 13
<211> LENGTH: 34
<212> TYPE: PRT
<213> ORGANISM: Porcine reproductive and respiratory syndrome virus
<220> FEATURE:
<221> NAME/KEY: PEPTIDE
<222> LOCATION: (1)..(34)
<223> OTHER INFORMATION: PRRSV JXA1/ACN93873/envelope protein GP5
      (V21-D54).

<400> SEQUENCE: 13

Val Pro Phe Tyr Leu Ala Val Leu Val Asn Ala Ser Asn Asn Asn Ser
1               5                   10                  15

Ser His Ile Gln Leu Ile Tyr Asn Leu Thr Leu Cys Glu Leu Asn Gly
            20                  25                  30

Thr Asp

<210> SEQ ID NO 14
<211> LENGTH: 34
<212> TYPE: PRT
<213> ORGANISM: Porcine reproductive and respiratory syndrome virus
<220> FEATURE:
<221> NAME/KEY: PEPTIDE
<222> LOCATION: (1)..(34)
<223> OTHER INFORMATION: PRRSV North American VR-2332/AAD12129/envelope
      protein GP5 (V21-D54).

<400> SEQUENCE: 14

Val Pro Phe Cys Phe Ala Val Leu Ala Asn Ala Ser Asn Asp Ser Ser
1               5                   10                  15

Ser His Leu Gln Leu Ile Tyr Asn Leu Thr Leu Cys Glu Leu Asn Gly
            20                  25                  30

Thr Asp

<210> SEQ ID NO 15
<211> LENGTH: 36
<212> TYPE: PRT
<213> ORGANISM: Porcine reproductive and respiratory syndrome virus
<220> FEATURE:
<221> NAME/KEY: PEPTIDE
<222> LOCATION: (1)..(36)
<223> OTHER INFORMATION: PRRSV EU isolate 08V204/Belgium/GU737266/
      envelope protein GP5 (F21-T56).

<400> SEQUENCE: 15

Phe Ser Leu Cys Ile Gly Leu Ser Trp Ser Phe Ala Asp Gly Asn Gly
1               5                   10                  15
```

Asn Ser Ser Thr Tyr Gln Tyr Ile Tyr Asn Leu Thr Ile Cys Glu Leu
            20                  25                  30

Asn Gly Thr Thr
        35

<210> SEQ ID NO 16
<211> LENGTH: 36
<212> TYPE: PRT
<213> ORGANISM: Porcine reproductive and respiratory syndrome virus
<220> FEATURE:
<221> NAME/KEY: PEPTIDE
<222> LOCATION: (1)..(36)
<223> OTHER INFORMATION: Consensus sequence from PRRSV MD001, JXA1,
      VR-2332 and EU 08V204/ envelope protein GP5 (V21-D54).

<400> SEQUENCE: 16

Val Pro Phe Cys Leu Ala Val Leu Val Ser Ala Ser Asp Gly Asn Asn
1               5                   10                  15

Asn Ser Ser His Ile Gln Leu Ile Tyr Asn Leu Thr Leu Cys Glu Leu
            20                  25                  30

Asn Gly Thr Asp
        35

<210> SEQ ID NO 17
<211> LENGTH: 26
<212> TYPE: PRT
<213> ORGANISM: Porcine reproductive and respiratory syndrome virus
<220> FEATURE:
<221> NAME/KEY: PEPTIDE
<222> LOCATION: (1)..(26)
<223> OTHER INFORMATION: PRRSV MD001 isolate/AAC98531/envelope protein
      GP2 (V111-L136).

<400> SEQUENCE: 17

Val Ser Arg Arg Met Tyr Arg Ile Met Glu Lys Ala Gly Gln Ala Ala
1               5                   10                  15

Trp Lys Gln Val Val Asn Glu Ala Thr Leu
            20                  25

<210> SEQ ID NO 18
<211> LENGTH: 26
<212> TYPE: PRT
<213> ORGANISM: Porcine reproductive and respiratory syndrome virus
<220> FEATURE:
<221> NAME/KEY: PEPTIDE
<222> LOCATION: (1)..(26)
<223> OTHER INFORMATION: PRRSV North American VR-2332 /AAD12126/envelope
      protein GP2 (V111-L136)

<400> SEQUENCE: 18

Val Ser Arg Arg Met Tyr Arg Ile Met Glu Lys Ala Gly Gln Ala Ala
1               5                   10                  15

Trp Lys Gln Val Val Ser Glu Ala Thr Leu
            20                  25

<210> SEQ ID NO 19
<211> LENGTH: 26
<212> TYPE: PRT
<213> ORGANISM: Porcine reproductive and respiratory syndrome virus
<220> FEATURE:
<221> NAME/KEY: PEPTIDE
<222> LOCATION: (1)..(26)
<223> OTHER INFORMATION: PRRSV EU isolate 08V204/Belgium/GU737266/
      envelope protein GP2 (V111-L136).

<400> SEQUENCE: 19

Val Ser Arg Arg Ile Tyr Gln Thr Met Glu His Ser Gly Gln Ala Ala
1               5                   10                  15

Trp Lys Gln Val Val Ser Glu Ala Thr Leu
            20                  25

<210> SEQ ID NO 20
<211> LENGTH: 26
<212> TYPE: PRT
<213> ORGANISM: Porcine reproductive and respiratory syndrome virus
<220> FEATURE:
<221> NAME/KEY: PEPTIDE
<222> LOCATION: (1)..(26)
<223> OTHER INFORMATION: Consensus sequence from PRRSV MD001, JXA1,
      VR-2332 and EU 08V204 envelope protein of GP2 (V11-L136).

<400> SEQUENCE: 20

Val Ser Arg Arg Met Tyr Arg Ile Met Glu Lys Ala Gly Gln Ala Ala
1               5                   10                  15

Trp Lys Gln Val Val Ser Glu Ala Thr Leu
            20                  25

<210> SEQ ID NO 21
<211> LENGTH: 19
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: PRRSV MD001/AAC98532/envelope protein GP3
      (C57-C75).

<400> SEQUENCE: 21

Cys Leu Thr Arg Gln Ala Ala Ala Gln Leu Tyr Glu Pro Ser Arg Ser
1               5                   10                  15

Leu Trp Cys

<210> SEQ ID NO 22
<211> LENGTH: 19
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: PRRSV North American VR-2332 /AAD12127/envelope
      protein GP3 (C57-C75).

<400> SEQUENCE: 22

Cys Leu Thr Arg Gln Ala Ala Thr Glu Ile Tyr Glu Pro Gly Arg Ser
1               5                   10                  15

Leu Trp Cys

<210> SEQ ID NO 23
<211> LENGTH: 19
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: PRRSV EU isolate 08V204/Belgium/GU737266/
      envelope protein GP3 (C57-C75).

<400> SEQUENCE: 23

Cys Leu Thr Ser Gln Ala Ala Lys Gln Arg Leu Glu Pro Gly Arg Asn
1               5                   10                  15

Met Trp Cys

<210> SEQ ID NO 24
<211> LENGTH: 19
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Consensus sequence from PRRSV MD001, JXA1,
      VR-2332 and EU 08V204 envelope protein of GP3 (C57-C75).

<400> SEQUENCE: 24

Cys Leu Thr Arg Gln Ala Ala Ala Glu Ile Leu Glu Pro Gly Arg Ser
1               5                   10                  15

Leu Trp Cys

<210> SEQ ID NO 25
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: PRRSV MD001 isolate/AAC98533/envelope protein
      GP4 (C52-C69).

<400> SEQUENCE: 25

Cys Leu Arg His Gly Asn Pro Ser Ser Glu Ala Ile Arg Lys Ile Pro
1               5                   10                  15

Gln Cys

<210> SEQ ID NO 26
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: PRRSV North American VR-2332 /AAD12128/envelope
      protein GP4 (C52-C69).

<400> SEQUENCE: 26

Cys Leu Arg His Arg Asp Ser Ala Ser Glu Ala Ile Arg Lys Ile Pro
1               5                   10                  15

Gln Cys

<210> SEQ ID NO 27
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: PRRSV EU isolate 08V204/Belgium/GU737266/
      envelope protein GP4 (C52-C69).

<400> SEQUENCE: 27

Cys Leu Arg Pro Tyr Arg Thr Asn Thr Thr Gln Gly Lys Val Pro Ser
1               5                   10                  15

Gln Cys

<210> SEQ ID NO 28
<211> LENGTH: 18
<212> TYPE: PRT
<213> ORGANISM: Porcine reproductive and respiratory syndrome virus
<220> FEATURE:

```
<221> NAME/KEY: PEPTIDE
<222> LOCATION: (1)..(18)
<223> OTHER INFORMATION: Consensus sequence from PRRSV MD001, JXA1,
      VR-2332 and EU 08V204 envelope protein of GP4 (C52-C69).

<400> SEQUENCE: 28

Cys Leu Arg Pro Gly Asp Ser Ser Ser Glu Ala Ile Arg Lys Ile Ser
1               5                   10                  15

Gln Cys

<210> SEQ ID NO 29
<211> LENGTH: 40
<212> TYPE: PRT
<213> ORGANISM: Porcine reproductive and respiratory syndrome virus
<220> FEATURE:
<221> NAME/KEY: PEPTIDE
<222> LOCATION: (1)..(40)
<223> OTHER INFORMATION: PRRSV MD001 isolate/AAC98534/envelope protein
      GP5 (A26-E65).

<400> SEQUENCE: 29

Ala Ala Leu Val Ser Ala Asn Gly Asn Ser Ser His Ser Gln Leu
1               5                   10                  15

Ile Tyr Asn Leu Thr Leu Cys Glu Leu Asn Gly Thr Asp Trp Leu Ala
            20                  25                  30

Lys Lys Phe Asp Trp Ala Val Glu
        35                  40

<210> SEQ ID NO 30
<211> LENGTH: 45
<212> TYPE: PRT
<213> ORGANISM: Porcine reproductive and respiratory syndrome virus
<220> FEATURE:
<221> NAME/KEY: PEPTIDE
<222> LOCATION: (1)..(45)
<223> OTHER INFORMATION: PRRSV MD001 isolate/AAC98534/envelope protein
      GP5 (V21-E65)

<400> SEQUENCE: 30

Val Pro Phe Cys Leu Ala Ala Leu Val Ser Ala Asn Gly Asn Ser Ser
1               5                   10                  15

Ser His Ser Gln Leu Ile Tyr Asn Leu Thr Leu Cys Glu Leu Asn Gly
            20                  25                  30

Thr Asp Trp Leu Ala Lys Lys Phe Asp Trp Ala Val Glu
            35                  40                  45

<210> SEQ ID NO 31
<211> LENGTH: 34
<212> TYPE: PRT
<213> ORGANISM: Porcine reproductive and respiratory syndrome virus
<220> FEATURE:
<221> NAME/KEY: PEPTIDE
<222> LOCATION: (1)..(34)
<223> OTHER INFORMATION: PRRSV JXA1isolate/AAC98534/envelope protein GP5
      (V21-D54).

<400> SEQUENCE: 31

Val Pro Phe Cys Leu Ala Val Leu Val Asn Ala Ser Asn Asn Asn Ser
1               5                   10                  15

Ser His Ile Gln Leu Ile Tyr Asn Leu Thr Leu Cys Glu Leu Asn Gly
            20                  25                  30

Thr Asp

<210> SEQ ID NO 32
```

```
<211> LENGTH: 34
<212> TYPE: PRT
<213> ORGANISM: Porcine reproductive and respiratory syndrome virus
<220> FEATURE:
<221> NAME/KEY: PEPTIDE
<222

```
<222> LOCATION: (13)..(13)
<223> OTHER INFORMATION: N or G
<220> FEATURE:
<221> NAME/KEY: MISC_FEATURE
<222> LOCATION: (14)..(14)
<223> OTHER INFORMATION: N or D
<220> FEATURE:
<221> NAME/KEY: MISC_FEATURE
<222> LOCATION: (15)..(15)
<223> OTHER INFORMATION: N or S
<220> FEATURE:
<221> NAME/KEY: MISC_FEATURE
<222> LOCATION: (18)..(18)
<223> OTHER INFORMATION: H or Y
<220> FEATURE:
<221> NAME/KEY: MISC_FEATURE
<222> LOCATION: (19)..(19)
<223> OTHER INFORMATION: I or L or S

<400> SEQUENCE: 33

Val Pro Phe Cys Xaa Ala Xaa Leu Xaa Xaa Ala Xaa Xaa Xaa Xaa Ser
1               5                   10                  15

Ser Xaa Xaa Gln Leu Ile Tyr Asn Leu Thr Leu Cys Glu Leu Asn Gly
            20                  25                  30

Thr Asp

<210> SEQ ID NO 34
<211> LENGTH: 25
<212> TYPE: PRT
<213> ORGANISM: Porcine reproductive and respiratory syndrome virus
<220> FEATURE:
<221> NAME/KEY: PEPTIDE
<222> LOCATION: (1)..(25)
<223> OTHER INFORMATION: Combinatorial sequence from PRRSV
      NJ-a/AY737282, JXA1/ACN93873 and MD001/AAC98534 of envelope
      protein GP5 (C24-C48).
<220> FEATURE:
<221> NAME/KEY: MISC_FEATURE
<222> LOCATION: (2)..(2)
<223> OTHER INFORMATION: F or L
<220> FEATURE:
<221> NAME/KEY: MISC_FEATURE
<222> LOCATION: (4)..(4)
<223> OTHER INFORMATION: A or V
<220> FEATURE:
<221> NAME/KEY: MISC_FEATURE
<222> LOCATION: (6)..(6)
<223> OTHER INFORMATION: A or V
<220> FEATURE:
<221> NAME/KEY: MISC_FEATURE
<222> LOCATION: (7)..(7)
<223> OTHER INFORMATION: N or S
<220> FEATURE:
<221> NAME/KEY: MISC_FEATURE
<222> LOCATION: (9)..(9)
<223> OTHER INFORMATION: S or N
<220> FEATURE:
<221> NAME/KEY: MISC_FEATURE
<222> LOCATION: (10)..(10)
<223> OTHER INFORMATION: N or G
<220> FEATURE:
<221> NAME/KEY: MISC_FEATURE
<222> LOCATION: (11)..(11)
<223> OTHER INFORMATION: D or N
<220> FEATURE:
<221> NAME/KEY: MISC_FEATURE
<222> LOCATION: (12)..(12)
<223> OTHER INFORMATION: S or N
<220> FEATURE:
<221> NAME/KEY: MISC_FEATURE
<222> LOCATION: (15)..(15)
<223> OTHER INFORMATION: H or Y
<220> FEATURE:
<221> NAME/KEY: MISC_FEATURE
<222> LOCATION: (16)..(16)
```

```
<223> OTHER INFORMATION: L or I or S

<400> SEQUENCE: 34

Cys Xaa Ala Xaa Leu Xaa Xaa Ala Xaa Xaa Xaa Xaa Ser Ser Xaa Xaa
1               5                   10                  15

Gln Leu Ile Tyr Asn Leu Thr Leu Cys
            20                  25

<210> SEQ ID NO 35
<211> LENGTH: 19
<212> TYPE: PRT
<213> ORGANISM: Measles virus
<220> FEATURE:
<221> NAME/KEY: PEPTIDE
<222> LOCATION: (1)..(19)
<223> OTHER INFORMATION: Combinatorial modified T helper peptide.
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R

<400> SEQUENCE: 35

Ile Ser Ile Xaa Glu Ile Xaa Xaa Val Ile Val Xaa Xaa Ile Glu Thr
1               5                   10                  15

Ile Leu Phe

<210> SEQ ID NO 36
<211> LENGTH: 4
<212> TYPE: PRT
<213> ORGANISM: Artificial Sequence
<220> FEATURE:
<223> OTHER INFORMATION: xxxxxxxx
<220> FEATURE:
<221> NAME/KEY: PEPTIDE
<222> LOCATION: (1)..(4)
<223> OTHER INFORMATION: Artificial linked spacer sequence.

<400> SEQUENCE: 36

Lys Lys Lys Lys
1

<210> SEQ ID NO 37
<211> LENGTH: 63
<212> TYPE: PRT
<213> ORGANISM: Porcine reproductive and respiratory syndrome virus
<220> FEATURE:
<221> NAME/KEY: PEPTIDE
<222> LOCATION: (1)..(40)
<223> OTHER INFORMATION: PRRSV MD001/AAC98534 of evelope protein GP5
      (A26-E65).
<220> FEATURE:
<221> NAME/KEY: PEPTIDE
<222> LOCATION: (41)..(44)
<223> OTHER INFORMATION: linked specer, K (41) is epsilon K.
<220> FEATURE:
```

<221> NAME/KEY: PEPTIDE
<222> LOCATION: (45)..(63)
<223> OTHER INFORMATION: Artificial combinatorial T helper sequence (modified T helper site).
<220> FEATURE:
<221> NAME/KEY: MISC_FEATURE
<222> LOCATION: (48)..(48)
<223> OTHER INFORMATION: S or T
<220> FEATURE:
<221> NAME/KEY: MISC_FEATURE
<222> LOCATION: (51)..(51)
<223> OTHER INFORMATION: K or R
<220> FEATURE:
<221> NAME/KEY: MISC_FEATURE
<222> LOCATION: (52)..(52)
<223> OTHER INFORMATION: G or T
<220> FEATURE:
<221> NAME/KEY: MISC_FEATURE
<222> LOCATION: (56)..(56)
<223> OTHER INFORMATION: H or T
<220> FEATURE:
<221> NAME/KEY: MISC_FEATURE
<222> LOCATION: (57)..(57)
<223> OTHER INFORMATION: K or R

<400> SEQUENCE: 37

```
Ala Ala Leu Val Ser Ala Asn Gly Asn Ser Ser Ser His Ser Gln Leu
1               5                   10                  15

Ile Tyr Asn Leu Thr Leu Cys Glu Leu Asn Gly Thr Asp Trp Leu Ala
            20                  25                  30

Lys Lys Phe Asp Trp Ala Val Glu Lys Lys Lys Lys Ile Ser Ile Xaa
        35                  40                  45

Glu Ile Xaa Xaa Val Ile Val Xaa Xaa Ile Glu Thr Ile Leu Phe
    50                  55                  60
```

<210> SEQ ID NO 38
<211> LENGTH: 68
<212> TYPE: PRT
<213> ORGANISM: Porcine reproductive and respiratory syndrome virus
<220> FEATURE:
<221> NAME/KEY: PEPTIDE
<222> LOCATION: (1)..(45)
<223> OTHER INFORMATION: PRRSV MD001/AAC98534 of envelope protein GP5 (V21-E65).
<220> FEATURE:
<221> NAME/KEY: PEPTIDE
<222> LOCATION: (46)..(49)
<223> OTHER INFORMATION: linked spacer; K (46) is epsilon K.
<220> FEATURE:
<221> NAME/KEY: PEPTIDE
<222> LOCATION: (50)..(68)
<223> OTHER INFORMATION: Artificial combinatorial T helper sequence (modified T helper site).
<220> FEATURE:
<221> NAME/KEY: MISC_FEATURE
<222> LOCATION: (53)..(53)
<223> OTHER INFORMATION: S or T
<220> FEATURE:
<221> NAME/KEY: MISC_FEATURE
<222> LOCATION: (56)..(56)
<223> OTHER INFORMATION: K or R
<220> FEATURE:
<221> NAME/KEY: MISC_FEATURE
<222> LOCATION: (57)..(57)
<223> OTHER INFORMATION: G or T
<220> FEATURE:
<221> NAME/KEY: MISC_FEATURE
<222> LOCATION: (61)..(61)
<223> OTHER INFORMATION: H or T
<220> FEATURE:
<221> NAME/KEY: MISC_FEATURE
<222> LOCATION: (62)..(62)
<223> OTHER INFORMATION: K or R

```
<400> SEQUENCE: 38

Val Pro Phe Cys Leu Ala Ala Leu Val Ser Ala Asn Gly Asn Ser Ser
1               5                   10                  15

Ser His Ser Gln Leu Ile Tyr Asn Leu Thr Leu Cys Glu Leu Asn Gly
                20                  25                  30

Thr Asp Trp Leu Ala Lys Lys Phe Asp Trp Ala Val Glu Lys Lys Lys
            35                  40                  45

Lys Ile Ser Ile Xaa Glu Ile Xaa Xaa Val Ile Val Xaa Xaa Ile Glu
50                  55                  60

Thr Ile Leu Phe
65

<210> SEQ ID NO 39
<211> LENGTH: 57
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Artificial combinatorial T helper sequence
      (modified T helper site).
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: Linked spacer, K (23) is epsilon K.
<220> FEATURE:
<221> NAME/KEY: PEPTIDE
<222> LOCATION: (24)..(57)
<223> OTHER INFORMATION: PRRSV MD001/AF121131 of envelope protein GP5
      (V21-D54).

<400> SEQUENCE: 39

Ile Ser Ile Xaa Glu Ile Xaa Xaa Val Ile Val Xaa Xaa Ile Glu Thr
1               5                   10                  15

Ile Leu Phe Lys Lys Lys Lys Val Pro Phe Cys Leu Ala Ala Leu Val
                20                  25                  30

Ser Ala Asn Gly Asn Ser Ser Tyr Ser Gln Leu Ile Tyr Asn Leu
            35                  40                  45

Thr Leu Cys Glu Leu Asn Gly Thr Asp
50                  55

<210> SEQ ID NO 40
<211> LENGTH: 57
<212> TYPE: PRT
<213> ORGANISM: Porcine reproductive and respiratory syndrome virus
<220> FEATURE:
<221> NAME/KEY: PEPTIDE
<222> LOCATION: (1)..(19)
```

```
<223> OTHER INFORMATION: Artificial combinatorial T helper sequence
      (modified T helper site).
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: linked spacer, K (23) is epsilon K.
<220> FEATURE:
<221> NAME/KEY: PEPTIDE
<222> LOCATION: (24)..(57)
<223> OTHER INFORMATION: PRRSV JXA1/EF112445 of envelope protein GP5
      (V21-D54);

<400> SEQUENCE: 40

Ile Ser Ile Xa

```
<223> OTHER INFORMATION: Combinatorial sequence from GP5 (V21-D54) of
      PRRSV JXA1/EF112445 and MD001/AF121131.
<220> FEATURE:
<221> NAME/KEY: MISC_FEATURE
<222> LOCATION: (30)..(30)
<223> OTHER INFORMATION: V or A
<220> FEATURE:
<221> NAME/KEY: MISC_FEATURE
<222> LOCATION: (33)..(33)
<223> OTHER INFORMATION: N or S
<220> FEATURE:
<221> NAME/KEY: MISC_FEATURE
<222> LOCATION: (35)..(35)
<223> OTHER INFORMATION: S or N
<220> FEATURE:
<221> NAME/KEY: MISC_FEATURE
<222> LOCATION: (36)..(36)
<223> OTHER INFORMATION: N or G
<220> FEATURE:
<221> NAME/KEY: MISC_FEATURE
<222> LOCATION: (38)..(38)
<223> OTHER INFORMATION: N or S
<220> FEATURE:
<221> NAME/KEY: MISC_FEATURE
<222> LOCATION: (41)..(41)
<223> OTHER INFORMATION: H or Y
<220> FEATURE:
<221> NAME/KEY: MISC_FEATURE
<222> LOCATION: (42)..(42)
<223> OTHER INFORMATION: I or S

<400> SEQUENCE: 41

Ile Ser Ile Xaa Glu Ile Xaa Xaa Val Ile Val Xaa Xaa Ile Glu Thr
1               5                   10                  15

Ile Leu Phe Lys Lys Lys Lys Val Pro Phe Cys Leu Ala Xaa Leu Val
            20                  25                  30

Xaa Ala Xaa Xaa Asn Xaa Ser Ser Xaa Xaa Gln Leu Ile Tyr Asn Leu
        35                  40                  45

Thr Leu Cys Glu Leu Asn Gly Thr Asp
    50                  55

<210> SEQ ID NO 42
<211> LENGTH: 57
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Artificial combinatorial T helper sequence
      (modified T helper site).
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: linked spacer, K (23) is episilon K.
```

```
<220> FEATURE:
<221> NAME/KEY: PEPTIDE
<222> LOCATION: (24)..(57)
<223> OTHER INFORMATION: Combinatorial sequence from envelope protein
      GP5 (V21-D54 ) of PRRSV JXA1/EF112445 and NJ-a/AY737282.
<220> FEATURE:
<221> NAME/KEY: MISC_FEATURE
<222> LOCATION: (28)..(28)
<223> OTHER INFORMATION: L or F
<220> FEATURE:
<221> NAME/KEY: MISC_FEATURE
<222> LOCATION: (30)..(30)
<223> OTHER INFORMATION: V or A
<220> FEATURE:
<221> NAME/KEY: MISC_FEATURE
<222> LOCATION: (32)..(32)
<223> OTHER INFORMATION: V or A
<220> FEATURE:
<221> NAME/KEY: MISC_FEATURE
<222> LOCATION: (33)..(33)
<223> OTHER INFORMATION: N or S
<220> FEATURE:
<221> NAME/KEY: MISC_FEATURE
<222> LOCATION: (35)..(35)
<223> OTHER INFORMATION: S or N
<220> FEATURE:
<221> NAME/KEY: MISC_FEATURE
<222> LOCATION: (36)..(36)
<223> OTHER INFORMATION: N or G
<220> FEATURE:
<221> NAME/KEY: MISC_FEATURE
<222> LOCATION: (37)..(37)
<223> OTHER INFORMATION: N or D
<220> FEATURE:
<221> NAME/KEY: MISC_FEATURE
<222> LOCATION: (38)..(38)
<223> OTHER INFORMATION: N or S
<220> FEATURE:
<221> NAME/KEY: MISC_FEATURE
<222> LOCATION: (41)..(41)
<223> OTHER INFORMATION: H or Y
<220> FEATURE:
<221> NAME/KEY: MISC_FEATURE
<222> LOCATION: (42)..(42)
<223> OTHER INFORMATION: I or L or S

<400> SEQUENCE: 42

Ile Ser Ile Xaa Glu Ile Xaa Xaa Val Ile Val Xaa Xaa Ile Glu Thr
1               5                   10                  15

Ile Leu Phe Lys Lys Lys Lys Val Pro Phe Cys Xaa Ala Xaa Leu Xaa
            20                  25                  30

Xaa Ala Xaa Xaa Xaa Xaa Ser Ser Xaa Xaa Gln Leu Ile Tyr Asn Leu
        35                  40                  45

Thr Leu Cys Glu Leu Asn Gly Thr Asp
    50                  55

<210> SEQ ID NO 43
<211> LENGTH: 48
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Artificial combinatorial T helper sequence
      (modified T helper site).
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
```

```
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: PEPTIDE
<222> LOCATION: (20)..(23)
<223> OTHER INFORMATION: Linked spacer, K (23) is epsilon K.
<220> FEATURE:
<221> NAME/KEY: PEPTIDE
<222> LOCATION: (24)..(48)
<223> OTHER INFORMATION: Combinatorial sequence from envelope protein
      GP5 (C24-C48) of PRRSV NJ-a/AY737282, JXA1/EF112445 and MD001/
      AF121131.
<220> FEATURE:
<221> NAME/KEY: MISC_FEATURE
<222> LOCATION: (25)..(25)
<223> OTHER INFORMATION: F or L
<220> FEATURE:
<221> NAME/KEY: MISC_FEATURE
<222> LOCATION: (27)..(27)
<223> OTHER INFORMATION: A or V
<220> FEATURE:
<221> NAME/KEY: MISC_FEATURE
<222> LOCATION: (29)..(29)
<223> OTHER INFORMATION: A or V
<220> FEATURE:
<221> NAME/KEY: MISC_FEATURE
<222> LOCATION: (30)..(30)
<223> OTHER INFORMATION: N or S
<220> FEATURE:
<221> NAME/KEY: MISC_FEATURE
<222> LOCATION: (32)..(32)
<223> OTHER INFORMATION: S or N
<220> FEATURE:
<221> NAME/KEY: MISC_FEATURE
<222> LOCATION: (33)..(33)
<223> OTHER INFORMATION: N or G
<220> FEATURE:
<221> NAME/KEY: MISC_FEATURE
<222> LOCATION: (34)..(34)
<223> OTHER INFORMATION: D or N
<220> FEATURE:
<221> NAME/KEY: MISC_FEATURE
<222> LOCATION: (35)..(35)
<223> OTHER INFORMATION: S or N
<220> FEATURE:
<221> NAME/KEY: MISC_FEATURE
<222> LOCATION: (38)..(38)
<223> OTHER INFORMATION: H or Y
<220> FEATURE:
<221> NAME/KEY: MISC_FEATURE
<222> LOCATION: (39)..(39)
<223> OTHER INFORMATION: L or I or S

<400> SEQUENCE: 43

Ile Ser Ile Xaa Glu Ile Xaa Xaa Val Ile Val Xaa Xaa Ile Glu Thr
1               5                   10                  15

Ile Leu Phe Lys Lys Lys Lys Cys Xaa Ala Xaa Leu Xaa Xaa Ala Xaa
            20                  25                  30

Xaa Xaa Xaa Ser Ser Xaa Xaa Gln Leu Ile Tyr Asn Leu Thr Leu Cys
            35                  40                  45

<210> SEQ ID NO 44
<211> LENGTH: 46
<212> TYPE: PRT
<213> ORGANISM: Porcine reproductive and respiratory syndrome virus
<220> FEATURE:
```

```
<221> NAME/KEY: PEPTIDE
<222> LOCATION: (1)..(19)
<223> OTHER INFORMATION: Artificial combinatorial T helper sequence
      (modified T helper site).
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: PEPTIDE
<222> LOCATION: (20)..(20)
<223> OTHER INFORMATION: Linked spacer, K (20) is epsilon K.
<220> FEATURE:
<221> NAME/KEY: PEPTIDE
<222> LOCATION: (21)..(46)
<223> OTHER INFORMATION: PRRSV JXA1 isolate/ACN93870/envelope protein
      GP2 (V111-L136)

<400> SEQUENCE: 44

Ile Ser Ile Xaa Glu Ile Xaa Xaa Val Ile Val Xaa Xaa Ile Glu Thr
1               5                   10                  15

Ile Leu Phe Lys Val Ser Arg Arg Met Tyr Arg Ile Met Glu Lys Ala
            20                  25                  30

Gly Gln Ala Ala Trp Lys Gln Val Val Ser Glu Ala Thr Leu
        35                  40                  45

<210> SEQ ID NO 45
<211> LENGTH: 39
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Artificial combinatorial T helper sequence
      (modified T helper site).
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: PEPTIDE
<222> LOCATION: (20)..(20)
<223> OTHER INFORMATION: Linker spacer, K (20) is epsilon K.
```

```
<220> FEATURE:
<221> NAME/KEY: PEPTIDE
<222> LOCATION: (21)..(39)
<223> OTHER INFORMATION: PRRSV JXA1/ACN93871 of GP3 (C57-C75).

<400> SEQUENCE: 45

Ile Ser Ile Xaa Glu Ile Xaa Xaa Val Ile Val Xaa Xaa Ile Glu Thr
1               5                   10                  15

Ile Leu Phe Lys Cys Pro Thr Arg Gln Ala Ala Ala Glu Ile Leu Glu
            20                  25                  30

Pro Gly Lys Ser Phe Trp Cys
            35

<210> SEQ ID NO 46
<211> LENGTH: 38
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Artificial combinatorial T helper sequence
      (modified T helper site).
<220> FEATURE:
<221> NAME/KEY: MISC_FEATURE
<222> LOCATION: (4)..(4)
<223> OTHER INFORMATION: S or T
<220> FEATURE:
<221> NAME/KEY: MISC_FEATURE
<222> LOCATION: (7)..(7)
<223> OTHER INFORMATION: K or R
<220> FEATURE:
<221> NAME/KEY: MISC_FEATURE
<222> LOCATION: (8)..(8)
<223> OTHER INFORMATION: G or T
<220> FEATURE:
<221> NAME/KEY: MISC_FEATURE
<222> LOCATION: (12)..(12)
<223> OTHER INFORMATION: H or T
<220> FEATURE:
<221> NAME/KEY: MISC_FEATURE
<222> LOCATION: (13)..(13)
<223> OTHER INFORMATION: K or R
<220> FEATURE:
<221> NAME/KEY: PEPTIDE
<222> LOCATION: (20)..(20)
<223> OTHER INFORMATION: Linked spacer, K (20) is epsilon K.
<220> FEATURE:
<221> NAME/KEY: PEPTIDE
<222> LOCATION: (21)..(38)
<223> OTHER INFORMATION: PRRSV JXA1/ACN93872 of GP4 (C52-C69).

<400> SEQUENCE: 46

Ile Ser Ile Xaa Glu Ile Xaa Xaa Val Ile Val Xaa Xaa Ile Glu Thr
1               5                   10                  15

Ile Leu Phe Lys Cys Leu Arg His Gly Asp Ser Ser Ser Pro Thr Ile
            20                  25                  30

Arg Lys Ser Ser Gln Cys
            35

<210> SEQ ID NO 47
<211> LENGTH: 9
<212> TYPE: PRT
<213> ORGANISM: Porcine reproductive and respiratory syndrome virus
<220> FEATURE:
<221> NAME/KEY: PEPTIDE
<222> LOCATION: (1)..(9)
<223> OTHER INFORMATION: GP4 (F7-L15) of PRRSV JXA1/ACN93872.

<400> SEQUENCE: 47

Phe Leu Leu Val Gly Phe Lys Cys Phe
```

```
1               5
```

<210> SEQ ID NO 48
<211> LENGTH: 9
<212> TYPE: PRT
<213> ORGANISM: Porcine reproductive and respiratory syndrome virus
<220> FEATURE:
<221> NAME/KEY: PEPTIDE
<222> LOCATION: (1)..(9)
<223> OTHER INFORMATION: GP4 (F7-L15) of PRRSV MD001/AAC98533.

<400> SEQUENCE: 48

```
Phe Leu Leu Val Gly Phe Lys Cys Leu
1               5
```

<210> SEQ ID NO 49
<211> LENGTH: 9
<212> TYPE: PRT
<213> ORGANISM: Porcine reproductive and respiratory syndrome virus
<220> FEATURE:
<221> NAME/KEY: PEPTIDE
<222> LOCATION: (1)..(9)
<223> OTHER INFORMATION: GP4 (F7-L15) of PRRSV North American strain
      VR-2332/AAD12128.

<400> SEQUENCE: 49

```
Phe Leu Val Val Gly Phe Lys Cys Leu
1               5
```

<210> SEQ ID NO 50
<211> LENGTH: 9
<212> TYPE: PRT
<213> ORGANISM: Porcine reproductive and respiratory syndrome virus
<220> FEATURE:
<221> NAME/KEY: PEPTIDE
<222> LOCATION: (1)..(9)
<223> OTHER INFORMATION: GP4 (F7-L15) of PRRSV EU isolate 08V204/
      Belgium/GU737266.

<400> SEQUENCE: 50

```
Phe Leu Leu Ala Gly Ala Gln His Leu
1               5
```

<210> SEQ ID NO 51
<211> LENGTH: 9
<212> TYPE: PRT
<213> ORGANISM: Porcine reproductive and respiratory syndrome virus
<220> FEATURE:
<221> NAME/KEY: PEPTIDE
<222> LOCATION: (1)..(9)
<223> OTHER INFORMATION: From GP4 (C170-I178) of PRRSVJXA1/ACN93872,
      MD001/AAC98533, VR-2332 /AAD12128 and EU isolate 08V204/Belgium/
      GU737266.

<400> SEQUENCE: 51

```
Cys Leu Phe Ala Ile Leu Leu Ala Ile
1               5
```

<210> SEQ ID NO 52
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: From GP5 (L117-C131) of PRRSV JXA1/ACN93873 and
      MD001/AAC98534.

<400> SEQUENCE: 52

Leu Ala Ala Leu Ile Cys Phe Val Ile Arg Leu Ala Lys Asn Cys
1               5                   10                  15

<210> SEQ ID NO 53
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: GP5 (L117-C131) of PRRSV North American
      VR-2332/AAD12129.

<400> SEQUENCE: 53

Leu Ala Ala Leu Thr Cys Phe Val Ile Arg Phe Ala Lys Asn Cys
1               5                   10                  15

<210> SEQ ID NO 54
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: GP5 (F119-C133) of PRRSV EU isolate 08V204/
      Belgium/GU737266.

<400> SEQUENCE: 54

Phe Ala Ala Phe Val Cys Phe Ala Ile Arg Ala Thr Lys Asn Cys
1               5                   10                  15

<210> SEQ ID NO 55
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: GP5 (K149-K163) of PRRSV JXA1 isolate/ACN93873.

<400> SEQUENCE: 55

Lys Gly Arg Leu Tyr Arg Trp Arg Ser Pro Val Ile Val Glu Lys
1               5                   10                  15

<210> SEQ ID NO 56
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: GP5 (K149-K163) of PRRSV MD001 isolate/
      AAC98534.

<400> SEQUENCE: 56

Lys Gly Arg Ile Tyr Arg Trp Arg Ser Pro Val Ile Ile Glu Lys
1               5                   10                  15

<210> SEQ ID NO 57
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: GP5 (K149-K163) of PRRSV North American
      VR-2332/AAD12129.

<400> SEQUENCE: 57

Lys Gly Arg Leu Tyr Arg Trp Arg Ser Pro Val Ile Ile Glu Lys
1               5                   10                  15

<210> SEQ ID NO 58
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: GP5 (R151-K165) of RPRRSV EU isolate 08V204/
      Belgium/GU737266.

<400> SEQUENCE: 58

Arg Gly Arg Ile His Arg Trp Lys Ser Pro Ile Val Ile Glu Lys
1               5                   10                  15

<210> SEQ ID NO 59
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: From M protein (C9-S23) of PRRSV JXA1/ACN93874,
      MD001/AAC98535 and VR-2332/AAD12130.

<400> SEQUENCE: 59

Cys Asn Asp Ser Thr Ala Pro Gln Lys Val Leu Leu Ala Phe Ser
1               5                   10                  15

<210> SEQ ID NO 60
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: M protein (C8-S22) of PRRSV EU isolate 08V204/
      Belgium/GU737266.

<400> SEQUENCE: 60

Cys His Asp Pro Thr Ala Ala Gln Lys Leu Val Leu Ala Phe Ser
1               5                   10                  15

<210> SEQ ID NO 61
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: From M protein (A33-L47) of PRRSV JXA1/
      ACN93874/, MD001/AAC98535 and VR-2332/AAD12130.

<400> SEQUENCE: 61

Ala Leu Lys Val Ser Arg Gly Arg Leu Leu Gly Leu Leu His Leu
1               5                   10                  15

<210> SEQ ID NO 62
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: PRRSV EU isolate 08V204/Belgium/GU737266/M
      protein (A32-I46)

<400> SEQUENCE: 62

```
Ala Leu Lys Val Ser Arg Gly Arg Leu Leu Gly Leu Leu His Ile
1               5                   10                  15

<210> SEQ ID NO 63
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: M protein (F57-V71) of PRRSV JXA1 isolate/
      ACN93874.

<400> SEQUENCE: 63

Phe Gly Tyr Met Thr Phe Val His Phe Glu Ser Thr Asn Arg Val
1               5                   10                  15

<210> SEQ ID NO 64
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: M protein (F57-V71) of PRRSV MD001/AAC98535.

<400> SEQUENCE: 64

Phe Gly Tyr Met Thr Phe Thr His Phe Gln Ser Thr Asn Arg Val
1               5                   10                  15

<210> SEQ ID NO 65
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: M protein (F57-V71) of PRRSV VR-2332/AAD12130.

<400> SEQUENCE: 65

Phe Gly Tyr Met Thr Phe Ala His Phe Gln Ser Thr Asn Lys Val
1               5                   10                  15

<210> SEQ ID NO 66
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: M protein (F56-V70) of PRRSV EU isolate
      08V204/Belgium/GU737266.

<400> SEQUENCE: 66

Phe Gly Tyr Met Thr Tyr Val His Phe Glu Ser Thr Asn Arg Val
1               5                   10                  15

<210> SEQ ID NO 67
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: From M protein (K93-K107) of PRRSV
      JXA1/ACN93874 and VR-2332 /AAD12130.

<400> SEQUENCE: 67
```

```
Lys Phe Ile Thr Ser Arg Cys Arg Leu Cys Leu Leu Gly Arg Lys
1               5                   10                  15

<210> SEQ ID NO 68
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: M protein (R93-K107) of PRRSV MD001/AAC98534.

<400> SEQUENCE: 68

Arg Phe Ile Thr Ser Arg Cys Arg Leu Cys Leu Leu Gly Arg Lys
1               5                   10                  15

<210> SEQ ID NO 69
<211> LENGTH: 15
<212> TYPE: PRT
<213> ORGANISM: Porcine reproductive and respiratory syndrome virus
<220> FEATURE:
<221> NAME/KEY: PEPTIDE
<222> LOCATION: (1)..(15)
<223> OTHER INFORMATION: M protein (K92-R106) of PRRSV EU 08V204/
      Belgium/GU737266.

<400> SEQUENCE: 69

Lys Phe Val Thr Ser Arg Cys Arg Leu Cys Cys Leu Gly Arg Arg
1               5                   10                  15

<210> SEQ ID NO 70
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: Nucleocapsid protein (G40-L57) of PRRSV JXA1
      isolate/ACN93875.

<400> SEQUENCE: 70

Gly Pro Gly Lys Lys Asn Arg Lys Lys Asn Pro Glu Lys Pro His Phe
1               5                   10                  15

Pro Leu

<210> SEQ ID NO 71
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: Nucleocapsid protein (G40-L57) of PRRSV MD001/
      AAC98536.

<400> SEQUENCE: 71

Gly Pro Gly Arg Lys Asn Lys Lys Lys Asn Pro Glu Lys Pro His Phe
1               5                   10                  15

Pro Leu

<210> SEQ ID NO 72
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: Nucleocapsid protein (G40-L57) of PRRSV VR-2332
```

-continued isolate/AAD12131.

<400> SEQUENCE: 72

Gly Pro Gly Lys Lys Asn Lys Lys Asn Pro Glu Lys Pro His Phe
1               5                   10                  15

Pro Leu

<210> SEQ ID NO 73
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: Nucleocapsid protein (P41-L58) of PRRSV EU
      isolate 08V204/Belgium/GU737266.

<400> SEQUENCE: 73

Pro Arg Gly Gly Gln Ala Lys Lys Arg Lys Pro Glu Lys Pro His Phe
1               5                   10                  15

Pro Leu

<210> SEQ ID NO 74
<211> LENGTH: 9
<212> TYPE: PRT
<213> ORGANISM: Porcine reproductive and respiratory syndrome virus
<220> FEATURE:
<221> NAME/KEY: PEPTIDE
<222> LOCATION: (1)..(9)
<223> OTHER INFORMATION: From nucleocapsid protein (V63-E71) of PRRSV
      JXA1/ACN93875, MD001/AAC98536 and VR-2332 /AAD12131.

<400> SEQUENCE: 74

Val Arg His His Phe Thr Pro Ser Glu
1               5

<210> SEQ ID NO 75
<211> LENGTH: 9
<212> TYPE: PRT
<213> ORGANISM: Porcine reproductive and respiratory syndrome virus
<220> FEATURE:
<221> NAME/KEY: PEPTIDE
<222> LOCATION: (1)..(9)
<223> OTHER INFORMATION: Nucleocapsid protein (V64-E72) of PRRSV EU
      08V204/Belgium/GU737266

<400> SEQUENCE: 75

Val Arg His His Leu Thr Gln Thr Glu
1               5

<210> SEQ ID NO 76
<211> LENGTH: 19
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Nucleocapsid protein (S105-A123)of PRRSV
      JXA1/ACN93875.

<400> SEQUENCE: 76

Ser Leu Pro Thr Gln His Thr Val Arg Leu Ile Arg Ala Thr Ala Ser
1               5                   10                  15

Pro Ser Ala

<210> SEQ ID NO 77

```
<211> LENGTH: 19
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Nucleocapsid protein (S105-A123) of PRRSV
      MD001/AAC98536.

<400> SEQUENCE: 77

Ser Leu Pro Thr His His Thr Val Arg Leu Ile Arg Val Thr Ala Pro
1               5                   10                  15

Pro Ser Ala

<210> SEQ ID NO 78
<211> LENGTH: 19
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Nucleocapsid protein (S105-A123) of PRRSV
      VR-2332 isolate/AAD12131.

<400> SEQUENCE: 78

Ser Leu Pro Thr His His Thr Val Arg Leu Ile Arg Val Thr Ala Ser
1               5                   10                  15

Pro Ser Ala

<210> SEQ ID NO 79
<211> LENGTH: 19
<212> TYPE: PRT
<213> ORGANISM: Porcine reproductive and respiratory syndrome virus
<220> FEATURE:
<221> NAME/KEY: PEPTIDE
<222> LOCATION: (1)..(19)
<223> OTHER INFORMATION: Nucleocapsid protein (M106-S124) of PRRSV
      EU isolate 08V204/Belgium/GU737266.

<400> SEQUENCE: 79

Met Leu Pro Val Ala His Thr Val Arg Leu Ile Arg Val Thr Ser Thr
1               5                   10                  15

Ser Ala Ser

<210> SEQ ID NO 80
<211> LENGTH: 12
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: linked spacer
<220> FEATURE:
<221> NAME/KEY: PEPTIDE
<222> LOCATION: (4)..(12)
<223> OTHER INFORMATION: GP4 (F7-L15) of PRRSV MD001/AAC98533.
<220> FEATURE:
<221> NAME/KEY: MISC_FEATURE
<222> LOCATION: (5)..(5)
<223> OTHER INFORMATION: L or I
<220> FEATURE:
<221> NAME/KEY: MISC_FEATURE
<222> LOCATION: (6)..(6)
<223> OTHER INFORMATION: L or V
<220> FEATURE:
<221> NAME/KEY: MISC_FEATURE
<222> LOCATION: (10)..(10)
<223> OTHER INFORMATION: K or R
<220> FEATURE:
<221> NAME/KEY: MISC_FEATURE
```

```
<222> LOCATION: (12)..(12)
<223> OTHER INFORMATION: L or I

<400> SEQUENCE: 80

Lys Lys Lys Phe Xaa Xaa Val Gly Phe Xaa Cys Xaa
1               5                   10

<210> SEQ ID NO 81
<211> LENGTH: 12
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(12)
<223> OTHER INFORMATION: GP4 (C170-I178) of PRRSV MD001/AAC98533.
<220> FEATURE:
<221> NAME/KEY: MISC_FEATURE
<222> LOCATION: (5)..(5)
<223> OTHER INFORMATION: L or I
<220> FEATURE:
<221> NAME/KEY: MISC_FEATURE
<222> LOCATION: (7)..(7)
<223> OTHER INFORMATION: A or L
<220> FEATURE:
<221> NAME/KEY: MISC_FEATURE
<222> LOCATION: (9)..(9)
<223> OTHER INFORMATION: L or I
<220> FEATURE:
<221> NAME/KEY: MISC_FEATURE
<222> LOCATION: (10)..(10)
<223> OTHER INFORMATION: L or I
<220> FEATURE:
<221> NAME/KEY: MISC_FEATURE
<222> LOCATION: (12)..(12)
<223> OTHER INFORMATION: I or L

<400> SEQUENCE: 81

Lys Lys Lys Cys Xaa Phe Xaa Ile Xaa Xaa Ala Xaa
1               5                   10

<210> SEQ ID NO 82
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(18)
<223> OTHER INFORMATION: GP5 (L117-C131) of PRRSV JXA1/ACN93873.
<220> FEATURE:
<221> NAME/KEY: MISC_FEATURE
<222> LOCATION: (4)..(4)
<223> OTHER INFORMATION: L or I
<220> FEATURE:
<221> NAME/KEY: MISC_FEATURE
<222> LOCATION: (7)..(7)
<223> OTHER INFORMATION: L or I
<220> FEATURE:
<221> NAME/KEY: MISC_FEATURE
<222> LOCATION: (8)..(8)
<223> OTHER INFORMATION: I or L
<220> FEATURE:
<221> NAME/KEY: MISC_FEATURE
<222> LOCATION: (13)..(13)
<223> OTHER INFORMATION: R or K
<220> FEATURE:
<221> NAME/KEY: MISC_FEATURE
<222> LOCATION: (14)..(14)
```

<223> OTHER INFORMATION: L or I
<220> FEATURE:
<221> NAME/KEY: MISC_FEATURE
<222> LOCATION: (16)..(16)
<223> OTHER INFORMATION: K or R

<400> SEQUENCE: 82

Lys Lys Lys Xaa Ala Ala Xaa Xaa Cys Phe Val Ile Xaa Xaa Ala Xaa
1               5                   10                  15

Asn Cys

<210> SEQ ID NO 83
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(18)
<223> OTHER INFORMATION: GP5 (K149-K163) of PRRSV MD001/AAC98534.
<220> FEATURE:
<221> NAME/KEY: MISC_FEATURE
<222> LOCATION: (4)..(4)
<223> OTHER INFORMATION: K or R
<220> FEATURE:
<221> NAME/KEY: MISC_FEATURE
<222> LOCATION: (6)..(6)
<223> OTHER INFORMATION: R or K
<220> FEATURE:
<221> NAME/KEY: MISC_FEATURE
<222> LOCATION: (7)..(7)
<223> OTHER INFORMATION: I or L
<220> FEATURE:
<221> NAME/KEY: MISC_FEATURE
<222> LOCATION: (9)..(9)
<223> OTHER INFORMATION: R or K
<220> FEATURE:
<221> NAME/KEY: MISC_FEATURE
<222> LOCATION: (11)..(11)
<223> OTHER INFORMATION: R or K
<220> FEATURE:
<221> NAME/KEY: MISC_FEATURE
<222> LOCATION: (15)..(15)
<223> OTHER INFORMATION: I or L
<220> FEATURE:
<221> NAME/KEY: MISC_FEATURE
<222> LOCATION: (16)..(16)
<223> OTHER INFORMATION: I or L
<220> FEATURE:
<221> NAME/KEY: MISC_FEATURE
<222> LOCATION: (18)..(18)
<223> OTHER INFORMATION: K or R

<400> SEQUENCE: 83

Lys Lys Lys Xaa Gly Xaa Xaa Tyr Xaa Trp Xaa Ser Pro Val Xaa Xaa
1               5                   10                  15

Glu Xaa

<210> SEQ ID NO 84
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(18)
<223> OTHER INFORMATION: Consensus M protein (C9-S23) from PRRSV JXA1/

```
ACN93874, MD001/AAC98535 and other 42 North American genotypes.
<220> FEATURE:
<221> NAME/KEY: MISC_FEATURE
<222> LOCATION: (5)..(5)
<223> OTHER INFORMATION: N or H or Y
<220> FEATURE:
<221> NAME/KEY: MISC_FEATURE
<222> LOCATION: (11)..(11)
<223> OTHER INFORMATION: Q or F or E
<220> FEATURE:
<221> NAME/KEY: MISC_FEATURE
<222> LOCATION: (14)..(14)
<223> OTHER INFORMATION: L or I

<400> SEQUENCE: 84

Lys Lys Lys Cys Xaa Asp Ser Thr Ala Pro Xaa Lys Val Xaa Leu Ala
1               5                   10                  15

Phe Ser

<210> SEQ ID NO 85
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: linked spacer.
<220> FEATURE:
<221> NAME/KEY: PEPTIDE
<222> LOCATION: (4)..(18)
<223> OTHER INFORMATION: Consensus M protein (A33-L47) from PRRSV JXA1/
      ACN93874, MD001/AAC98535 and other 42 North American genotypes.

<400> SEQUENCE: 85

Lys Lys Lys Ala Leu Lys Val Ser Arg Gly Arg Leu Leu Gly Leu Leu
1               5                   10                  15

His Leu

<210> SEQ ID NO 86
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(18)
<223> OTHER INFORMATION: Consensus M protein (F57-V71) of PRRSV JXA1/
      ACN93874 and MD001/AAC98535 and other 42 North American genotypes.
<220> FEATURE:
<221> NAME/KEY: MISC_FEATURE
<222> LOCATION: (9)..(9)
<223> OTHER INFORMATION: F or C
<220> FEATURE:
<221> NAME/KEY: MISC_FEATURE
<222> LOCATION: (10)..(10)
<223> OTHER INFORMATION: V or A or T or F or M
<220> FEATURE:
<221> NAME/KEY: MISC_FEATURE
<222> LOCATION: (12)..(12)
<223> OTHER INFORMATION: F or L
<220> FEATURE:
<221> NAME/KEY: MISC_FEATURE
<222> LOCATION: (13)..(13)
<223> OTHER INFORMATION: E or Q or N
<220> FEATURE:
<221> NAME/KEY: MISC_FEATURE
<222> LOCATION: (17)..(17)
<223> OTHER INFORMATION: R or K

<400> SEQUENCE: 86
```

-continued

Lys Lys Lys Phe Gly Tyr Met Thr Xaa Xaa His Xaa Xaa Ser Thr Asn
1               5                   10                  15

Xaa Val

<210> SEQ ID NO 87
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(18)
<223> OTHER INFORMATION: Consensus M protein (K93-K107) from JXA1
      isolate/ACN93874, MD001 strain/AAC98535 and other 42 other NA
      genotypes.
<220> FEATURE:
<221> NAME/KEY: MISC_FEATURE
<222> LOCATION: (4)..(4)
<223> OTHER INFORMATION: K or R
<220> FEATURE:
<221> NAME/KEY: MISC_FEATURE
<222> LOCATION: (18)..(18)
<223> OTHER INFORMATION: K or R

<400> SEQUENCE: 87

Lys Lys Lys Xaa Phe Ile Thr Ser Arg Cys Arg Leu Cys Leu Leu Gly
1               5                   10                  15

Arg Xaa

<210> SEQ ID NO 88
<211> LENGTH: 21
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(21)
<223> OTHER INFORMATION: Nucleocapsid protein (G40-L57) of PRRSV MD001/
      AF121131 and nucleocapsid protein (P41-L58) of Lena/EU909691.
<220> FEATURE:
<221> NAME/KEY: MISC_FEATURE
<222> LOCATION: (4)..(4)
<223> OTHER INFORMATION: G or P
<220> FEATURE:
<221> NAME/KEY: MISC_FEATURE
<222> LOCATION: (7)..(7)
<223> OTHER INFORMATION: R or G
<220> FEATURE:
<221> NAME/KEY: MISC_FEATURE
<222> LOCATION: (8)..(8)
<223> OTHER INFORMATION: K or Q
<220> FEATURE:
<221> NAME/KEY: MISC_FEATURE
<222> LOCATION: (9)..(9)
<223> OTHER INFORMATION: N or A
<220> FEATURE:
<221> NAME/KEY: MISC_FEATURE
<222> LOCATION: (13)..(13)
<223> OTHER INFORMATION: N or K

<400> SEQUENCE: 88

Lys Lys Lys Xaa Pro Gly Xaa Xaa Xaa Lys Lys Lys Xaa Pro Glu Lys
1               5                   10                  15

Pro His Phe Pro Leu
            20

```
<210> SEQ ID NO 89
<211> LENGTH: 12
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(12)
<223> OTHER INFORMATION: Nucleocapsid protein (V63-E71) of PRRSV
      Europe/EU880437 and nucleocapsid protein (V64-E72) of Lena/
      EU909691.
<220> FEATURE:
<221> NAME/KEY: MISC_FEATURE
<222> LOCATION: (8)..(8)
<223> OTHER INFORMATION: F or L
<220> FEATURE:
<221> NAME/KEY: MISC_FEATURE
<222> LOCATION: (10)..(10)
<223> OTHER INFORMATION: F or L
<220> FEATURE:
<221> NAME/KEY: MISC_FEATURE
<222> LOCATION: (11)..(11)
<223> OTHER INFORMATION: S or T

<400> SEQUENCE: 89

Lys Lys Lys Val Arg His His Xaa Thr Xaa Xaa Glu
1               5                   10

<210> SEQ ID NO 90
<211> LENGTH: 22
<212> TYPE: PRT
<213> ORGANISM: Porcine reproductive and respiratory syndrome virus
<220> FEATURE:
<221> NAME/KEY: PEPTIDE
<222> LOCATION: (1)..(3)
<223> OTHER INFORMATION: Linked spacer.
<220> FEATURE:
<221> NAME/KEY: PEPTIDE
<222> LOCATION: (4)..(22)
<223> OTHER INFORMATION: Nucleocapsid protein (S105-A123) of PRRSV
      MD001/AF121131 and nucleocapsid protein (N106-A124) of Lena/
      EU909691.
<220> FEATURE:
<221> NAME/KEY: MISC_FEATURE
<222> LOCATION: (4)..(4)
<223> OTHER INFORMATION: S or N
<220> FEATURE:
<221> NAME/KEY: MISC_FEATURE
<222> LOCATION: (7)..(7)
<223> OTHER INFORMATION: T or V
<220> FEATURE:
<221> NAME/KEY: MISC_FEATURE
<222> LOCATION: (18)..(18)
<223> OTHER INFORMATION: A or S
<220> FEATURE:
<221> NAME/KEY: MISC_FEATURE
<222> LOCATION: (19)..(19)
<223> OTHER INFORMATION: P or T
<220> FEATURE:
<221> NAME/KEY: MISC_FEATURE
<222> LOCATION: (21)..(21)
<223> OTHER INFORMATION: S or A

<400> SEQUENCE: 90

Lys Lys Lys Xaa Leu Pro Xaa His His Thr Val Arg Leu Ile Arg Val
1               5                   10                  15

Thr Xaa Xaa Pro Xaa Ala
            20
```

-continued

```
<210> SEQ ID NO 91
<211> LENGTH: 11
<212> TYPE: PRT
<213> ORGANISM: Porcine reproductive and respiratory syndrome virus
<220> FEATURE:
<221> NAME/KEY: PEPTIDE
<222> LOCATION: (1)..(11)
<223> OTHER INFORMATION: Nucleocapsid protein (P2-K12) of PRRSV MD001/
      AAC98536 and nucleocapsid protein (P2-K12) of PRRSV JXA1/ACN93875.

<400> SEQUENCE: 91

Pro Asn Asn Asn Gly Lys Gln Gln Lys Lys Lys
1               5                   10

<210> SEQ ID NO 92
<211> LENGTH: 18
<212> TYPE: PRT
<213> ORGANISM: Porcine reproductive and respiratory syndrome virus
<220> FEATURE:
<221> NAME/KEY: PEPTIDE
<222> LOCATION: (1)..(18)
<223> OTHER INFORMATION: Nucleocapsid protein (E51-T68) of PRRSV MD001/
      AAC98536, nucleocapsid protein (E51-T68) of PRRSV JXA1/ACN93875
      and nucleocapsid protein (E51-T68) of PRRSV VR-2332 /AAD12131.

<400> SEQUENCE: 92

Glu Lys Pro His Phe Pro Leu Ala Thr Glu Asp Asp Val Arg His His
1               5                   10                  15

Phe Thr

<210> SEQ ID NO 93
<211> LENGTH: 26
<212> TYPE: PRT
<213> ORGANISM: Porcine reproductive and respiratory syndrome virus
<220> FEATURE:
<221> NAME/KEY: PEPTIDE
<222> LOCATION: (1)..(26)
<223> OTHER INFORMATION: M protein (M1-Y26) of PRRSV MD001/AAC98535.

<400> SEQUENCE: 93

Met Gly Ser Ser Leu Asp Asp Arg Cys His Asp Ser Thr Ala Pro Gln
1               5                   10                  15

Lys Val Leu Leu Ala Phe Ser Ile Thr Tyr
            20                  25

<210> SEQ ID NO 94
<211> LENGTH: 20
<212> TYPE: PRT
<213> ORGANISM: Porcine reproductive and respiratory syndrome virus
<220> FEATURE:
<221> NAME/KEY: PEPTIDE
<222> LOCATION: (1)..(20)
<223> OTHER INFORMATION: Nucleocapsid protein (K52-E71) of PRRSV MD001/
      AAC98536.

<400> SEQUENCE: 94

Lys Pro His Phe Pro Leu Ala Thr Glu Asp Asp Val Arg His His Phe
1               5                   10                  15

Thr Pro Ser Glu
            20

<210> SEQ ID NO 95
<211> LENGTH: 42
<212> TYPE: PRT
<213> ORGANISM: Porcine reproductive and respiratory syndrome virus
<220> FEATURE:
<221> NAME/KEY: PEPTIDE
<222> LOCATION: (1)..(42)
```

-continued

```
<223> OTHER INFORMATION: Nucleocapsid protein (I30-E71) of PRRSV MD001/
      AAC98536.

<400> SEQUENCE: 95

Ile Ala Gln Gln Ser Gln Ser Arg Val Lys Gly Pro Gly Arg Lys Asn
1               5                   10                  15

Lys Lys Lys Asn Pro Glu Lys Pro His Phe Pro Leu Ala Thr Glu Asp
            20                  25                  30

Asp Val Arg His His Phe Thr Pro Ser Glu
        35                  40

<210> SEQ ID NO 96
<211> LENGTH: 49
<212> TYPE: PRT
<213> ORGANISM: Porcine reproductive and respiratory syndrome virus
<220> FEATURE:
<221> NAME/KEY: PEPTIDE
<222> LOCATION: (1)..(49)
<223> OTHER INFORMATION: Nucleocapsid protein (C23-E71) of PRRSV MD001/
      TW/AAC98536.

<400> SEQUENCE: 96

Cys Gln Met Leu Gly Lys Ile Ile Ala Gln Gln Ser Gln Ser Arg Val
1               5                   10                  15

Lys Gly Pro Gly Arg Lys Asn Lys Lys Asn Pro Glu Lys Pro His
            20                  25                  30

Phe Pro Leu Ala Thr Glu Asp Asp Val Arg His His Phe Thr Pro Ser
        35                  40                  45

Glu

<210> SEQ ID NO 97
<211> LENGTH: 59
<212> TYPE: PRT
<213> ORGANISM: Porcine reproductive and respiratory syndrome virus
<220> FEATURE:
<221> NAME/KEY: PEPTIDE
<222> LOCATION: (1)..(59)
<223> OTHER INFORMATION: Nucleocapsid protein (K13-E71) of PRRSV MD001/
      AAC98536.

<400> SEQUENCE: 97

Lys Gly Asp Gly Gln Pro Val Asn Gln Leu Cys Gln Met Leu Gly Lys
1               5                   10                  15

Ile Ile Ala Gln Gln Ser Gln Ser Arg Val Lys Gly Pro Gly Arg Lys
            20                  25                  30

Asn Lys Lys Lys Asn Pro Glu Lys Pro His Phe Pro Leu Ala Thr Glu
        35                  40                  45

Asp Asp Val Arg His His Phe Thr Pro Ser Glu
    50                  55

<210> SEQ ID NO 98
<211> LENGTH: 12
<212> TYPE: PRT
<213> ORGANISM: Porcine reproductive and respiratory syndrome virus
<220> FEATURE:
<221> NAME/KEY: PEPTIDE
<222> LOCATION: (1)..(12)
<223> OTHER INFORMATION: Nucleocapsid protein (V112-A123) of PRRSV
      MD001/TW/AAC98536.

<400> SEQUENCE: 98

Val Arg Leu Ile Arg Val Thr Ala Pro Pro Ser Ala
1               5                   10
```

```
<210> SEQ ID NO 99
<211> LENGTH: 34
<212> TYPE: PRT
<213> ORGANISM: Porcine reproductive and respiratory syndrome virus
<220> FEATURE:
<221> NAME/KEY: PEPTIDE
<222> LOCATION: (1)..(34)
<223> OTHER INFORMATION: Nucleocapsid protein (C90-A123) of PRRSV MD001/
      AAC98536.

<400> SEQUENCE: 99

Cys Ile Leu Ser Asp Ser Gly Arg Ile Ser Tyr Thr Val Glu Phe Ser
1               5                   10                  15

Leu Pro Thr His His Thr Val Arg Leu Ile Arg Val Thr Ala Pro Pro
            20                  25                  30

Ser Ala

<210> SEQ ID NO 100
<211> LENGTH: 44
<212> TYPE: PRT
<213> ORGANISM: Porcine reproductive and respiratory syndrome virus
<220> FEATURE:
<221> NAME/KEY: PEPTIDE
<222> LOCATION: (1)..(44)
<223> OTHER INFORMATION: Nucleocapsid protein (Q80-A123) of PRRSV MD001/
      AAC98536.

<400> SEQUENCE: 100

Gln Thr Ala Phe Asn Gln Gly Ala Gly Thr Cys Ile Leu Ser Asp Ser
1               5                   10                  15

Gly Arg Ile Ser Tyr Thr Val Glu Phe Ser Leu Pro Thr His His Thr
            20                  25                  30

Val Arg Leu Ile Arg Val Thr Ala Pro Pro Ser Ala
            35                  40

<210> SEQ ID NO 101
<211> LENGTH: 55
<212> TYPE: PRT
<213> ORGANISM: Porcine reproductive and respiratory syndrome virus
<220> FEATURE:
<221> NAME/KEY: PEPTIDE
<222> LOCATION: (1)..(55)
<223> OTHER INFORMATION: Nucleocapsid protein (P69-A123) of PRRSV MD001/
      AAC98536.

<400> SEQUENCE: 101

Pro Ser Glu Arg Gln Leu Cys Leu Ser Ser Ile Gln Thr Ala Phe Asn
1               5                   10                  15

Gln Gly Ala Gly Thr Cys Ile Leu Ser Asp Ser Gly Arg Ile Ser Tyr
            20                  25                  30

Thr Val Glu Phe Ser Leu Pro Thr His His Thr Val Arg Leu Ile Arg
            35                  40                  45

Val Thr Ala Pro Pro Ser Ala
            50                  55
```

SYNTHETIC PEPTIDE-BASED MARKER VACCINE AND DIAGNOSTIC SYSTEM FOR EFFECTIVE CONTROL OF PORCINE REPRODUCTIVE AND RESPIRATORY SYNDROME (PRRS)

This application is a national phase entry under 35 U.S.C. § 371 of International Application Number PCT/US2011/068133, filed on Dec. 30, 2011, entitled "SYNTHETIC PEPTIDE-BASED MARKER VACCINE AND DIAGNOSTIC SYSTEM FOR EFFECTIVE CONTROL OF PORCINE REPRODUCTIVE AND RESPIRATORY SYNDROME (PRRS)", which is hereby incorporated by reference.

FIELD OF THE INVENTION

This disclosure relates to a peptide-based marker vaccine against Porcine Reproductive and Respiratory Syndrome (PRRS) and a set of immunodiagnostic tests for the monitoring and control of Porcine Reproductive and Respiratory Syndrome Virus (PRRSV).

BACKGROUND OF THE INVENTION

Porcine reproductive and respiratory syndrome virus (PRRSV) was discovered in the late 1980s as the cause of severe reproductive failure in sows and gilts and is one of the most important pathogens in the swine industry. Infection of sows and gilts can lead to late term abortion, early farrowing and the birth of weak-born piglets, while infected boars show decreased sperm quality and virus excretion in the semen.

In addition, PRRSV is also found to be involved in the porcine respiratory disease complex in young pigs, causing respiratory problems in combination with secondary viral and bacterial infections. The virus shows a restricted in vivo cell tropism with alveolar macrophages being the main target cell.

PRRSV is an enveloped positive single-stranded RNA virus of the family Arteriviridae and order Nidovirales (1) with approximately 15 kb in length, consisting of 9 open reading frames (ORFs). The virion consists of a nucleocapsid core that is built up by nucleocapsid protein (encoded by open reading frame 7, ORF7) in association with the viral RNA. The nucleocapsid is surrounded by a lipid envelope in which six structural proteins are embedded: the glycoproteins GP2 (ORF2a), GP3 (ORF3), GP4 (ORF4) and GP5 (ORF5), and the non-glycosylated proteins M (ORF6) and E (ORF2b). GP5 and M are considered to be the most abundant proteins in the envelope, while the other envelope proteins are present in lower amounts. The ORF1a and ORF1b situated at the 5' end of the genome encode non-structural proteins.

Similar to many other RNA viruses, PRRSV shows a large genetic variability, which is reflected in variation in virulence, interaction with the immune system and antigenic properties of viral proteins. Virus strains are usually classified within a European (EU) and a North-American (NA) genotype, based on ORF5 and/or ORF7 sequences, although a high degree of variability exists within genotypes.

PRRSV has acquired a number of properties that allow escape from the host's protective immunity. These properties are late production of virus-specific antibodies after one or two weeks upon infection; with such antibodies being unable to reduce in vitro virus replication in primary porcine alveolar macrophages (PAM); and with the much needed virus-neutralizing antibodies appearing at low levels around three to four weeks after infection thus too late to influence the acute phase of viremia (1, 2).

Despite this weak virus-neutralizing antibody response, the presence of sufficient amounts of such virus-neutralizing antibodies at the onset of infection can offer protection against virus replication in the lungs, viremia and transplacental spread of the virus, indicating that PRRSV-specific neutralizing antibodies can contribute in part to protective immunity (2,3).

The PRRS viremia was found in the blood of infected pigs with neutralizing antibodies, indicating the humoral immune response alone did not confer solid protection. The cell-mediated immunity (CMI) has been shown to play an important role in clearing PRRSV (4). The development of the CMI response in infected pigs, as determined by lymphocyte blastogenesis and adaptive cytokine production (e.g. Interferon gamma; IFN-gamma) was found delayed and became detectable in the in vitro recall response of peripheral blood mononuclear cells (PBMCs) around 4-8 weeks post infection, which correlated with the development of neutralizing antibodies (5-7). The IFN-gamma plays a key role in cell-mediated immune responses against a variety of cytopathic viral infections in animals. In PRRSV-infected pigs, the IFN-gamma mRNA was detected in the lymph nodes, lungs and peripheral blood mononuclear cells (7).

The search for antigenic regions across the entire PRRSV structural proteome representing virus-neutralizing antibody inducing B cell epitopes and IFN-gamma eliciting T cell epitopes has been one of the most challenging topics in veterinary viral immunology over the past two decades. Representative articles showing such epitope mapping outcome as a result of the cumulative efforts by the global PRRSV research community are herein provided as references (8-10).

Despite the commercial availability of modified-live vaccines (MLV) as well as killed PRRSV viral lysate vaccines, the control of PRRSV related diseases still remains problematic. One major problem is efficacy in that PRRSV vaccines are efficacious against homologous, but not heterologous, challenge. In addition, safety issues for the MLV have been reported in the field. Modified live vaccines are not suitable for use in pregnant sows, gilts and in boars as vaccination may result in shedding of vaccinal virus in semen. Modified live virus vaccines can persist in vaccinated animals. Transmission to non-vaccinated animals and subsequent vaccine-virus-induced disease have been reported. Furthermore, there is an urgent need for the development of a marker vaccine to allow differentiation between infected and vaccinated pigs, thus facilitating traceability and control of PRRSV infection.

In summary, there remains an urgent need to design immunogenic PRRSV peptides comprising distinct functional B and T cell epitopes, that are capable of inducing protective antibodies and cellular immune responses, as well as vaccine formulations incorporating these designer peptides to allow for cross-protection of PRRSV strains in swine. With the availability of these rationally designed and molecularly characterized immunogenic peptides, there is also the need to identify antigenic peptides capable of being recognized by antibodies from infected pigs, and to use these designer peptides to develop a set of diagnostic tests, thus a diagnostic system, for serological identification of infected versus vaccinated animals to allow for effective control of PRRSV infection. Finally, there is this need to develop means for low cost manufacture and quality control of such peptide-based marker vaccine and diagnostic system for wide application to effectively monitor and control the PRRS disease.

References

1. Gorbalenya, A, et al. 2006. Nidovirales: evolving the largest RNA virus genome. Virus Res 117:17-37.
2. Lopez, O J, et al. 2007. Protection against porcine reproductive and respiratory syndrome virus (PRRSV) infection through passive transfer of PRRSV-neutralizing antibodies is dose dependent. Clin Vaccine Immunol 14:269-75.
3. Lopez, O J, and Osorio F A. 2004. Role of neutralizing antibodies in PRRSV protective immunity. Vet Immunol Immunopathol 102:155-63.
4. Mateu, E., Diaz, I, 2008. The challenge of PRRS immunology. Vet. J. 177 (3), 345-351.
5. Bassaganya-Riera, J, et al. 2004. Impact of immunizations with porcine reproductive and respiratory syndrome virus on lymphoproliferative recall responses of CD8+ T cells. Viral Immunol. 17: 25-37.
6. Bautista, E. M, and Molitor, T. W. 1997. Cell-mediated immunity to porcine reproductive and respiratory syndrome virus in swine. Viral Immunol. 10: 83-94.
7. Lopez Fuertes, L, et al. 1999. Analysis of cellular immune response in pigs recovered from porcine respiratory and reproductive syndrome infection. Virus Res. 64: 33-42.
8. Vanhee, M, et al. 2011. Characterization of antigenic regions in the porcine reproductive and respiratory syndrome virus by the use of peptide-specific serum antibodies. Vaccine. 29:4794-4804.
9. Wang, Y X, et al 2011. Identification of immunodominant T-cell epitopes in membrane protein of highly pathogenic porcine reproductive and respiratory syndrome virus. Virus Research doi: 10.1016
10. Diaz, I, et al. 2009. In silico prediction and ex vivo evaluation of potential T-cell epitopes in glycoproteins 4 and 5 and nucleocapsid protein of genotype-I (European) of porcine reproductive and respiratory syndrome virus. Vaccine 27: 5603-5611.
11. Wang, C Y. Artificial T helper cell epitopes as immune stimulators for synthetic peptide immunogens including immunogenic LHRH peptides. U.S. Pat. No. 6,025,468.
12. Wang, C Y. Artificial T helper cell epitopes as immune stimulators for synthetic peptide immunogens. U.S. Pat. No. 6,713,301.
13. Wang, C Y, Finstad, Connie L., Walfield, Alan M., Sia Charles, Sokoll, Kenneth K., et. al. Site Specific UBITh Amyloid-β Vaccine for Immunotherapy of Alzheimer's Disease. Vaccine, 2007: 25: 3041-3052.
14. Wang, C Y, Walfield, Alan M. Site-specific peptide vaccines for immunotherapy and immunization against chronic diseases, cancer, infectious diseases, and for veterinary applications. (Review Article) Vaccine 2005: 23:2049-2056.
15. Hseuh, P R, Kao C L, Lee C N, Chen L K, Ho M S, Sia C, Fang X D, Lynn S, et al and Wang, C Y. Highly Specific SARS Antibody Test for Serosurveillance. Emerg. Infect. Diseases 2004, 10:1558-1562
16. Finstad, C L, Wang, C Y, et al. Synthetic luteinizing hormone releasing hormone (LHRH) vaccine for effective androgen deprivation and its application to prostate cancer immunotheray. Vaccine 2004: 22:1300-1313
17. Wang, C Y, et al. Synthetic IgE peptide vaccine for immunotherapy for allergy. Vaccine 2003, 21:1580-1590.
18. Wang, C Y, et al. Synthetic AIDS vaccine by targeting HIV receptor. Vaccine 2002, 21: 89-97.
19. Wang, C Y, et al. Effective Synthetic peptide vaccine for foot-and-mouth disease in swine. Vaccine. 2002, 20:2603-2610.
20. Wang, C Y, et al. Synthetic Peptide-based Vaccine and Diagnostic System for Effective Control of FMD. Biologicals 2001, 29: 221-228.
21. Fuerst, T R, Niles E G, Studier F W, and Moss B. Eukaryotic transient-expression system based on recombinant vaccinia virus that synthesizes bacteriophage T7 RNA polymerase. Proc. Natl. Acad. Sci. USA 1986; 83:8122-8126.
22. Chen, C-M, Liu H-T, Tu C-F. Effects of PCV2 infection in a transgenic SPF pig farm in Taiwan. 13th AAAP Anim. Sci. Congr. Sep. 22-26, 2008 Hanoi, Vietnam. Proceedings, p. 420.
23. Das, P B, et al. The Minor Envelope Glycoproteins GP2a and GP4 of Porcine Reproductive and Respiratory Syndrome Virus Interact with the Receptor CD163. 2010. J. Virol. 84:1731-1740.
24. Harlow, E, and Lane, D. Antibodies: A Laboratory Manual. Chapter 14 Immunoassays, pp 555-612. Cold Spring Harbor Laboratory, Cold Spring Harbor, N.Y. 1988.

BRIEF DESCRIPTION OF THE INVENTION

This disclosure relates to a peptide-based marker vaccine against Porcine Reproductive and Respiratory Syndrome (PRRS) and a set of immunodiagnostic tests for the prevention, monitoring and control of Porcine Reproductive and Respiratory Syndrome Virus (PRRSV).

Despite the available scientific information on the antigenic regions across the structural PRRSV proteome, due to the inability of the research community to develop any successful peptide based vaccines against infectious agents after decades of efforts, there are those who are of the opinion that it is improbable that synthetic peptide vaccines will ever be produced for the majority of pathogens. This inventor has learned much from the first generation biological vaccines where a rational design approach incorporating selective PRRSV B and T cell epitopes should allow validation and development of synthetic peptide based PRRSV vaccine(s) against the desired viral strains and companion diagnostic tests for the monitoring and control of the disease. It is important to recognize that the B cell neutralizing epitopes are largely conformational and must be taken into consideration when designing those B cell epitope related peptide immunogens. Identification and design of the relevant B antigenic epitopes will require an understanding of the relationship between structure of the targeted molecule and its function. Such a discipline in understanding the structure and function of a target molecule subject to immunogen design is termed by this inventor as "functional antigenics". In addition, the immune response is complex and multi-faceted. A vaccine against a rapidly evolving RNA virus that exists as a quasi-species population should always aim to stimulate as many different protective immune mechanisms as possible to minimize the risk of emergence of virus variants that escape the host's immune system.

Successful synthetic peptide based vaccines will comprise components that stimulate the appropriate elements of the immune system which includes adaptive and innate immunities. Another major hurdle in developing epitope based peptide vaccines is due in part to the non-immunogenic nature of the short length peptides representing these epitopes. In addition, there is a need for incorporation of a large repertoire of B and T epitopes to allow universality of the vaccine for broad cross-protection arising out of pathogen's genetic variation as well as the host's genetic variability. With extensive efforts and experimental validation of synthetic peptide-based vaccines and diagnostic tests against various diseases, this inventor has focused on rational design of peptide immunogens mimicking antigenic sites on the native target molecule for elicitation of antibodies for in vitro and in vivo serological and functional studies, supplemented by suitable T cell epitopes for enhancement of the desired immunogenicity. This has led to optimized antigens, immunogens and vaccine formulations in each of the target diseases for clinical and commercial applications (11-20).

Vaccine formulations according to various embodiments of the invention contain a mixture of peptides derived from PRRSV GP2, GP3, GP4, or GP5 proteins; each peptide individually comprises a B cell PRRSV neutralizing/receptor binding epitope which is individually linked to an artificial T helper epitope for enhancement of the respective peptide's immunogenicity; and which can be supplemented with a mixture of peptides representing the T helper epitopes derived from the PRRSV GP4, GP5, M and Nucleocapsid proteins to provide cell mediated immunity. Such viral peptide compositions are prepared in an acceptable delivery system as vaccine formulations and can provide cross protection of PRRSV antibody free pigs from infection upon PRRSV challenge.

The diagnostic system according to various embodiments of the invention contains a set of diagnostic tests, with one test providing for two overlapping PRRSV ORF7-encoded antigenic peptides in an ELISA immunoassay format for optimal antibody recognition from PRRSV—infected animals, and the other tests providing for GP2, GP3, GP4 and GP5 derived vaccine target peptides in an ELISA immunoassay format for optimal antibody recognition from PRRSV peptide vaccine immunized animals. In combination, these diagnostic tests constitute a diagnostic system for Differentiation of Infected from Vaccinated Animals (DIVA) thus effective monitoring and control of the disease.

It also relates to method for the manufacture of such a vaccine for protecting pigs against PRRSV infection, and for the manufacture of a set of immunodiagnostic tests for DIVA, thus allowing for effective control of the disease.

Peptides or peptide compositions of the present invention are designed and optimized by an extensive process of serological validation in target species for development of marker vaccines for cross-reactivities with natural virus, cross protection of PRRSV antibody free piglets from infection upon PRRSV challenge, and development of a set of peptide based ELISAs for differentiation of infected from vaccinated animals.

This disclosure relates to a PRRSV vaccine, comprising specifically, a peptide and a peptide composition originating from B epitopes of PRRSV GP2, GP3, GP4 or GP5 proteins with each peptide optionally linked to a T helper epitope to enhance the peptide's immunogenicity so as to induce in the immunized host humoral immunity including high titers of antibodies that are crossreactive with PRRSV.

The peptide or peptide composition is further supplemented by additional peptides representing T cell epitopes of PRRSV GP4, GP5, M and Nucleocapsid proteins in a vaccine formulation to mount cell-mediated immune responses.

Various embodiments of the invention are provided. One set of embodiments is directed to the peptide(s) and peptide composition(s) effective as the antigens for detection of antibodies to the nucleocapsid (NC) protein from the infected animals. A second set of the embodiments is directed to peptide and peptide composition effective for detection of antibodies to the marker vaccine targeted GP2, GP3, GP4 and GP5 epitopes from the vaccinated animals. These diagnostic tests constitute a diagnostic system for DIVA thus effective control of the disease.

There is another set of embodiments directed to peptide(s), homologues and analogues thereof, derived from both the B and T cell epitopes of the PRRSV proteins. Such PRRSV peptides are preferentially, but optionally, linked to an artificial combinatorial T helper epitope to enhance their respective immunogenicity.

In addition, in another set of embodiments are directed to vaccine formulations comprising peptide and peptide composition from PRRSV B and T cell epitope derived peptide immunogens to elicit both antibody responses that are crossreactive with the natural PRRSV protein antigens and cell mediated immune responses together to protect pigs against PRRSV infection.

Each such designed peptide can be chemically synthesized from milligram to kilogram scales for industrial application, and be quality controlled.

Also provided by various embodiments of the invention are delivery vehicles and other ingredients routinely incorporated with vaccine formulations.

BRIEF DESCRIPTION OF THE FIGURES

FIG. 2A Localization of antigenic sites on the nucleocapsid (NC) protein of PRRSV MD001 strain (Accession No. AF121131) and identification of antigenic peptide (SEQ ID NO: 1) for use in UBI PRRSV NC ELISA for detection of antibodies to the NC protein in infected animals.

FIG. 2B. Localization of antigenic sites on the nucleocapsid (NC) protein of PRRSV MD001 strain (Accession No. AF121131) and identification of antigenic peptides (SEQ ID NO. 2) for use in UBI PRRSV NC ELISA for detection of antibodies to the NC protein in infected animals.

FIG. 3. Alignments for Homologous Nucleocapsid Protein Sequences from PRRSV Strains MD001 (SEQ ID No: 3), JXA1 (SEQ ID No: 4), NA(SEQ ID No: 5) and EU (SEQ ID No. 6).

FIG. 6A. UBI PRRSV marker vaccine formulations elicited specific high titer antibodies to the target peptide immunogens in PRRSV infected pigs as detected and differentiated by UBI's diagnostic system (i.e. test to detect PRRSV infected pigs and tests to detect animals received vaccine formulations containing designer peptide immunogens derived from GP2, 3, and 4 proteins).

FIG. 6B. UBI PRRSV marker vaccine formulations elicited specific high titer antibodies to the target peptide immunogens in PRRSV infected pigs as detected and differentiated by UBI's diagnostic system (i.e. test to detect PRRSV infected pigs and tests to detect animals received vaccine formulations containing designer peptide immunogens derived from GP3, 4 and 5 proteins).

DETAILED DESCRIPTION OF THE INVENTION

Figure 1A:
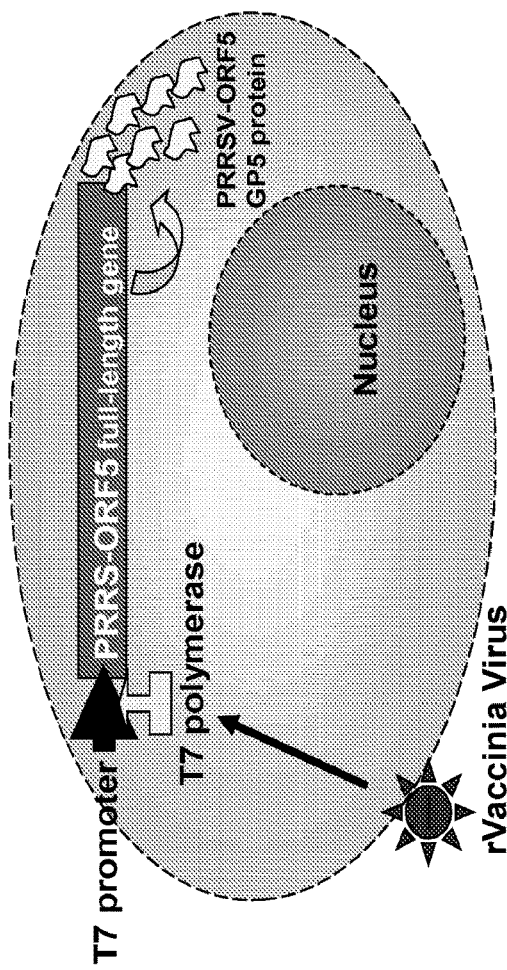
FIG. 1A. Illustration showing the mechanism for detecting antibodies to PRRSV GP5 protein inside the cytoplasm of co-transfected HTK cell line cells by immunofluorescence according to an embodiment of the invention.

Peptide antigens can detect immunological responses and certain peptide antigens may also stimulate immunological responses. Many peptide antigens can be used for the sensitive and specific detection of immune responses but most often they do not by themselves act as immunogens. Peptide immunogens are a special class of peptide antigens that can be used to stimulate immune responses as well as to detect them. According to one embodiment of the invention, the peptide antigens in the PRRSV vaccine are peptide immunogens that have both B cell (B) and T helper cell (Th) epitopes that together act to stimulate the generation of protective immune responses, and there are also a different set of peptide antigens that are capable of detecting immune responses to PRRSV infection.

One method for identification of B cell epitopes relies on a set of nested and overlapping peptides of multiple lengths, typically ranging from 20 to 60 residues or longer in length. These longer peptides are synthesized by a laborious series of independent solid-phase peptide syntheses. The resulting sets of nested and overlapping peptides can then be used in antibody binding studies to identify peptides which best present immunodominant determinants, including discontinuous conformational B cell epitopes. One embodiment of the invention provides for two overlapping PRRSV ORF7-encoded nucleocapsid peptides with one comprises 70 amino acid sequence (SEQ ID No: 1, also shown in FIG. 2A) and another one comprises 73 amino acid sequence (SEQ ID No: 2, also shown in FIG. 2B) with each having on its own a cluster of B cell epitopes for optimal antibody recognition. These antigenic peptides were empirically identified and optimized using serum samples from PRRSV-infected piglets and an ELISA immunoassay format. Any immunoassay format that can be adapted to an antibody capture phase comprising peptide antigens, e.g., ELISA, can be used to detect and quantify antibodies that bind to a particular fragment of a PRRSV nucleocapsid protein in a blood, serum, or plasma sample from a PRRSV-infected pig.

In a specific embodiment, an optimized PRRSV antigenic peptide of about 70 amino acids (SEQ ID No: 1), which corresponds to amino acid residues 2 to 71 of a full-length PRRSV nucleocapsid protein, and another optimized PRRSV antigenic peptide of about 73 amino acids (SEQ ID No: 2), which corresponds to amino acid residues 51 to 123 of a full-length PRRSV nucleocapsid protein were identified. The two peptides were combined in a mixture at an equal ratio to constitute the most optimal antibody capture phase for the detection of antibodies to PRRSV by ELISA in the infected pigs. These two highly antigenic peptides were both found to have a cluster of immunodominant B cell epitopes and had the most significant and consistent antigenicity for the PRRSV positive serum panel. The production and use of diagnostic test kits comprising PRRSV Nucleocapsid peptides (e.g. SEQ ID No: 1 and No: 2) are within the scope of various exemplary embodiments of the invention.

Specific embodiments of the PRRSV antigenic peptide invention are further defined as being immunologically functional homologues of SEQ ID Nos: 1 and 2 that have corresponding sequences and conformational elements from mutant and variant strains of PRRSV. Homologous PRRSV antigenic peptides have amino acid residues that correlate approximately with nucleocapsid protein positions 2 to 71 and 51 to 123 of the originating variant PRRSV North American strains. Such homologues are readily demonstrated through sequence alignment programs such as ClustalW (produced by Julie D. Thompson, Toby Gibson of European Molecular Biology Laboratory, Germany and Desmond Higgins of European Bioinformatics Institute, Cambridge, UK. Algorithmic). FIG. 3 shows the alignment by ClustalW of four antigen sequences taken from diverse strains of PRRSV MD001 Taiwan/99Y/AF121131 (SEQ ID No: 3), JXA1 Beijing/06Y/EF112445 (SEQ ID No: 4), NA/NJ-a/04Y/AY37282, (SEQ ID No:5), EU/Lena/08Y/EU 909691 (SEQ ID No: 6). The originating PRRSV strains of the nucleocapsid homologues aligned in FIG. 3 include viruses of European strains. Table 1 also exemplifies homologues (SEQ ID No: 7 and SEQ ID No: 8) of antigenic peptides SEQ ID No:1 and SEQ ID No: 2 (North American strain/MD001/TW/AAC98536) with EU being the originating PRRSV strain (European strain/08V204/Belgium/EU/ GU737266). In one embodiment, the homologue to SEQ ID No: 1 (SEQ ID No: 7) has an amino acid sequence from about amino acid position 2 to about amino acid position 72 of a PRRSV NC protein from the EU strain. In another embodiment, the homologue (SEQ ID No: 8) has an amino acid sequence from about amino acid position 52 to about amino acid position 128 of a PRRSV NC protein from the EU strain. These two homologous peptides can similarly be combined in a mixture at an equal ratio to constitute the most optimal antibody capture phase for the detection of antibodies to PRRSV, preferably the European strains, by ELISA in the infected pigs.

Homologues of the invention are further defined as having at least 50% identity to SEQ ID No: 1 and SEQ ID No: 2. In one embodiment, the variant strain homologue (SEQ ID NO: 7) has about 50% identity to SEQ ID No: 1. In another embodiment, the variant strain homologue (SEQ ID NO: 8) has about 64% identity to SEQ ID No: 2.

In addition to the antigenic peptides identified from the PRRSV NC protein useful for detection of antibodies from serum samples of infected animals, there are antigenic regions present on PRRSV GP2, GP3, GP4 and GP5 proteins which correspond to neutralizing and/or receptor binding functional sites. Various peptide immunogens were designed around these epitopic regions for assessment of their respective immunogenicity by target peptide based ELISAs, and more importantly, for the crossreactivities of the elicited antibodies to the native PRRSV proteins by the immunofluorescence assay (IFA) according to an embodiment of the invention. In addition, there are well documented immunodominant T cell epitopes present on PRRSV GP4, GP5, M and NC proteins. Peptides from these T helper sites would trigger lymphocyte proliferative responses in pigs leading to cytokine, including IFN-gamma, production which plays a key role in cell-mediated immune responses against a variety of cytopathic viral infections in animals.

Figure 4:
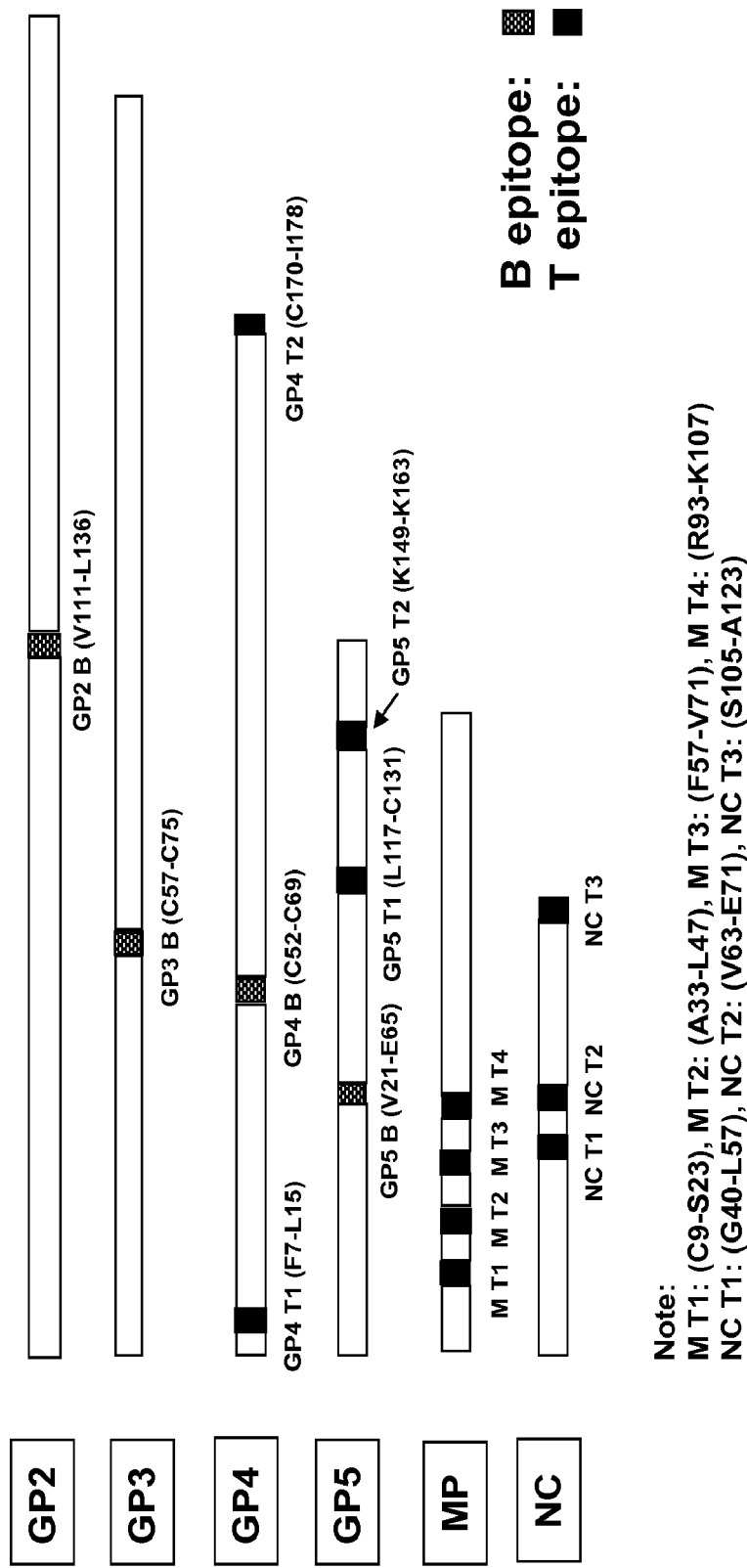
FIG. 4. Localization of selected B and T cell epitopes on the PRRSV ORF 2 to ORF 7 proteins of PRRSV JXA1 strain (Accession No. AY2G2352) adapted for marker vaccine design.

An embodiment as shown in FIG. 4 illustrates the distribution and location of those selected B and T cell epitopes of the invention on the PRRSV ORF 2 to ORF 7 encoded (GP2, GP3, GP4, GP5, M, and N) proteins based on the sequence of PRRSV JXA1 (Accession number AY2G2352).

Another embodiment of the invention provides for the sequences of the four optimized and selected PRRSV B cell epitope cluster peptides, namely GP5.3(V21-E65) (SEQ ID No:9), GP2 B(V111-L136) (SEQ ID No:10), GP3B (C57-C75) (SEQ ID No:11), and GP4B (C52-C69) (SEQ ID No:12). These B cell epitope cluster are located around the sites having neutralizing and receptor binding characteristics.

Other embodiments of the invention provide for immunologically functional analogues of these four PRRSV B cell epitope cluster peptides. Table 3 shows the alignments for homologous GP5 (SEQ ID Nos: 13-15), GP2(SEQ ID Nos: 17-19), GP3(SEQ ID Nos: 21-23), and GP4(SEQ ID Nos: 25-27) derived B epitope cluster peptide sequences with originating strains being MD001, JXA1, NA and EU. A consensus sequence for each of the B cell epitope cluster peptides (SEQ ID NOs: 16, 20, 24, 28) is also shown wherein the amino acids assigned to the variable positions are those most frequently applied for those positions.

An immunologically functional analogue of the B cell epitope cluster peptide includes variants of SEQ ID Nos: 9, 10, 11, 12 and homologues which retain substantially the same immunological properties as the original antigenic peptide. For example, variants that are functional analogues or homologues of SEQ ID No: 9 can have a conservative substitution in an amino acid position; a change in overall charge; a covalent attachment to another moiety; or small additions, insertions, deletions or conservative substitutions and/or any combination thereof. Thus, antibodies that bind to a PRRSV GP5.3 B epitope (V21-E65) antigenic peptide (e.g., SEQ ID No: 9) will also bind to the immunologically functional analogues of that PRRSV GP5.3 B epitope antigenic peptide with substantially similar efficacy. In one embodiment, the functional analogue has at least 40% identity to SEQ ID No: 9 or homologue. In another embodiment, the functional analogue has at least 56% identity to SEQ ID No: 11 or homologue. In yet another embodiment, the functional analogue has at least 72% homology to SEQ ID No: 12 or homologue. In yet another embodiment, the functional analogue has at least 80% homology to SEQ ID No: 10 or homologue. In still another embodiment, the functional analogue has at least 94% homology to SEQ ID No: 12 or homologue.

In one embodiment, as shown in Table 3, immunologically functional analogues of the PRRSV GP 5.3 B epitope cluster peptide (V21-E65) encompasses versions of PRRSV GP5.3 B epitope cluster peptide that have been modified by conservative substitutions, and by insertions or deletions. In this embodiment, immunologically functional analogues can be modified from SEQ ID No: 9 or from a homologue of SEQ ID No: 9 by substitutions that are conservative.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In another embodiment, as shown in Tables 3 and 4, immunologically functional analogues can be modified by amino acid additions to the N-terminus, C-terminus, and/or by insertions into the middle of the peptide. In various embodiments of the invention, additions are to the N-terminus or C-terminus of the peptide. Additions can be of 1, 2, 3, 4, 5, 6, 7, 8, 9, 10, or 11 amino acid residues (SEQ ID Nos: 9 and 30). Such additions may constitute amino acid sequences which are not present in PRRSV protein and which do not alter the immunogenicity of the PRRSV B epitope cluster peptide. Additions which are not present in PRRSV B epitope cluster peptide include, but are not limited to, small charged sequences (e.g., lysine-lysine-lysine), amino acids that enable the formation of branched structures (e.g., εN-lysine) or enable the formation of cyclized structures (e.g., cysteine). In an embodiment of the invention, additions of amino acid sequences that are not present in PRRSV are of 5 amino acids or less. Amino acid additions can be either classical or non-classical amino acids or a mixture thereof.

In another specific embodiment, immunologically functional analogues can be modified by amino acid deletions to the N-terminus, C-terminus, and/or middle of the peptide. In various embodiments, deletions are to the N-terminus or C-terminus of the peptide. Deletions can be of 1, 2, 3, 4, 5, 6, 7, 8, 9, 10, or 11 amino acid residues. In a specific embodiment as shown in Table 4, deletions of amino acid sequences are of 9 amino acids or less (SEQ ID Nos: 33 and 34).

In another embodiment, as shown in Table 7, immunologically functional analogues of PRRSV B epitope cluster peptide encompass PRRSV B epitope cluster antigenic peptides that have been modified by an alteration in charge. Such alteration in charge may be the result of amino acid substitutions, additions, or deletions, or the covalent attachment of a charged molecule. The alteration in charge may have the result of making the peptide more basic, more acidic, or more neutral as compared to the unmodified peptide. In a specific embodiment, the peptide is made more basic by the addition of 1-5 lysine residues to the N-terminus or C-terminus. In a more specific embodiment, the peptide is made more basic by the addition of 3 lysine residues to the N-terminus.

By way of a non-limiting example, immunologically functional analogues of the peptide of the invention can have from 1 to about 5 additional amino acids (classical and non-classical) added to the terminal amino acids. For example, the sequence Lys-Lys-Lys can be added to the amino terminus of this PRRSV B cell epitope cluster peptide for a change in charge.

The peptides can be readily synthesized using standard techniques, such as the Merrifield solid phase method of synthesis and the myriad of available improvements on that process. The peptides can also be made using recombinant DNA technology. As such, nucleic acid molecules encoding the PRRSV B cell epitope cluster antigenic peptide and immunologically functional analogues of the PRRSV B cell epitope cluster antigenic peptide and compliments thereof are encompassed by various exemplary embodiments of the invention. Vectors, especially expression vectors, comprising the nucleic acid molecules encoding PRRSV B cell epitope cluster antigenic peptides and immunologically functional analogues are also encompassed by various exemplary embodiments of the invention. Host cells containing the vectors are also encompassed by various exemplary embodiments of the invention.

Various exemplary embodiments of the invention also encompass methods of producing the PRRSV antigenic peptides and immunologically functional analogues of the PRRSV antigenic peptides. For example, the method can comprise incubating a host cell containing an expression vector comprising a nucleic acid molecule encoding a PRRSV antigenic peptide and/or immunologically functional analogue of an PRRSV antigenic peptide under such conditions that the PRRSV peptide and/or immunologically functional analogue of a PRRSV peptide is expressed.

One embodiment of the invention provides peptide compositions produced by solid-phase synthesis. This embodiment can use controlled and well-defined immunogens derived from the lysates or secretions of infected cells. The quality of antigens produced by the chemical process of this embodiment are controlled and defined and, as a result, reproducibility of antigenicity, immunogenicity and yield can be assured. Also, no biohazardous materials are used in the manufacture of peptide antigens, reducing risks and eliminating the need for expensive biological containment. As site-specific immunogens presenting high molar concentrations of selected epitopes, both the safety and immunopotency of the vaccine employing PRRSV antigenic peptide compositions are assured.

In one embodiment, the peptides of the invention are synthesized. The use of defined PRRSV antigenic synthetic peptides minimizes the false-positive results when used as antigen for antibody detection and diagnosis in piglets. The use of defined synthetic peptides, having known B cell and Th epitopes, as immunogens eliminates the undesired non-PRRSV-specific immune responses caused by the presence of antigenic materials originating from PRRSV-infected or recombinant virus-infected host cells and from recombinant protein expression systems that may be co-purified with PRRS virus and/or recombinant proteins, when used as the immunogenic ingredients of a vaccine. For example, sera from pigs may have antibodies to host cells, or to recombinant *Escherichia coli*, yeast or baculovirus which are then cross-reactive with the antigenic materials used in diagnostic tests based on the biologically-derived antigens, and such immune responses generated by vaccines having these extraneous immunogens as ingredients will be non-protective. In contrast, pigs receiving a PRRSV peptide vaccine of the invention will generate focused immune responses devoid of untoward antibodies and other immune responses to proteins originating from host cells or expression vectors, e.g., proteins from recombinant *Escherichia coli*, yeast or baculovirus that had been co-purified with the biologically-derived PRRSV antigens.

This embodiment of synthetic peptides also minimizes interference from impurities that are generated during production. With long syntheses, despite the rigorous control of coupling efficiency, peptide analogues are also produced due to events during elongation cycles, including amino acid insertion, deletion, substitution, and premature termination, thus yielding to the generation of multiple peptide analogues along with the targeted peptide syntheses. Nonetheless, such peptide analogues are still suitable in peptide preparations as contributors to antigenicity and immunogenicity when used in immunological application either as solid phase antigen for purpose of immunodiagnosis or as immunogen for purpose of vaccination.

During 25 years of experience in immunological applications of synthetic peptides, we have found that the range in structural variability that allows for retention of an intended immunological activity is far more accommodating than the range in structural variability allowed for retention of a specific drug activity by a small molecule drug or the desired activities and undesired toxicities found in large molecules that are co-produced with biologically-derived drugs. This is why peptide analogues, either intentionally designed or inevitably produced by errors of the synthetic process as a mixture of deletion sequence byproducts that have chromatographic and immunologic properties similar to the intended peptide, are frequently as effective as a purified preparation of the desired peptide. Designed analogues and unintended analogue mixtures are effective as long as a discerning QC procedure is developed to monitor both the manufacturing process and the product evaluation process so as to guarantee the reproducibility and efficacy of the final products employing these peptides.

In other embodiments of the invention, endogenous PRRSV Th peptides and homologues thereof (SEQ ID No. 47-79) can be included in the vaccine compositions. The presence of Th peptides can improve immunogenicity of the PRRSV peptide vaccine. PRRSV B epitope derived immunogenic peptides (including the homologues and analogues described above) can be mixed with endogenous PRRSV Th epitopes.

In other embodiments of the invention, endogenous PRRSV Th peptides can be presented as a combinatorial sequence where a combination of amino acid residues are represented at specific positions within the framework based on the sequences of the homologues for that PRRSV Th peptide. An assembly of combinatorial peptides can be synthesized through one synthesis process by adding a mixture of the designated protected amino acids, instead of one particular amino acid, at a specified position during the synthesis process. Such combinatorial PRRSV Th peptide assembly can allow broad T helper epitope coverage for animals of a diverse genetic background. Representative combinatorial sequences of PRRSV Th peptides are shown in Table 7 SEQ ID Nos 80-90 as derived from Table 6 SEQ ID Nos 47-79 for each of the PRRSV Th epitope.

In one embodiment, Th peptides having clusters of immunodominant PRRSV Th epitopes from ORF 4, ORF5, ORF6 and ORF7, described as SEQ ID Nos: 47, 51, 55, 59, 61, 63, 67, 70, 74, 76 based on JXA1 sequence (also shown in Table 6) and unlinked to the PRRSV B peptide immunogens, can be used to supplement the immunogenicity of PRRSV B epitope peptide immunogens to enhance the immunogenicity of peptide based PRRSV vaccine formulations as shown in Example 5. Including SEQ ID Nos: 47, 51, 55, 59, 61, 63, 67, 70, 74, 76 as free peptides, without covalent linkages to the B epitope peptide immunogens, can improve immunogenicity of the vaccine formulations. In another embodiment as described in Example 10, including SEQ ID Nos: 47, 51, 55, 59, 61, 63, 67, 70, 74, 76 for group 2, and SEQ ID NOs 80 to 90 for groups 1, 3, and 4 as free peptides, without covalent linkages to the B epitope peptide immunogens, can improve immunogenicity of the vaccine formulations.

In another embodiment, PRRSV peptides (including homologues and analogues described above) can be covalently linked, with or without a spacer, to a peptide containing a sequence known to contain a Th epitope. This embodiment can offer enhanced immunogenicity over the equivalent immunogens without the covalently linked Th epitope. In a specific embodiment, the peptide containing the Th epitope is covalently linked to the N-terminus (SEQ ID No: 38) and/or C-terminus (SEQ ID No: 39) of the PRRSV peptide. In another specific embodiment, the spacer has the sequence Lys-Lys-Lys-εNLys (SEQ ID No: 36), or a single amino acid εNLys also shown in Table 5 (SEQ ID Nos: 43 and 42 respectively). In an embodiment, the peptide containing the Th epitope is covalently linked to the amino terminus of the PRRSV peptide. In a specific embodiment, the peptide as shown in Table 5 (SEQ ID No: 40) containing the Th epitope is the artificial combinatorial Th peptide SEQ ID No: 35 (as shown in Table 5) linked to the amino terminus through a Lys-Lys-Lys-εNLys spacer (SEQ ID No: 36), and presented as SEQ ID No: 40.

Various embodiments of the invention relate to vaccine compositions for protecting pigs against PRRSV. In exemplary embodiments, the vaccine comprises an immunogenic peptide antigen or peptide immunogen composition and an acceptable delivery vehicle or adjuvant. In various embodiments, the PRRSV vaccine composition, comprises a peptide antigen or peptide antigen composition and a veterinarily acceptable delivery vehicle or adjuvant, wherein the peptide antigen comprises an amino acid sequence selected from the group consisting of:
  a) from any one of the PRRSV B cell Epitope Cluster peptide antigens GP5.3 (V21-E65) (SEQ ID No: 9), GP 2 B (V111-L136) (SEQ ID No: 10), GP3B (C57-C75) (SEQ ID No: 11) and GP4 B (C52-C69) (SEQ ID No: 12);
  b) a homologue of (a);
  c) an antigenically and immunologically functional analogue of (a) or (b),
  d) (a), (b), or (c) having at least one conservative amino acid substitution, amino acid addition, and/or amino acid deletion; and
  e) any combination of (a)-(d).

In an embodiment of the PRRSV vaccine, the charge of the peptide antigen is altered by adding or deleting 1 to 5 amino acids. In another embodiment of the PRRSV vaccine, the antigenically and immunologically functional homologue or analogue has at least 50% identity to the antigen of the amino acid sequence that is from any one of the PRRSV B cell Epitope Cluster peptide antigens GP5.3 (V21-E65) (SEQ ID No: 9), GP 2 B (V111-L136) (SEQ ID No: 10), GP3B (C57-C75) (SEQ ID No: 11) and GP4 B (C52-C69) (SEQ ID No: 12); derived from GP2, GP3, GP4 and GP5. In a particular embodiment, the peptide antigen has an amino acid sequence selected from the group consisting of SEQ ID Nos: 9, 10, 11, 12.

In another embodiment of the PRRSV vaccine the peptide antigen further comprises a T helper epitope covalently linked to the N-terminus or C-terminus of the peptide antigen. In a specific embodiment, the T helper epitope is covalently linked to the amino terminus of the peptide antigen. In another specific embodiment, the T helper epitope is covalently linked to the peptide antigen through a spacer having at least one amino acid. In a particular embodiment, the T helper epitope is SEQ ID No: 35. In yet another particular embodiment, the spacer is Lys-Lys-Lys-εNLys (SEQ ID NO: 36). In yet another particular embodiment, the spacer is εNLys. In a specific embodiment, the peptide antigen is SEQ ID No: 42, 43, 44, 45 or 46.

In various exemplary embodiments, any amount of immunogenic peptide antigen can be used to elicit immune responses in the animal. In a particular embodiment, the amount of peptide antigen is between about 0.1 µg to about 100 mg. In another particular embodiment, the amount of peptide antigen is between about 1 µg to about 10 mg. In yet another particular embodiment, the amount of peptide antigen is between about 10 µg to about 1 mg.

In various embodiments of the PRRSV vaccine composition the composition further comprises an equimolar mixture of eleven PRRSV T helper epitope peptides of SEQ ID Nos: 47, 51, 52, 55, 59, 61, 63, 67, 70, 74, and 76. In a specific embodiment, the amount of the equimolar mixture of SEQ ID Nos: 47, 51, 52, 55, 59, 61, 63, 67, 70, 74, and 76 is between about 0.1 µg to about 1 mg. In a more specific embodiment, the amount of the equimolar mixture of SEQ ID Nos: 47, 51, 52, 55, 59, 61, 63, 67, 70, 74, and 76 is between about 1 µg to about 100 µg.

In various exemplary embodiments, any type or amount of delivery vehicle or adjuvant can be used. In a particular embodiment, the delivery vehicle and adjuvant is Montanide™ ISA 50V (an oil vaccine adjuvant composition comprised of vegetable oil and mannide oleate for production of water-in-oil emulsions), Tween® 80 (also known as: Polysorbate 80 or Polyoxyethylene (20) sorbitan monooleate), a CpG oligonucleotide, and/or any combination thereof.

In a specific embodiment, the PRRSV vaccine composition, comprises a peptide antigen of SEQ ID No: 33 and a veterinarily acceptable delivery vehicle or adjuvant, wherein the amount of peptide antigen is between about 10 µg to about 1 mg.

Another embodiment of the invention relates to a method for protecting piglets that are or are not PRRSV Maternally Derived Antibody (MDA) positive against PRRSV infection, comprising administering a vaccine encompassed by any of the exemplary embodiments as described above.

A mixture of two PRRSV NC peptides with SEQ ID Nos: 1 and 2 was prepared in accordance with the present disclosure can also be used to detect PRRSV antibodies by using the peptide in an antigenically effective amount in the capture phase of an immunoassay, e.g., in the solid phase immunosorbent of ELISA test kits. In accordance with an embodiment of the present invention, any compatible immunoassay format can be used with the subject peptides. Such formats are well known to the ordinarily skilled artisan and have been described in many standard immunology manuals and texts, see for example Harlow et al. 1988 (24). These include, among other well-known immunoassay formats, an enzyme-linked immunoadsorbent assay (ELISA), an enzyme immunodot assay, an agglutination assay, an antibody-peptide-antibody sandwich assay, a peptide-antibody-peptide sandwich assay. In an embodiment, the immunoassay is an ELISA using a solid phase coated with a peptide composition comprising two PRRSV NC antigenic peptides (SEQ ID Nos: 1 and 2).

According to one embodiment of the invention, the peptide is capable of testing sera from sows and gilts, boars and barrows, and piglets for PRRSV infection by a screening ELISA, for the evaluation of sera from pre-vaccinated piglets for levels of maternally derived anti-PRRSV antibodies, and for determining the levels of immune responses in vaccinated piglets towards a vaccine employing PRRSV antigenic peptide.

In a specific embodiment, an ELISA immunoassay can be used to test swine blood, serum or plasma samples for the presence of anti-PRRSV antibodies comprising the steps of:
  i. attaching a mixture of two PRRSV NC peptides (SEQ ID Nos: 1 and 2) to a solid support,
  ii. exposing said peptide attached to said solid support to a swine blood, serum or plasma sample containing antibodies, under conditions conducive to binding of the antibody to the peptide, and
  iii. detecting the presence of antibodies bound to said peptide attached to said solid support.

In another specific embodiment, an ELISA immunoassay can be used to test swine blood, serum or plasma samples for the presence of anti-PRRSV antibodies comprising the steps of:
  i. attaching a mixture of two PRRSV NC peptides (SEQ ID Nos:7 and 8), as homologues of SEQ ID NOs: 1 and 2 originated from the European Strain sequence, to a solid support, ii. exposing said peptide attached to said solid support to a swine blood, serum or plasma sample containing antibodies, under conditions conducive to binding of the antibody to the peptide, and iii. detecting the presence of antibodies bound to said peptide attached to said solid support.

In an exemplified use of the subject ELISA kit, a pig serum sample to be tested is diluted in sample diluent and then contacted with one or more of the PRRSV NC peptides described above for a time and under conditions for any antibodies, if present, to bind to the peptide-sensitized solid phase. After removal of unbound material (e.g., by washing with phosphate-buffered-saline), the secondary complex is contacted with labeled antibodies to pig-specific IgG or labeled protein A, protein G, or protein A/G. These antibodies or proteins A, G or A/G bind to the secondary complex to form a tertiary complex and, since the second antibodies or proteins A, or G or A/G are labeled with a reporter molecule, when subjected to a detecting means, the tertiary complex is detected. The reporter molecule can be an enzyme, radioisotope, fluorophore, bioluminescent molecule, chemiluminescent molecule, biotin, avidin, streptavidin or the like. For ELISA the reporter molecule is preferably an enzyme.

Specific embodiments of the present invention include, but are not limited to, the following:

(1) A Porcine Reproductive and Respiratory Syndrome (PRRS) vaccine composition, comprising a peptide antigen and a veterinarily acceptable delivery vehicle or adjuvant, wherein the peptide antigen comprises an amino acid sequence selected from the group consisting of: a) SEQ ID NO: 9, SEQ ID NO: 10, SEQ ID NO: 11, SEQ ID NO: 12, and any combination thereof; b) a homologue of (a); and c) any combination of (a) or (b).

(2) The PRRS vaccine according to (1), wherein the peptide antigen comprises the amino acid sequence of SEQ ID NO: 9.

(3) The PRRS vaccine according to (1), wherein the peptide antigen comprises the amino acid sequence of SEQ ID NO: 10.

(4) The PRRS vaccine according to (1), wherein the peptide antigen comprises the amino acid sequence of SEQ ID NO: 11.

(5) The PRRS vaccine according to (1), wherein the peptide antigen comprises the amino acid sequence of SEQ ID NO: 12.

(6) The PRRS vaccine according to (1), wherein the peptide antigen is altered by adding or deleting 1 to 5 amino acids.

(7) The PRRS vaccine according to (1), further comprising a T helper epitope covalently linked to the amino- or carboxyl-terminus of the peptide antigen.

(8) The PRRS vaccine according to (7), wherein the T helper epitope is SEQ ID NOs: 35.

(9) The PRRS vaccine according to (7), wherein the T helper epitope is covalently linked to the peptide antigen through a spacer comprising an epsilon lysine residue.

(10) The PRRS vaccine according to (9), wherein the spacer is SEQ ID NO: 36.

(11) The PRRS vaccine according to (1), further comprising a T helper epitope that is unlinked to the antigenic peptide, wherein the T helper epitope is selected from the group consisting of SEQ ID NOs: 47-90.

(12) The PRRS vaccine according to (1), wherein the total amount of peptide antigen is between about 10 μg to about 1 mg.

(13) The PRRS vaccine according to (1), wherein the delivery vehicle and adjuvant is selected from a group consisting of Montanide ISA 50V, Polyoxyethylene (20) sorbitan monooleate, and a CpG oligonucleotide.

(14) A method for protecting piglets against PRRS infection, comprising administering a vaccine according to (1).

(15) A PRRS vaccine composition, comprising: a) a peptide antigen and a veterinarily acceptable delivery vehicle or adjuvant, b) a peptide antigen comprising an amino acid sequence selected from the group consisting of SEQ ID Nos: 10, 11, 12, 31, and a combination thereof, and c) a PRRSV Th peptide selected from the group consisting of SEQ ID NOs: 80-90 and a combination thereof.

(16) A PRRS vaccine composition, comprising: a) a peptide antigen and a veterinarily acceptable delivery vehicle or adjuvant, b) a peptide antigen comprising an amino acid sequence selected from the group consisting of SEQ ID Nos: 42, 44, 45, 46, and a combination thereof, and c) a PRRSV Th peptide selected from the group consisting of SEQ ID NOs: 80-90 and a combination thereof.

(17) A method for diagnosing PRRS infection comprising the steps of: a) attaching a mixture of SEQ ID NO: 1 and SEQ ID NO: 2 to a solid support, b) exposing said peptide attached to said solid support to a swine blood, serum or plasma sample containing antibodies, under conditions conducive to binding of the antibody to the peptide, and c) detecting the presence of antibodies bound to said peptide attached to said solid support.

(18) An ELISA immunoassay for testing the presence of anti-PRRSV antibodies comprising the steps of: a) attaching a mixture of SEQ ID NO: 7 and SEQ ID NO: 8 to a solid support, b) exposing said peptide attached to said solid support to a swine blood, serum or plasma sample containing antibodies, under conditions conducive to binding of the antibody to the peptide, and c) detecting the presence of antibodies bound to said peptide attached to said support.

The following examples serve to illustrate the present invention and are not to be used to limit the scope of the invention.

EXAMPLE 1

Serological Assays for Assessment of Immune Sera Titers for Crossreactivity Between the Target PRRSV B Cell Epitope Cluster Peptide Antigens and the Native PRRSV Protein Antigens by Immunofluorescent Assay (IFA) Using PRRSV Co-Transfected HTK Cells Antibodies directed against PRRSV subunit proteins, GP3, GP4 and GP5, can be detected by immunofluoresence using HTK cells co-transfected recombinant vaccinia virus rVVT7 (T7 polymerase recombinant vaccinia virus) with plasmid encoding PRRSV orf3, orf4 and orf5 downstream of a T7 promoter respectively. This method provides for transient expression of these PRRSV proteins in mammalian cells with high-fidelity with its original viral replication. As PRRSV GP3, GP4 and GP5 consist of transmembrane domain and side-chain modification, the best PRRSV protein structure can only be make de novo. Each PRRSV subunit protein, GP2, GP3, GP4 or GP5, was synthesized de novo and the co-transfected HTK cells were used as the target cells for the performance of intracellular staining by the immune sera for assessment in an immunoassay for the presence of specific antibodies against PRRSV. This immunofluoresence assay system allows for the best condition for detection of antibodies to the natural PRRSV antigens with high specificity and sensitivity.

HTK cell line cells were infected with T7 polymerase recombinant vaccinia virus (rVVT7) (21), and co-transfected with the PRRSV-orf3, orf4 and orf5 plasmid by Lipofectamine™ (Invitrogen) (22) according to the mechanism illustrated in FIG. 1A. Specifically, construction of the pRRSV plasmid for expression of the native PRRSV protein mediated by the T7 polymerase promoter was accomplished as follows: A full length pRRSV gene (from Taiwan PRRSV MD001 strain Accession No. AF035409) was amplified by polymerase chain reaction (PCR) and cloned into the pCR2.1Topo® plasmid vector (Invitrogen). The expression ability of the pRRSV plasmid was confirmed by sequencing which shows the full nucleotide sequence for orf3, orf4 and orf5 from PRRSV strain MD001.

HTK cells were grown to 80% confluency in 96-well plates, infected with rVVT7 (22), and then co-transected with the pRRSV orf3, orf4 and orf5 plasmid individually by Lipofectamine™ (Invitrogen). Twenty four hours post co-transfection, the cells were fixed by 80% acetone and the plate preserved at −80° C. for detection of antibodies to PRRSV protein through immunofluorescence assay (IFA).

The illustration in FIG. 1A shows HTK cells infected with T7 polymerase recombinant vaccinia virus (T7/vac) (21) and co-transfected with the pCR-orf5 plasmid by Lipofectamine™ (Invitrogen). The recombinant GP5 protein transports to the cytoplasm after it is translated (22). Anti-GP5 antibodies, according to one embodiment of the invention, become bound to the cytoplasm of the transfected HTK host cells where they are detected by the immunofluorescence of a labeled secondary antibody. This method affords for detection of antibodies to authentic PRRSV GP5 protein with high specificity through transient eukaryotic expression in the HTK cells of full length PRRSV GP5 protein, mediated by the prokaryotic T7 promoter. Similar transfection with pCR-full length PRRSV genome can also be used for detection of PRRSV GP2, GP3, GP4, M and N proteins with high specificity through transient eukaryotic expression in the HTK cells of full length PRRSV genome, mediated by the prokaryotic T7 promoter.

Titration of PRRSV Antibodies by Immunofluorescence Assay (IFA).

Figure 1B:
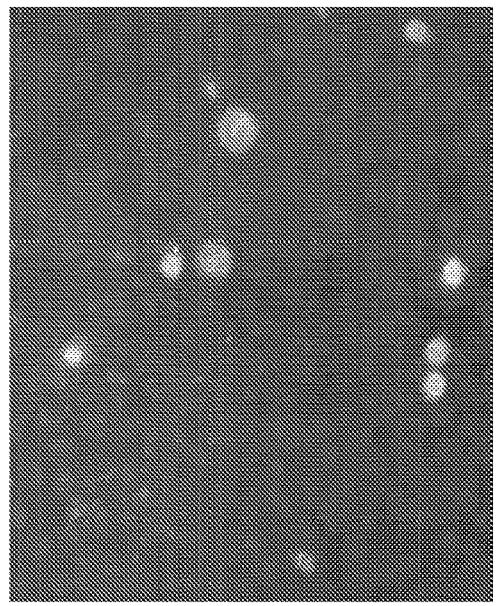
FIG. 1B. Immunofluorescence Assay (IFA) carried out according to the mechanism described in FIG. 1A. Co-transfected HTK cell line cells with antibodies to PRRSV GP5 protein bound to GP5 inside the cytoplasm are detected.

Serum samples were initially diluted 10-fold in PBS followed by a 2-fold dilution series. For each test run, a positive control serum from a PRRSV-infected SPF pig and negative control serum from an uninfected SPF pig were both included to validate the expression of the PRRSV nucleocapsid protein by the pRRSV orf-7 plasmid. Serum samples giving fluorescence signals localized to the cytoplasma (as shown in FIG. 1B) at dilutions higher than 1:10 were scored as having IFA titers>10; and these titers were indicative of animals infected by PRRSV. For sera from animal vaccines containing "target peptide" specific antibodies as a result of vaccination, their crossreactivity against the specific target protein or the full PRRSV genome can be assessed by immunofluorescence assay (IFA) with the corresponding targeted natural PRRSV protein (e.g. GP2, 3, 4 or 5). All testing of serum samples collected from either pigs with natural infection or from pigs given PRRSV peptide-based vaccine were performed under code.

EXAMPLE 2

PRRSV B Cell Epitope Cluster Peptide Antigen Based ELISAs for Immunogenicity Assessment of the Designer Peptides Representing Neutralizing/Receptor Binding Sites of PRRSV The wells of 96-well plates were coated individually for 1 hour at 37° C. with 100 μL of individual target peptides, at 2 μg/mL unless specifically mentioned, in 10 mM NaHCO$_3$ buffer, pH 9.5 unless noted otherwise.

The peptide-coated wells were incubated with 250 μL of 3% by weight of gelatin in PBS in 37° C. for 1 hour to block non-specific protein binding sites, followed by three washes with PBS containing 0.05% by volume of TWEEN® 20 and dried. Pig serum positive for PRRSV antibody by IFA and negative control sera were diluted 1:20, unless otherwise noted, with PBS containing 20% by volume normal goat serum, 1% by weight gelatin and 0.05% by volume TWEEN® 20. One hundred microliters of the diluted specimens were added to each of the wells and allowed to react for 60 minutes at 37° C.

The wells were then washed six times with 0.05% by volume TWEEN® 20 in PBS in order to remove unbound antibodies. Horseradish peroxidase-conjugated goat anti-swine IgG was used as a labeled tracer to bind with the antibody/peptide antigen complex formed in positive wells. One hundred microliters of the peroxidase-labeled goat anti-swine IgG at a pre-titered optimal dilution and in 1% by volume normal goat serum with 0.05% by volume TWEEN® 20 in PBS, was added to each well and incubated at 37° C. for another 30 minutes.

The wells were washed six times with 0.05% by volume TWEEN® 20 in PBS to remove unbound antibody and reacted with 100 μL of the substrate mixture containing 0.04% by weight 3',3',5',5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 μL of 1.0M H$_2$SO$_4$ and absorbance at 450 nm (A$_{450}$) determined.

Serum dilutions were done in accordance with the purpose for detecting PRRSV antibodies in the animal sera: (a) For identification of potential natural infection, a dilution of 1:20 was used, the A$_{450}$ reading was recorded, and a built-in intrinsic negative control for cutoff calculation was used; or (b) For the determination of antibody titers of pigs that received peptide-based PRRSV vaccine formulations, 10-fold serial dilutions of sera from 1:10 to 1:10,000 were tested, and the titer of a tested serum, expressed as Log$_{10}$, was calculated by linear regression analysis of the A$_{450}$.

EXAMPLE 3

Identification of Optimal PRRSV Antigenic Peptides in Diagnostic Application to Differentiate Infected from Vaccinated Animals The genomic sequences of PRRSV from the previously published sequence of PRRSV isolate JXA1, LV, EU, NA and from a Taiwan strain MD001 were used to deduce the protein sequences from open reading frames, and the data obtained from the ORF 2, 3, 4, 5, 6 and 7 encoded protein sequences were used to design B cell epitope cluster antigenic peptides for detection of antibodies in sera from animals with PRRSV infection, and antigenic peptides representing functional neutralizing/receptor binding sites used in marker vaccine formulations for detection of specific antibodies elicited in animals receiving marker vaccine formulations.

We have employed a strategy which uses bioinformatic information and classical immunization experiments to restrict the number of peptides to be screened for identification of optimal B and T cell epitope clustered peptides for diagnostic and vaccine applications.

The development of the urgently needed tools for differentiation of infected from vaccinated animals, termed "DIVA" system, is complementary to the marker vaccine design process.

Since the majority of antibodies produced during PRRSV infection in pigs are specific for the PRRSV ORF 7 encode nucleocapsid protein (NC) protein, for which major antigenic determinants are relatively well conserved among strains from the same continent, the NC protein was therefore targeted as a suitable candidate for the detection of virus-specific antibodies and diagnosis of the infection and disease. The advantage of using synthetic peptide based antigens for antibody capture is well known including improved specificity due to the void of cellular components unrelated to PRRSV causing false positivity, as well as the improved sensitivity due to the epitope cluster peptide's intrinsic nature.

Positive sera from animals with known PRRSV infection were used to screen the overlapping PRRSV ORF 7 encoded NC peptides for strong and consistent antigenicities that could be useful for antibody detection. The negative sera were collected from normal and SPF pigs known to be free of PRRSV infection. Data on epitopes mapping of the NC protein of North American MD001 strain are summarized in FIG. 2. Indirect ELISA using designer peptides for plate coating at 2 ug/mL at 0.1 mL per well was carried out. Two series (a to e) of peptides of increasing length with sequences derived from the MD001 NC protein were synthesized. The 4171 series of peptides (shown in FIG. 2A) were synthesized with the C-terminus beginning at residue 71 while the 4172 series of peptides (shown in FIG. 2B) were synthesized with the C-terminus beginning at residue 123. These peptides were individually used in plate coating and tested with three pooled PRRSV positive sera along with a panel of 12 validated PRRSV negative sera for sensitivity and specificity for each of the peptides.

As shown in FIG. 2A, peptide 4171e (SEQ ID NO:1) was found to be the most antigenic among peptides from this 4171 series tested with an 11mer antigenic epitope having the sequence "PNNNGKQQKKK" (SEQ ID No: 91) located at the N-terminus of peptide 4171e.

As shown in FIG. 2B, peptide 4172e (SEQ ID NO:2) was found to be the most antigenic among the peptides from this 4172 series tested with an 18mer antigenic epitope having the sequence of "EKPHFPLATEDDVRHHFT" (SEQ ID No: 92) located at the N-terminus.

The 18mer antigenic epitope "EKPHFPLATEDDVRHHFT" (SEQ ID No: 92) was not antigenic when presented within peptides 4171a-d. However, this 18mer peptide epitope presents itself within the full-length 4171e molecule (SEQ ID NO:1) to form a large conformational epitope in combination with the 11mer antigenic epitope "PNNNGKQQKKK" on SEQ ID NO: 1. Furthermore, the unexpected immunodominant antigenicity of the two 70 and 73 mer peptides (SEQ ID NO: 1 and 2, respectively) is consistent with the long peptide representing a large exposed surface on the NC protein that presents processions of long continuous and discontinuous epitopes.

Antigenic peptides 4171e (SEQ ID No: 1) and 4172e (SEQ ID No: 2) were employed at a 2:1 ratio mixture for plate coating at 3 ug/mL at 0.1 mL per well which formed a part of the UBI PRRSV NC ELISA for capture/detection of antibodies to PRRSV North American strains.

Homologous NC protein sequences from various PRRSV Strains (MD001, JXA1, NA and EU) were aligned as shown in FIG. 3. Although there are significant substitution, insertion and deletion of amino acid residues for the originating EU sequence when compared to the parent MD001 sequence, substitution peptide homologues (SEQ ID No: 3 and SEQ ID No: 4) as shown in Table 1 based on the amino acid sequence of the PRRSV nucleocapsid protein of the originating European strain, are similarly used as antigens in the UBI PRRSV NC EU ELISA for capture/detection of antibodies to PRRSV European strains.

A panel of 30 sera previously characterized with respect to anti-PRRSV NC protein reactivities by the IFA test was used as a positive sera panel to further validate the sensitivity and specificity of the UBI PRRSV NC ELISA. As shown in Table 2, the UBI PRRSV NC ELISA has about the same level of sensitivity as the IFA test for the NC protein when the limit of detection by IFA was at around 1:16 dilution. The UBI PRRSV NC ELISA test was used as a supplemental serological tool to evaluate field samples and to identify infected and vaccinated animals as well as to evaluate the PRRSV marker peptide based vaccines as described in other examples.

EXAMPLE 4

Design and Synthesis of Peptides for Serological Validation to Identify Antigenic Peptides for Use in a PRRSV Marker Vaccine A large repertoire of PRRSV antigenic peptides representing both PRRSV B and T cell epitope cluster sites from the PRRSV GP2, GP3, GP4, GP5, M and NC proteins with sequences of lengths from about 10 to about 70 amino acids were designed. For some peptides, amino acid substitution at a suitable site was made to allow formation of a cyclic peptide to exert constraint for local structure preservation so as to maximize the cross-reaction with the corresponding native protein. For other antigenic peptides, linkage to an artificial combinatorial Th peptide (e.g. UBITh3, SEQ ID No: 15) was made to enhance their respective immunogenicity. All peptides were subject to a labor intensive and time sensitive "serological validation" process, including iterative cycles of peptide synthesis, vaccine formulation, animal immunization, and serological testing, to yield at candidate peptides for further testing in target animals for respective diagnostic and vaccine that had gone through our initial applications.

All peptides used for immunogenicity testing were synthesized using Applied BioSystems Peptide Synthesizer Models 430A, 431 and 433, using Fmoc chemistry. Each peptide was produced by an independent synthesis on a solid-phase support, with Fmoc protection at the N-terminus and side chain protecting groups of trifunctional amino acids. Completed peptides were cleaved from the solid support and side chain protecting groups removed by 90% trifluoroacetic acid. Synthetic peptide preparations were characterized for correct composition by Matrix-Assisted Laser Desorption Time-Of-Flight (MALDTOF) Mass Spectrometry, and for content including synthesis profile and concentration by Reverse Phase HPLC. With long syntheses, despite the rigorous control of coupling efficiency, peptide analogues were also produced due to events during elongation cycles, including amino acid insertion, deletion, substitution, and premature termination, thus yielding to the generation of multiple peptide analogues along with the targeted peptide. Nonetheless, such peptide analogues were still suitable in peptide preparations as contributors to antigenicity and immunogenicity when used in immunological applications either as an antibody capture antigen for purpose of immunodiagnosis or as an immunogen for purpose of vaccination. Typically, such peptide analogues, either intentionally designed or generated through synthetic process as a mixture of byproducts, are frequently as effective as a purified preparation of the desired peptide, as long as a discerning QC procedure is developed to monitor both the manufacturing process and the product evaluation process to guarantee the reproducibility and efficacy of the final product employing these peptides.

FIG. 4 shows the distribution/localization of selected B and T cell epitopes on the PRRSV 2 to ORF 7 encoded proteins (GP2, GP3, GP4, GP5, M and NC proteins) that had gone through our initial investigation and validation for use in subsequent vaccine formulation applications. The design goal for B cell epitope cluster peptide immunogens is to create the antigenic peptide to mimic the selected functional sites which can induce neutralizing antibodies or are involved with PRRSV receptor binding to target cells. Specific GP5 B cell epitope cluster peptides were designed over four amino acid frames GP5.1, 5.2, 5.3 and 5.4 around the receptor binding/neutralizing site as shown in Table 4 (SEQ ID Nos: 9 to 14) for testing their relative immunogenicity and cross-reactivity to native PRRSV GP5 protein antigen, based on either single PRRSV strain sequence or as a combinatorial sequence, as derived from several PRRSV strain sequences, for breadth of viral coverage.

Additional B cell cluster antigenic peptides designed around neutralizing sites from structure proteins GP2 to GP4 based on the PRRSV JXA1 sequence with designation of GP2 B epitope (V111-L136), GP3 B epitope (C57-C75) and GP4 B epitope (C52-C69) are shown in Table 3. GP2 B (V111-L136) is presented as a linear peptide (SEQ ID NO: 6) while GP3 B epitope (C57-C75) and GP4 B epitope (C52-C69) are presented as cyclic peptides (SEQ ID NOs: 7 and 8) to allow local constraints for conformation preservation. These antigenic peptides were also linked individually to an artificial combinatorial Th peptide (SEQ ID No: 15) either at the C-terminus (SEQ ID Nos: 29 and 30) for GP5.1 and GP5.2 frames or at the N-terminus (SEQ ID Nos: 39-46) as shown in Table 5 to enhance the immunogenicity of these peptide antigens due to their short length nature. These B cell epitope cluster peptide immunogens were incorporated into vaccine formulations, immunized into guinea pigs or pigs according to well-designed protocols with immune sera collected timely for extensive serological assessments. These immune sera were subjected to testing for their antibody titers against the respective target peptide antigen based ELISAs for immunogenicity.

Detection of cross-reactivity to the PRRSV native protein antigens by immunnofluorescence assay (IFA) was carried out as described in Example 1. This is to assess suitability of the designed peptide immunogens for use in the final vaccine formulation. For those peptide antigens qualified as peptide immunogens, peptide homologues with sequences derived from the originating PRRSV strains (e.g. MD001, JXA1, NA and EU strains), or the consensus (cons) sequences as shown in Table 3, or combinatorial sequences as shown in Table 4 for SEQ ID Nos 32, 33 and 34, derived thereof, were further designed as peptide immunogens to allow elicitation of antibodies in the immunized host for broad cross-reactivities with PRRSV of different strains.

The design for T cell epitope cluster peptide immunogen is far simpler. Well characterized immunodominant T cell epitopes based on their ability to induce IFN-gamma responses in culture of peripheral blood mononuclear cells (PBMCs) obtained from PRRSV-immunized and later challenged pigs were selected for incorporation into vaccine formulations to broaden the cell mediated immune response in immunized hosts. The sequences of T cell epitope cluster peptides based on PRRSV JXA1 strain from GP4, GP5, M and NC proteins, and alignments for homologous PRRSV T helper epitope sequences in various PRRSV strains (MD001, NA and EU) are shown in Table 6 as SEQ ID Nos: 47-79. To improve the solubility of these rather hydrophobic peptide antigens, three lysine residues (KKK) were added to the N-terminus of the individual T helper peptide for them to act as peptide immunogens. A pool of these T cell cluster peptides was made by mixing all the identified Th peptide immunogens in equal ratio (SEQ ID Nos: 47-79) as a supplement (T cell epitope pool 1) in vaccine formulations to further enhance the immunogenicity of the PRRSV B cell cluster peptide immunogens and on their own as PRRSV T cell peptide immunogens for cell mediated immunity.

To further broaden the T cell epitope coverage over the animal's diverse genetic background, a combinatorial peptide, based on the four homologous T epitope sequences, for specific epitope is prepared for each of the T cell epitopes. Similarly, three lysine residues (KKK) were added to the N-terminus of the respective combinatorial T epitope cluster peptide immunogens (SEQ ID. NOs: 80-90) as shown in Table 7. A pool of these T epitope cluster combinatorial peptide immunogens (pool 2) was used as a supplement in vaccine formulations to further enhance the immunogenicity of the PRRSV B cell cluster peptide immunogens and on their own as PRRSV T cell peptide immunogens for cell mediated immunity.

EXAMPLE 5

Immunization of Guinea Pigs and Pigs with Vaccine Formulations Containing PRRSV B Epitope Cluster Peptide Antigens from GP5, 2, 3 an 4 Proteins for Assessment of Immunogenicity and Crossreactivities with Native PRRSV Proteins An ectodomain is the domain of a membraneprotein that extends into the extracellular space (the space outside a cell). Ectodomains are usually the part of a viral protein that initiate contact with target cell surface and responsible for attachment to and entry into cells during infection. Viral entry-associated domains are important for the induction of neutralizing antibodies since neutralizing antibodies block interaction of virus with its cellular receptors. When developing a next generation effective PRRSV vaccine, it is thus important to assess the functionality of viral entry-associated domains of PRRSV. The macrophage-specific lectin sialoadhesin (CD163) is a crucial viral receptor on macrophages. Using a soluble form of sialoadhesin, the disulfide linked heterodimer of GP5 and M complex of PRRSV has been found to be the ligand for sialoadhesin. This ligand-receptor interaction is dependent on the lectin activity of sialoadhesin and on sialic acids on the GP5 glycoprotein. The ectodomain of the PRRSV GP5 protein and the impact of M on GP5's immunogenicity was therefore explored to identify the optimal GP5 peptide immunogens for use in the PRRSV marker vaccine formulations with an aim to induce an immunity that blocks the interaction between viral M/GP5 and the host cell receptor sialoadhesin.

Over 45 peptide antigens around the receptor binding/neutralizing sites in the ectodomain of PRRSV GP5 protein were designed and grouped into four amino acid sequence frames for immunogenicity assessment.

The first frame began at the C-terminus residue "E" (glutamic acid) of the GP5 ectodomain and extended all the way to the N-terminus of the ectodomain including five additional amino acid residues into the signal sequence of the GP5 protein to make a 40mer peptide antigen as shown in Table 4 as GP5.1 MD001(A26-E65) peptide antigen (SEQ ID No: 29), based on the sequence of PRRSV strain MD 001. This design allows for a Cys residue in the central part of the GP5 peptide antigen for disulfide bond formation with the ectodomain of M peptide, if desired.

The second domain is an extension of the GP5.1 MD001 (A26-E65) peptide antigen at the N-terminus for another five amino acid residues into the signal sequence resulting in a 45 mer peptide GP5.2 MD001 (V21-E65) (SEQ ID No: 30) where an intramolecular disulfide bond between C24 and C48 could allow preservation of the regional conformation of the ectodomain of GP5. This design would allow the induction of specific antibodies to most of the ectodomain of GP5 in the absence of M protein.

The third frame modeled after the second frame peptide antigen GP5.2 MD001 (V21-E65) with the exception of leaving out the 11mer GP5 HV2 region of the ectodomain to yield at a 34mer peptide antigen GP5.3 (V21-D54) (SEQ ID No: 9). This design would allow B cell recognition of the highly conserved central region of the ectodomain of GP5.

The fourth frame (GP5.4) was directed to a looped structure located at the center of the ectodomain of the GP5 protein to arrive at a 25 mer cyclic peptide GP5.4 (C24-C48) based on the PRRSV strain MD001 sequence. In order to accommodate the strain to strain variation, combinatorial peptides modeled after the peptide antigens of the third and fourth amino acid frames according to the PRRSV strain sequences of JXA1/MD001 and JXA1/NJ-a, of the North American type were designed as GP5.3 JXA1/MD001 (V21-D54) (SEQ ID No: 32), GP5.3 JXA1/NJ-a(V21-D54) (SEQ ID NO: 33) and GP5.4 NJ-a/JXA1/MD001 (C24-C48) (SEQ ID NO:34). In order to assess the impact of the ectodomain of M protein on the GP5 ectocdomain peptide immunogenicity, a 26mer ectodomain peptide with the sequence of the following: "MGSSLDDRCHDSTAPQKV-LLAFSITY" (SEQ ID No: 93) based on MD001 sequence was designed (M1-Y26) for assessment.

The structure of PRRSV consists of a nucleocapsid protein in association with the viral RNA. The nucleoprotein is surrounded by a lipid envelope in which six structure proteins are embedded: the GP2, GP3, GP4, GP5 and the nonglycosylated proteins M and E (ORF2b). GP5 and M are the most abundant proteins in the envelope while the other envelope proteins are present in lower amounts. GP5 has been the major target for PRRSV protective immunity. However, in light of the variability of the PRRSV and the recent findings that GP2 and GP3 are also somewhat involved in clinical and virological protection, whereas documented polyclonal antibodies bound to antigenic peptides derived from GP2, GP3 and GP4 also exerted neutralizing activities against PRRSV, selected peptide antigens from GP2, GP3 and GP4 were also designed, screened and identified for incorporation in PRRSV vaccine formulations. Specifically, antigenic peptides GP2B epitope (V111-L136) (SEQ ID No: 10), GP3 B epitope (C57-C75) (SEQ ID No: 11), GP4 B epitope (C52-C69) (SEQ ID No: 12) as shown in Table 3 were designed based on PRRSV JXA1 strain sequence for immunogenicity and cross-reactivities assessment. Homologous GP5, GP2, GP4 and GP4 derived B epitope sequences from various PRRSV strains are also listed in Table 3 as examples for peptide antigen design references.

These B epitope cluster peptide antigens from GP5, GP2, GP3, and GP4 were also linked individually to an artificial combinatorial Th peptide (SEQ ID No: 35) either at the C-terminus (SEQ ID Nos: 37 and 38) for GP5.1 and GP5.2 frames or at the N-terminus (SEQ ID Nos: 39-46) as shown in Table 5 to enhance the immunogenicity of these peptide antigens overcoming their short length nature.

Vaccine Formulations.

In an exemplified use of peptide based PRRSV vaccine of the invention, vaccine formulations having as immunogens peptides comprising the receptor binding/neutralizing or T helper epitope cluster sites as listed in Tables 3 to 7 with SEQ ID Nos: 9-90, either with or without linkage to a foreign Th epitope through the amino or carboxyl terminus and a Lys-Lys-Lys-εLys (SEQ ID No: 36) or εNLys spacer to a foreign T helper epitope such as the artificial combinatorial Th sequence UBITh® 3(SEQ ID No: 35), were formulated into water-in-oil emulsions using a commercially available oil vaccine delivery vehicle, Montanide ISA 50V2 based on supplier recommended procedures. Montanide™ ISA 50V2 (Seppic, Paris France), an oily adjuvant composition of mannide oleate and mineral oil commonly used for swine vaccines, was emulsified with an equal volume of the aqueous phase peptide solution in PBS. Peptide immunogens were formulated into the respective emulsions at around 25 to 75 ug/mL, according to specific protocols (e.g. peptide ratio and total peptide concentration in the emulsion). The emulsion based vaccine formulations were injected intramuscularly into guinea pigs at 0.25 mL to 0.5 mL per site or into piglets at 1 mL per site, unless specifically mentioned otherwise.

Immunization of Guinea Pig and Piglet with the Designer Peptide Vaccine Formulations.

For immunogenicity studies conducted in Guinea Pigs, adult mature and naïve male and female Duncan-Hartley Guinea Pigs (300-350 g/BW) were used at 3 per group. Animals were immunized with the specific vaccine formulation at 0 and 3 wpi intramuscularly (IM) for 2 doses. The vaccine formulations should be put at room temperature for about 30 min and vortexed for about 10 to 15 seconds prior to immunization. Blood was collected for serum samples at weeks 0, 3 and 5 post initial immunization (wpi). These samples were tested by target peptide based ELISAs for direct binding titers and PRRSV co-transfected cell based IFA for cross-reactivity titers as described in Examples 1 and 2 for immunogenicity assessment of the peptide immunogens and vaccine formulations.

Piglets of approximately 4 weeks of age from a specific pathogen-free (SPF) farm were ear marked for immunogenicity studies and divided into groups (3 to 5 piglets/group) according to study protocol. These groups were immunized with vaccine formulations intramuscularly at weeks 0 and 4. In one study, piglets from a regular farm with prior PRRSV infection were used for assessment of the independent immunogenicity of the designer PRRSV peptide antigens in the presence of anti PRRSV antibodies through the use of a combination of diagnostic ELISA tests to differentiate the infected from marker vaccine formulation of this invention vaccinated pigs and also measuring the pigs' responses to the PRRSV marker vaccine formulations.

Blood samples were collected at the time of first immunization, at 3-4 weeks upon the first boost, and two weeks after the boost at 5-6 weeks, serum samples were prepared and subject to multiple serological tests for assessment of immunogenicity and cross-reactivity as described in details in examples 1 and 2.

Optimization and Ranking of Peptide Immunogens Designed from the PRRSV GP5 Protein Ectodomain Sequences Out of the many GP5 ectodomain peptide immunogens prepared, nine of them were formulated into emulsion formulations for illustration and ranking of their relative immunogenicity after a prime and boost immunization schedule. As can be seen from Table 8, peptide immunogen 4020Kc (SEQ ID No: 38) based on PRRSV MD001 sequence is more immunogenic than peptide immunogen 4020 Kb (SEQ ID No: 37) based both on target peptide ELISA (>1 log 10) and IFA titers. Thus amino acid sequence frame 2 (GP5.2) design is better than frame 1 (GP 5.1). Peptide immunogen 4020Kc was used in most of the PRRSV challenge studies by PRRSV MD001 as described in details in Example 6. As shown in Table 8, peptide immunogen 4048Kb (SEQ ID No:39) designed with frame 3 (GP5.3) with sequence derived from PRRSV MD001 was found having about the same immunogenicity as peptide 4020Kc, however, its IFA titer was higher than that of peptide immunogen 4020Kc. Similar immunogenicity as demonstrated by both ELISA and IFA was found with another peptide immunogen 4050Kb (SEQ ID No:40) designed based on the third frame (GP5.3) when compared to peptide immunogen 4048Kb. Frame 3 was thus considered the more favored design frame for GP5 B cell epitope cluster antigen presentation.

In order to broaden the viral strain coverage, we therefore proceeded to design a few related combinatorial peptide antigens, based on amino acid sequence frame 3, such as peptide immunogen 4052Kb (SEQ ID No:41) and peptide 4124 Kb (SEQ ID No: 42) to test for breadth in antibody reactivity when compared to single sequence GP5 peptides 4048a (SEQ ID No: 9) and 4050a (SEQ ID No: 31). Dual reactivity with MD001 and JXA1 derived GP5.3 frame sequences was found for immune sera derived from immunization with peptide 4052Kb (SEQ ID No: 41) thus demonstrating the breadth of coverage of both MD001 and JXA1. GP5.3 peptide antigens 4124a (SEQ ID No: 30) and 4124Kb (SEQ ID No: 42) were designed to further expand the combinatorial nature of the peptide immunogens and compared for their respective immunogenicity. As shown in Table 8, significant enhancement of immunogenicity, as shown by both ELISA and IFA, was found with peptide 4124Kb when compared to the peptide antigen 4124a showing the immunogenicity enhancing effect of the artificial combinatorial Th peptide (SEQ ID No:35) when linked to the peptide antigen 4124a. Reduction of amino acids at both the N- and C-terminus to retain the looped structure of GP5 had led to the design of peptide antigen 4094a (SEQ ID No: 35) and its more immunogenic form peptide antigen 4094Kb (SEQ ID No:43). Both peptide antigens showed reduced immunogenicity after such sequence trimming, thus the artificially constructed loop structure (C24-C48) remains a critical part of the GP5 ectodomain and enhanced immunogenicity therefrom can be optimally built-in by extending from both the N- and C-termini into the structure of peptide antigen 4124a and 4124Kb.

In all assessments, attachment of artificial combinatorial Th peptide (SEQ ID No:35) to either the C-terminus as shown in the case of peptide antigens 4020b and 4020c, resulting at 4020Kb and 4020Kc, or at the N-terminus such as 4124a resulting at 4124Kb, all facilitated the respective peptide antigen to become a better peptide immunogen. Peptide antigens of the peptide 4094 and 4124 series were made into emulsion vaccine formulations for follow up PRRSV GP5 based challenge study by PRRSV JXA1 strain as described in Example 7 with peptide immunogen 4124Kb demonstrating success in protecting fully (20/20=100%) naïve piglets from infection by the highly pathogenic PRRSV JXA1 strain even with single administration of the emulsion (group 5), while peptide immunogen 4094 series exerted a suboptimal protection (4/5=80%) after two doses of immunizations.

Effect of PRRSV Ectodomain M Peptide on GP5 B Epitope Cluster Peptide Antigen's Immunogenicity.

GP5 and M are the most abundant proteins in the PRRSV envelope and the two proteins form a disulfide linked heterodimer in their ecodomain to act as the ligand to the sialoadhesin receptor (CD163) on the cell surface of the macrophages. The full length M ectodomain peptide antigen (26mer in length) was prepared and mixed at ratios of 1:1 and 1:10 with the full length GP5 ectomain peptide immunogens 4020Kb or 4020Kc to assess the impact of this ectodomain M peptide on the immunogenicity of both GP5 ectodomain peptide antigens 4020Kb and 4020Kc.

As shown in Table 9, the 26mer ectodomain M peptide was found surprisingly immunogenic when mixed at equal ratio with the GP5 peptide immunogen 4020Kb and 4020Kc with the relative immunogenicity of M to GP5 peptide immunogens 4020Kb and 4020Kc ranked at about 1000- and 100-fold respectively as measured by peptide based ELISA (comparison of Groups 1 and 2; of Groups 3, 4 and 5). IFA titers for GP5 peptide immunogen 4020Kc were also significantly suppressed in a dose dependent manner (comparison of Groups 3, 4 and 5). Since the ligand-receptor interaction is dependent on the lectin activity of sialoadhesin on the macrophages and the sialic acids on the GP5 glycoprotein, it is therefore important to preserve the immunogenicity of GP5 to allow elicitation of antibodies to bind to this major protein in the PRRSV envelope. The M peptide, despite the suggested covalent linkage to GP5 on the envelope thus being a part of the GP5/M complex as the ligand, was therefore left out in our follow-up PRRSV vaccine design in the B cell epitope cluster peptide antigen based component.

Effect of Varying Doses of PRRSV Th Pool on the IFA Titers of the PRRSV GP5 B Cell Epitope Cluster Peptide Antigens.

GP5 peptide antigen 4094a representing the central looped structure (C24-C48) of the GP5 ectodomain domain having a suboptimal immunogenicity was used for this study in piglets to explore the effect of varying doses of PRRSV Th peptides on the B cell epitope cluster peptide antigen's immunogenicity. A mixture of PRRSV Th epitope cluster peptides at equal ratio was further supplemented to the 4094a peptide antigen (SEQ ID No: 31) at 5%, 10%, 20% to 50%. The vaccine formulations containing both the B cell epitope cluster antigenic peptides and the T cell epitope cluster peptide antigens were given to piglets through a standard immunization protocol with a prime and a boost protocol at a 30 ug/mL suboptimal dose to monitor the effect of such PRRSV Th peptide on the immunogenicity of peptide antigen 4094a (Group 1 to group 4). Although the immunogenicity as measured by ELISA was not significantly changed for these groups monitored, the IFA titers demonstrated an improvement in the cross-reactivity of the elicited anti-peptide antibodies in these piglets to the native PRRSV GP5 protein in a dose dependent manner. For comparison, the GP5 B cell epitope cluster peptide immunogen 4094Kb (SEQ ID No: 43) with a combinatorial Th epitope covalently linked to the 4094a (Sequence ID No 31) (group 5) was also shown to have improved immunogenicity relative to the peptide antigen 4094a alone. These short PRRSV Th peptides (SEQ ID Nos: 47-79), known to mount cell mediated immunity against PRRSV through a recall response upon exposure to PRRSV after priming the immunized the host, were not covalently linked to the B cell epitope cluster peptide antigen. Improvement of the quality of the antibody reactivity as shown by the improved IFA titers was indicative of the benefit of such a T cell mediated immune response. In order to mount broad based cell mediated immunity including cytokine production against PRRSV upon exposure to PRRSV, these carefully selected PRRSV Th peptides were included in the vaccine formulations along with the PRRSV B cell epitope cluster peptide immunogens at 20% (w/w) in all the follow-up challenge studies.

Identification and Design of Highly Immunogenic GP2, GP3 and GP4 B Cell Cluster Peptides Around Antigenic Sites with Neutralizing Activity.

In light of the recent findings that polyclonal antibodies bound to antigenic peptides derived from the GP2, GP3 and GP4 proteins also exerted neutralizing activities against PRRSV and that these minor proteins of the PRRSV envelope are also somewhat involved in clinical and virological protection against PRRSV, specific antigenic peptides GP2 B epitope (V111-L136) (SEQ ID No: 6), GP3 B epitope (C57-C75) (SEQ ID No: 11), GP4 B epitope (C52-C69) (SEQ ID No: 12 as shown in Table 3 were designed based on PRRSV JXA1 strain sequence and identified as candidate peptide antigens for immunogenicity and cross-reactivities assessment. These B epitope cluster peptide antigens were individually linked to an artificial combinatorial Th peptide (SEQ ID No: 35) at the N-terminus as GP2, 3, and 4 B cell epitope cluster antigenic peptides (SEQ ID Nos. 44-46) for immunogenicity assessment in guinea pigs.

Vaccine formulations containing individually the specifically designed GP2, GP3 and GP4 B Cell Cluster Peptides around the antigenic sites with neutralizing activity, with or without linkage to the artificial combinatorial Th sequence, were tested in guinea pigs for assessment of their respective immunogenicity. Out of the many peptide immunogens designed, the three peptides (SEQ ID Nos: 44, 45, and 46) with artificial combinatorial Th peptide linkage at the N-terminus showed surprisingly high immunogenicity even upon single administration at a 30 ug dose as shown in Table 11. These highly immunogenic peptides are therefore outstanding candidates for incorporation into final formulations for PRRSV vaccine.

Immunogenicity Assessment for the Combined GP2, GP3, GP4 and GP5 Epitope Cluster Peptide Immunogens in Guinea Pigs.

After refinement of the design for each of the B cell epitope cluster peptide antigens derived from PRRSV GP2, 3, 4 and 5 proteins, combinations of these peptides mixed in an equal ratio in a standard emulsion based vaccine formulation at a total peptide concentration of 30 ug/mL for initial priming and 15 ug/mL at 3 wpi for follow-up boost were tested for the individual peptide antigen's immunogenicity when admixed with other peptide antigens, and also to assess the overall immunogenicity of the peptide antigen mixtures to assess and avoid any unintended suppression of the immunogenicity of one or more antigens within the mixture. This assessment was carried out to avoid the negative impact by M peptide on the GP5/M peptide antigen mixture.

As shown in Table 12, when GP4 B epitope cluster peptide antigen (SEQ ID No: 46) was admixed with GP3 B epitope cluster peptide antigen (SEQ ID No: 45) as a GP3/4 combo formulation, and with GP3 (SEQ ID No: 45) and GP 5 (SEQ ID No: 42) as a GP3/4/5 combo formulation, or with GP2 (SEQ ID No: 44) and GP3 (SEQ ID No: 45) as a GP2/3/4 combo formulation, GP4 peptide antigen's immunogenicity judged by target peptide based ELISA remained strong when mixed with GP3 target peptide, but was significantly weakened when presented in a triple peptide antigen mixture. The immunogenicity of GP2 and GP3 epitope cluster peptide antigens remained as immunogenic as single peptide antigen when compared to GP4 peptide antigen. GP2 and GP3 epitope cluster peptide antigens therefore can be used more robustly in any PRRSV peptide antigen mixtures to enhance the breadth of the immune response coverage. Despite the fact that GP2, GP3 and GP4 are minor components on the viral envelope, reasonable IFA titers showing cross-reactivities with the corresponding native PRRSV protein antigens were obtained by peptide antigen mixtures in the absence of the GP5 antigen peptide (e.g. Groups 1, 2 and 4).

EXAMPLE 6

GP5 Derived Peptide Based PRRSV Vaccine, Supplemented with PRRSV Th Epitope Cluster Peptide Antigens, Protected Piglets from Challenge by PRRSV MD001 Strain To prove the efficacy of the PRRSV GP5 B cell Epitope Cluster Peptide Antigens in protecting pigs from PRRSV infection, three consecutive immunization and challenge studies were conducted by Animal Technology Institute, Taiwan (ATIT). In order to objectively evaluate the vaccine formulations produced by the PRRSV GP5 B Epitope Cluster Peptide Antigens, all formulations were coded. The SPF pigs were regularly monitored to ensure freedom from pathogens including Classical Swine Fever, Pseudorabies, Atrophic rhinitis, *Mycoplasma hyopneumoniae*, Foot and Mouth Disease, Swine Dysentery, Scabies, and *Actinobacillus pleuropneumoniae*. All groups from the PRRS 1001S, 1002S and 1003S studies employed GP5 B epitope Cluster Peptide Immunogens 4020Kc (SEQ ID No: 38) and 4052Kb (SEQ ID No: 41) and had minor variations in some formulation parameters. These formulations were considered equivalent with groups 1 and 2 as 4020Kc antigenic peptide and groups 3 and 4 as 4052Kb antigenic peptide derived vaccine formulations. A pooled equal ratio PRRSV Th epitope peptide mixture (SEQ ID Nos: 47, 51, 52, 55, 59, 61, 63, 67, 70, 74, 76 based on JXA1 sequence) was supplemented in the respective vaccine formulations at 10% by weight to further enhance the immunogenicity, through provision of cell-mediated immunity, of the PRRSV GP5 peptide antigens.

In order not to contaminate the Transgenic SPF farm, the studies were conducted at two sites with only the immunization portion being conducted at the Transgenic SPF farm which provided the four week-old SPF pigs for entry into these immunization/challenge studies. This farm is operated by ATIT and located in an isolated area of Hsian Shan, Hsin Chu in the northern part of Taiwan. After completion of the 4 week prime and boost immunization protocol, the SPF pigs were transferred to another well-controlled farm in the southern part of Taiwan for the challenge studies. Since American strains of PRRSV are prevalent in Taiwan, two American strains, MD-001 and AMERVAC-PRRS, were adopted for use in these challenge studies. After virus challenge, the serum samples were collected for IFA and viremia testing. Finally, the animals were euthanized and subjected to gross inspection and pathology examination. The SPF piglets were divided into groups based on study design with 5 animals per group. Blood samples were collected as indicated in Table 13. All serum samples collected were tested by PRRSV-ORF5 IFA test (by rVV-PRRS ORF5 expression method).

Clinical Observation after Injection

All piglets before and after each vaccine administration were subjected to clinical observation for local (including site reactogenicity and allergic response) and systemic (including dyspnea, appetite, diarrhea, cough, CNS/SS, and allergic response) responses. During the study, occasional local site reactogenicity related swelling was found which persisted no more than 3-4 days and returning to normal condition with no further difference observed. There was no systemic adverse response observed for all animals being studied.

Clinical Observation after Virus Challenge

All immunized pigs showed no clinical signs typical of PRRS during the period monitored after receiving the virus challenge.

IFA Detection and Lung Lesion after Immunization and Challenge

Figures 7A, 7B:
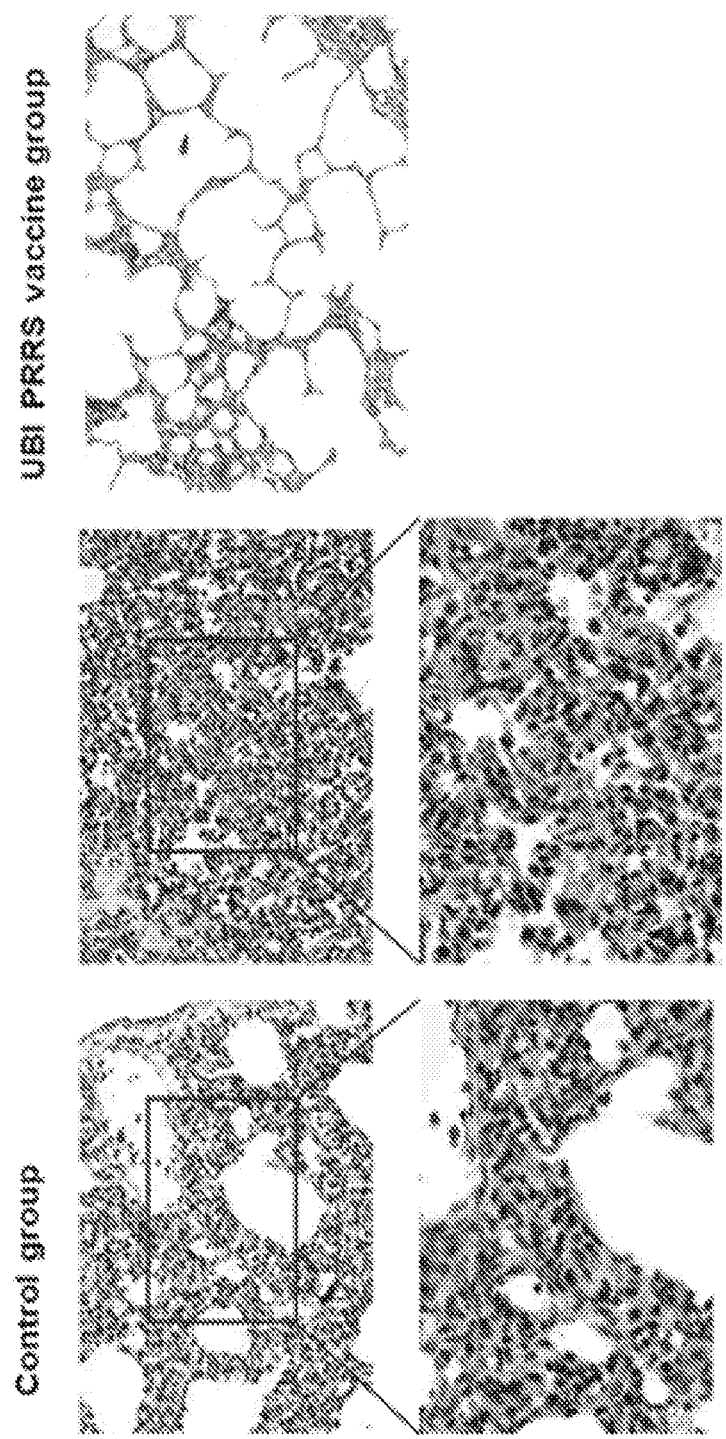
FIG. 7A. Photograph showing histopathological lesions after PRRS virus challenge. Animals from the control group with interstitial pneumonia appeared in lung, thickening of alveoli wall by lymphocytic cells.
FIG. 7B. Photograph showing histopathological lesions after PRRS virus challenge. Animals immunized by UBI PRRS GP5 peptide vaccine formulations. The lung maintains the normal alveoli wall.

The specific antibodies against PRRSV were produced after immunization and reached high titers as detected by IFA at 4 and 6 wpi (weeks post immunization) as shown in Table 14. As shown in Table 14, none of the animals in the control group elicited antibodies to PRRSV GP5 protein even after the PRRSV challenge study, mostly due to the weak immunogenicity nature of the PRRSV GP5 protein when presented in the challenge virus stock. The vaccinated group maintained high IFA titers after virus challenge at 2 wpc (weeks post challenge). Out of the 20 piglets immunized with PRRSV GP 5 B epitope cluster peptide antigen vaccine formulations (4020KC for groups 1 and 2 and 4052Kb for groups 3 and 4) 18 were fully protected (a protection rate of 90%) without any lesion detected. In two of the piglets in groups 3 and 4, slight lesion was detected. In contrast, 80% (4/5) of the pigs were found with severe lesions with interstitial pneumonia as shown in FIGS. 7A and 7B. Based on the extensive challenge testing conducted in the PRRSV laboratory of ATTT, higher IFA titers with PRRSV GP5 protein correlated well with full protection against PRRSV challenges.

Viremia Detection

Using PR-PCR method for PRRSV viral load detection, no detectable viral load was found in all vaccinated pigs. This represents the concordance with the results of protection efficacy in the lung. Although the two virus strains do not cause serious symptoms after infection, the lack of viremia and complete lack of pathological results in the 18/20 vaccinated pigs demonstrated the proven concept of the positive protection efficacy offered by the PRRSV GP5 peptide based vaccine formulations.

EXAMPLE 7

GP5 Derived Peptide Based PRRSV Vaccine, Supplemented with PRRSV Th Epitope Cluster Peptide Antigens, Protected Piglets from Challenge by Highly Pathogenic PRRSV (NVDC-JXA1 Strain) after Both a Single and a Prime-and-Boost Immunization Schedules Background of the China PRRSV JXA1 Challenge Model:

In 2006, there were unparalleled large-scale outbreaks of an initially unknown, but so-called "high fever" disease in China with the essence of PRRS, which spread to more than 10 provinces (autonomous cities or regions) and affected over 2,000,000 pigs with approximately 400,000 fatal cases. Dissimilar from typical PRRS, numerous adult sows were also infected by the "high fever" disease. This atypical PRRS pandemic was initially identified as a hog cholera-like disease manifesting neurological symptoms (e.g., shivering), high fever (40-42° C.), erythematous blanching rash, etc. Autopsies combined with immunological analyses clearly showed that multiple organs were infected by highly pathogenic PRRSVs with severe pathological changes observed. In a concerted effort by Kegong Tian et al, (2007 PLosOne doi: 10.1371/journal.pone.0000526) on Emergence of Fatal PRRSV Variants: Unparalleled Outbreaks of Atypical PRRS in China and Molecular Dissection of the Unique Hallmark, a pig infection model was established in China to reproduce the high pathogenicity of the isolated PRRSV with three representative PRRSV isolates with different origins (JXA1, HEB1, and HUB2) for challenge of 12 SPF-pigs (4 piglets/group).

In each group, two of the piglets were intravenously injected and both died within 6-8 days, implying the high virulence of the tested PRRSV strains. Similarly, the two other piglets in each group were intranasally inoculated, and they developed marked signs of "high fever" disease (e.g., high fever, blood spots, petechiae, shivering, and lamping etc.) within 3-6 days, and both died on day 10 post-infection. Subsequently, viral isolates were successfully recovered from the infected pigs and confirmed by PCR detection and EM. Autopsies were undertaken to evaluate the immunological effects and pathological lesions. Almost the same pathological changes (in lung, heart, brain, kidney, liver, etc.) were observed in pigs killed during the "high fever" epidemic, thus confirmed that the 2006 outbreak of "high fever" disease in China was caused by highly pathogenic PRRSV infection in pig populations. One of the PRRSV isolate JXA1 is now used as the standard virus in a standardized challenge study to validate the protective efficacy of PRRSV vaccines in piglets as per PRC guidelines.

Definition of Valid PRRSV Challenge and Efficacy of Vaccine According to PRC Government Vaccine Product Guidelines:

Four-week old piglets were vaccinated either once or twice with peptide based PRSRV vaccine formulations with a 2-week interval, while one group was kept as non-vaccinated controls. All of them were challenged intramuscularly behind the ear with PRRSV NVDC-JXA1 highly pathogenic virus 3 mL (containing 10E5 TCID50). Body temperature was observed daily for 21 days. The challenge study is considered valid when 5/5 animals become sick upon challenge with fevers and at least 2/5 are dead. Immunized pigs would need to have at least 4/5 remain healthy for the vaccine to be considered protective.

Challenge Study Conducted by UBI in Collaboration with an Animal Health Vaccine Company in Nanking, PRC 2011 with Summary Report:

A total of 35 pigs were screened for seronegativity, with 30 of them being selected for this challenge study according to the guidelines issued by Ministry of Agriculture of PRC as described above. Detailed animal selection, randomization, grouping, immunization and challenge study, temperature observation and record, and mortality are described below:

Healthy piglets at 28-days of age from a farm in Wuxi, Jiangsu province, China were selected. The trial was conducted at a vaccine potency/viral challenge test center in a Nanking based animal health vaccine company. PRRS antibody testing kit (LSI company, France), lot #: 2-VERPRA-001, Exp. 2012-01 and PRRS antigen testing kit: PRRS RT-PCR in-vitro diagnostic kit (NSP2 1594-1680 variant strain) were used to select the PRRSV free animals. PRRS virulent strain (NVCD-JXA1) was used for the challenge test by making 10-times dilution of the stock and administered to the animals at 3 ml per animal.

A total of 35 healthy piglets from the farm were selected for screening, and 30 were enrolled for this study. All selected piglets tested negative for PRRS antigen and antibody in serum. All enrolled piglets were assigned randomly into 6 groups, groups 1-6; with 5 animals per group. Intramuscular injection was placed at a site located directly behind the ear on the side of the pig's neck muscle. The immunization dosages and groups are listed in Table 15 (performed under code so as to be objective).

Group 1 was immunized with PRRSV GP5 peptide (GP5 B epitope cluster peptide antigen 4094 series, SEQ ID No: 43) based vaccine supplemented with a pool of equal ratio PRRSV endogenous T helper epitope peptides (SEQ ID Nos: 47, 51, 52, 55, 59, 61, 63, 67, 70, 74, 76 based on JXA1 sequence) at 20% by weight.

For groups 2 to 5, PRRSV GP5 peptide (GP5 B epitope cluster peptide antigen 4124, SEQ ID No: 42) was used as the immunogen. The final peptide concentration in the vaccine formulation was at 30 ug/mL. This formulation also included a pool of PRRSV endogenous T helper epitope peptides (SEQ ID Nos: 47, 51, 52, 55, 59, 61, 63, 67, 70, 74, 76 based on JXA1 sequence) mixed at an equal ratio and supplemented with the PRRSV B epitope immunogen (SEQ ID No: 42) at 10% (i.e. 27.5 ug B: 2.5 ug T pool), 20% (i.e. 25 ug B: 5 ug T pool) and 50% (i.e. 20 ug B: 10 ug T pool) by weight for groups 2, 3, and 4 respectively. Animals in Group 5 received the same vaccine formulation as group 4 except they were only given a single administration.

Group 6 was the negative control group that was not immunized with any peptide.

The antibody screening results for all 30 piglets initially enrolled in the study are shown in Table 16. The results of all samples from pigs tested for PRRSV antigen by RT-PCR prior to immunization showed 30 out of 30 being negative, while the test kit's positive control found an amplified band of 185 base pairs, which validated the testing system. All animal numbers after randomization are shown in Table 17. Results of PRRSV antibody OD values are shown for day 0 and day 28 post initial immunization in Table 18. Body temperature and mortality after PRRSV JXA1 challenge were observed with temperature (in C) shown in Table 19.

In summary, all piglets in the control group (Group 6) became sick during the first few days of post viral challenge as shown in Table 19, with two dying (2/5=40% mortality rate) as shown in Table 20. The outcome of the control group receiving no vaccination under the challenge study met the validity criteria and guidelines of the challenge study as instituted by Ministry of Agriculture, PRC. In contrast to the control group, the animals in Group 1 were protected with a survival rate of 80% (four out of five animals) and a mortality rate of only 20%. Furthermore, all of the animals (20 out of 20) in Groups 2-5 were protected, thus resulting in a 100% protection.

When combining all 25 animals receiving GP5 B epitope cluster peptide antigen based vaccine formulations as one major study (i.e., Groups 1-5), 24 out of 25 animals survived the challenge by the highly pathogenic PRRSV virus strain JXA1 with only a 4% mortality rate. This result is surprising when compared to the control group where 40% of the pigs died during the early days upon challenge with all five piglets becoming sick thereafter, resulting in a 100% morbidity rate.

EXAMPLE 8

Multi-Component PRRSV Peptide Vaccine to Elicit Broadly Protective Antibodies Against PRRSV PRRSV contains the major glycoprotein, GP5, as well as three other minor glycoproteins, namely, GP2a, GP3, and GP4, on the virion envelope, all of which are required for generation of infectious virions. A strong interaction was found to exist between the GP4 and GP5 proteins, although weak interactions among the other minor envelope glycoproteins (GP2 and GP3) and GP5 have also been detected resulting in the formation of multiprotein complex. Overall, it was concluded that the GP4 protein is critical for mediating interglycoprotein interactions and, along with GP2a, serves as the viral attachment protein, in addition to GP5, that is responsible for mediating interactions with CD163 for virus entry into susceptible host cell.

Due to the high variability of PRRSV, development of a broadly effective PRRSV vaccine will require protection of multiple viral strains. With the already demonstrated protection efficacy of four GP5 based PRRSV vaccine formulations (GP5 B epitope peptide antigen 4020Kc of SEQ ID No: 38, peptide antigen 4052Kb of SEQ ID No: 41, 4094Kb of SEQ ID No: 43 and 4124Kb of SEQ ID No: 42) with the supplement of a pool of endogenous PRRSV Th peptides (SEQ ID Nos: 47, 51, 52, 55, 59, 61, 63, 67, 70, 74, 76 based on JXA1 sequence for pool 1 and SEQ ID Nos: 80-90 for pool 2) as the corner stone of the PRRSV marker vaccine component, it would be highly desirable to incorporate antigenic peptides representing demonstrated functional neutralizing/receptor binding sites in the peptide mixture for elicitation of polyclonal antibodies at the multi-protein receptor complex to allow development of a potent multi-component PRRSV vaccine with broad viral coverage.

With GP2, GP3, and GP4 antigenic peptide binding antibodies showing significant neutralizing property against PRRSV(8), peptide antigens around these selected regions were designed and screened for the most potent peptide immunogen from each of the proteins as shown in Example 5. These peptide immunogens were incorporated in various formulations as multi-component PRRSV peptide vaccines aiming at broad coverage of viral strains. With the availability of sophisticated analytical LC/MS/MS tools and well controlled GMP peptide manufacturing process, a reproducible vaccine formulation, customized for regional use (e.g. North American vs. European), can be rationally developed.

EXAMPLE 9

Application of UBI DIVA System and an Epitope Based Marker Vaccine to Identify PRRSV Infected Animals, Vaccinated but PRRSV Free Animals, or Vaccinated and PRRSV Infected Animals As shown in Example 1, a UBI PRRSV NC ELISA test kit was established by combining two antigenic peptides (4171e, SEQ ID No: 1 and 4172e, SEQ ID No: 2) from the PRRSV nucleocapsid protein as a mixture for plate coating followed by using Protein-HRP conjugate as the tracer for detection of PRRSV infected animals. This test can be used in conjunction with target peptide based ELISAs customized for the monitoring of immunogenicity of an efficacious PRRSV marker peptide vaccine, to form a PRRSV DIVA system for differentiation of infected and vaccinated animals.

Figure 5:
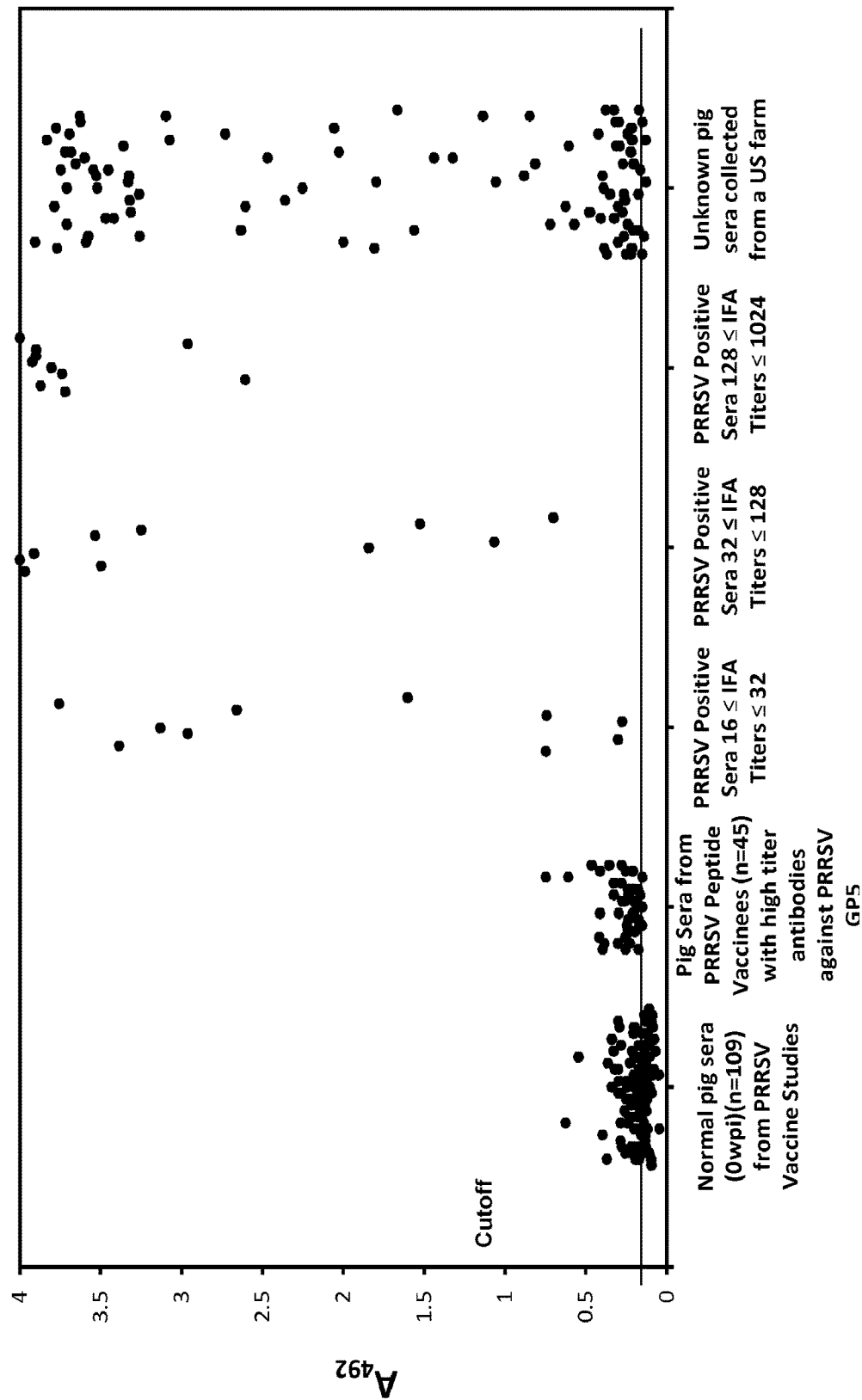
FIG. 5. Seroreactivities of pig sera from different origins tested with UBI PRRSV NC NA ELISA.

As shown in FIG. 5, sera from normal piglets (n=109) known through prior screening to be PRRSV negative before entering the PRRSV vaccine immunogenicity studies, showed a high specificity (109-1/109=99%) with the UBI PRRSV NC ELISA test. Next to this group, sera from pigs (n=45) receiving PRRSV GP5 marker vaccine formulations known to have high titers of antibodies to GP5 as shown by target peptide based ELISA (Log 10 titer>=3) with cross-reactivity to native PRRSV GP5 protein, scored negative by the PRRSV NC ELISA test, demonstrated even further the specificity of the test. The ELISA reading for the three sera groups shown in the middle were from pedigreed IFA positive sera from infected animals. These samples showed increasing ELSIA OD450 nm readings in parallel to IFA titers. Sera from the far right were samples (n=100) collected from a US farm known to have PRRSV infection. A seropositive rate of >56% with the UBI PRRSV NC ELISA was found, indicative of a high prevalence of PRRSV infection in this farm.

When the UBI PRRSV NC ELISA and UBI PRRSV B epitope marker vaccine target peptide based ELISAs were used in combination to monitor the immunogenicity of the PRRSV marker vaccine formulations in a farm in Taiwan known to have PRRSV infection, several pieces of insightful information were obtained.

First, as shown in FIGS. 6A and 6B, all pigs enrolled for the PRRSV vaccine immunogenicity study were found positive with PRRSV NS ELISA with s/c ratios far higher than the cutoff value. Such infection is indicated in the figure highlighted under a grey background as all animals tested were infected. Second, despite the presence of high levels of PRRSV NC reactive antibodies in these piglets, mostly maternally derived (MDA), all peptide based PRRSV vaccine formulations demonstrated significant immunogenicity as detected by the respective target peptide based ELISAs. As shown in FIGS. 6A and 6B where every animal was monitored for its peptide specific antibody titers against component peptide antigens contained in the vaccine formulation received throughout the 0, 4 and 6 weeks period after initial immunization. Amongst the vaccine formulations (GP2+GP3, GP3, GP3+GP4, GP4, or GP5 peptide antigens) each containing a total of 30 ug/mL per dose with a prime and boost at 0 and 4 weeks schedule, independent and high immunogenicity was found to be associated with almost all PRRSV GP2 and GP3 neutralizing site derived peptide vaccine formulations, followed by "GP5 peptide only" vaccine formulations, with GP4 neutralizing site derived peptide antigen showing somewhat compromised immunogenicity when combined with other PRRSV (GP3) peptide antigens.

A combinatorial peptide based PRRSV vaccine incorporating PRRSV B epitope cluster peptide immunogens designed around neutralizing and receptor binding sites from the GP2, GP3, GP4 and GP5 proteins for elicitation of neutralizing antibodies, supplemented by a mixture of endogenous PRRSV T helper peptides to facilitate cell mediated immunity, are being planned for challenge studies by PRRSV MD001 and JXA1 strains, both of the North American type.

EXAMPLE 10

Adoption of UBI's PRRSV Peptide Based Marker Vaccine and its Diagnostic DIVA System for Eradication of PRRSV Infection in a SPF Farm Since the PRRSV B epitope cluster peptide antigens employed in the marker vaccine formulations do not include antigenic peptides from the PRRSV nucleocapsid protein while infected pigs typically develop early antibodies against this major structure protein, it is logical to incorporate PRRSV NC ELISA and PRRSV B epitope marker vaccine target peptide based ELISAs into a diagnostic system for differentiation of infected from vaccinated animals, thus a diagnostic DIVA system.

UBI's PRRSV peptide based marker vaccine can elicit high titers of IFA positive cross-reactive antibodies against the neutralizing and receptor binding sites on the PRRSV proteins. Such marker vaccine formulations can more effectively prevent PRRSV infection than the MLU or viral lysate based PRRSV vaccines due to the very weak immunogenicity nature of these proteins when presented in its current biological vaccine format.

The combined use of UBI's diagnostic DIVA system and its PRRSV marker vaccine will be implemented at a Taiwan SPF farm based on the following strategy to rid of its long term problem with the PRRSV infection. This SPF farm has maintained a rigorous monitoring record for all pathogens and it has only PRRSV infection. The farm cannot eliminate its current PRRSV infection by conventional biological vaccines without incurring significant biosecurity risks. Employing UBI's PRRSV peptide based marker vaccine will not present any such biosecurity risks due to the chemical nature of the vaccine.

Strategy for PRRSV Eradication in a PRRSV Infected SPF Farm.

The farm will maintain a vaccination program with UBI's PRRSV peptide based marker vaccine for at least two years. All pigs inside the farm will be vaccinated using a 0, 4 and 8 weeks immunization schedule and monitored for at least six months. Serum antibody titers against NC and marker vaccine target peptides will be monitored along with the PRRSV viremia level by assays including PRRSV NC ELISA, IFA and quantitative PCR (qPCR). After six months into the vaccination program, piglets born to mothers with vaccination will not receive vaccination and be monitored for 1 to 3 months by the UBI PRRSV NC for rate of infection in these piglets. When all piglets demonstrate negative reactivity with UBI PRRSV NC ELISA, the farm can be considered under control against PRRSV infection. The farm will then retire all pigs with prior PRRSV infection. Until such retirement, all pigs in the farm will be continuously vaccinated by the PRRSV peptide based marker vaccine.

The farm will continue vaccination of all pigs with PRRSV peptide based marker vaccine to enhance the pigs' immunity against PRRSV.

When newly populated piglets and sows are found PRRSV free based on their sera's negative reactivity with PRRSV NC ELISA, the farm can be declared PRRSV free, thus success of the PRRSV eradication program.

Indicators for Use in Monitoring:

UBI's PRRSV NC ELISA and PRRSV marker vaccine target peptide based ELISAs, thus the DIVA, can be used to monitor sera from all animals in the farm for reactivity consistency. Percent positive rate and Mean OD values derived from the PRRSV NC ELISA are recorded during the period of vaccination and monitoring.

Piglets less than one month old which may have maternal antibodies against PRRSV NC protein, thus showing as positives with PRRSV NC ELISA, will decrease with time. When there is no PRRSV in circulation in the environment, i.e. no new infection, these piglets will also become PRRSV free. The farm will accelerate to retire the PRRSV infected sows. Being treated with PRRSV marker peptide vaccine will further reduce the residual risk for the release of PRRSV into the environment from previously infected sows, thus allowing the whole farm to reach PRRSV free status. Table 21 sets the sample size requirement for such testing, at a 95% confidence level, for the probability of detecting one PRRSV positive pig.

Pilot PRRSV Clearance Study Employing DIVA and Multi-Component PRRSV Peptide Immunogen Based Vaccine Formulations:

A pilot PRRSV clearance study, monitored by serological means through DIVA, was executed in a regular PRRSV infected farm by employing water-in-oil (ISA 50) emulsion based vaccine formulations containing multi-component PRRSV peptide immunogens to assess the potential for negative seroconversion for PRRSV NC antibodies by those receiving such multi-component PRRSV peptide immunogen based vaccine formulations.

More specifically, a total of 15 piglets at 4 weeks of age, which tested positive by PRRSV NC ELISA, were put into five experimental groups for the study. The piglets were immunized based on a 0, 4, 8 weeks immunization and bleeding schedule and monitored for a 13 weeks-period from date of the initial immunization. PRRSV B peptide immunogens from GP5 (SEQ ID No: 42), GP2 (SEQ ID No: 44), GP3 (SEQ ID No: 45) and GP4 (SEQ ID No: 46) were mixed in various combinations (e.g. GP5, GP2, GP3, and GP4 for groups 1 and 2; GP5, GP3 and GP4 for group 3; GP3 and GP4 for group 4) at an equal ratio at a total of 25 ug/mL per dose for PRRSV B peptide immunogens. The formulations were further supplemented with 20% by weight (i.e. 5 ug/mL per dose) of PRRSV Th peptides (SEQ ID. Nos: 47, 51, 52, 55, 59, 61, 63, 67, 70, 74, and 76 mixed also at an equal ratio) for group 2, and PRRSV Th combinatorial peptides (SEQ ID NOs: 80-90) for groups 1, 3 and 4. Serum antibody reactivities against NC were monitored by PRRSV NC ELISA to determine PRRSV infection, while serum antibody titers against PRRSV marker peptide vaccine B epitope components were monitored by corresponding PRRSV GP2, GP3, GP4 and GP5 peptide based ELISAs for immunogenicity offered by the various vaccine formulations. Animals in group 5 received no PRRSV peptide based vaccine formulation and served as a negative control group.

All of the pigs from groups 1 to 4 developed antibodies against their respective marker vaccine target PRRSV B GP2, GP3, GP4 and GP5 peptides, as detected by respective PRRSV peptide based ELISAs with specific antibody titers higher than 3 $\text{Log}_{10}$ after a second immunization at 4 weeks from initial immunization and remain high throughout the 13 weeks period monitored. However, antibody reactivities against PRRSV NC protein increased to peak reactivities at around 6 to 8 weeks after initial immunization and then declined to near baseline by 10 weeks after initial immunization and remained at the baseline at 13 weeks after initial immunization during the monitoring period as shown in Table 22.

In contrast, sera from animals in group 5 receiving no vaccine formulation containing PRRSV peptide based immunogens all maintained high reactivities with the PRRSV NC protein. Since antibody to PRRSV NC protein is known to present in infected pigs, the surprising finding of such negative seroconversion for PRRSV NC in pigs vaccinated with the multi-component PRRSV peptide immunogen based vaccine formulations further validated the efficacy of the multi-component PRRSV peptide based vaccine formulations. The application of DIVA and the multi-component PRRSV peptide immunogen based vaccine formulations thus have wide applications and serve an urgent need for monitoring, prevention, clearance and eradication of PRRSV infection.

TABLE 1

Antigenic Peptide from PRRSV Nucleocapsid Protein (NA and EU strains) for detection of Antibodies in infected pigs

| Peptide code | Seq. ID No. | Peptide sequence |
| --- | --- | --- |
| 4171e | 1 | PRRSV peptide P2-E71 from Nucleocapsid Protein (North American strain/MD001/TW/AAC98536) PNNNGKQQKKKKGDGQPVNQLCQMLGKIIAQQSQSRVKGPGRKNKKK NPEKPHFPLATEDDVRHHFTPSE |
| 4172e | 2 | PRRSV peptide E51-A123 from Nucleocapsid Protein (North American strain/MD001/TW/AAC98536) EKPHFPLATEDDVRHHFTPSERQLCLSSIQTAFNQGAGTCILSDSGRI SYTVEFSLPTHHTVRLIRVTAPPSA |
| 4173e | 7 | PRRSV peptide A2-E72 from Nucleocapsid Protein (European strain/08V204/Belgium/EU/GU737266) AGRNRSQKKKKNPAPMGNDQPVNQLCQLLGAMMKSRRQQPRGGQAKKR KPEKPHFPLAAEDDVRHHLTQTE |
| 4174e | 8 | PRRSV peptide P51-N128 of Nucleocapsid Protein (European strain/08V204/Belgium/EU/GU737266) PEKPHFPLAAEDDVRHHLTQTERSLCLQSIQTAFNQGAGVASLSSSGK VSFQVEFMLPVAHTVRLIRVTSTSASQDAN |

TABLE 2

Serological Validation of PRRSV NC ELISA by Pedigreed PRRSV Serum Samples

| Swine ID# | PRRSV IFA Titers | UBI PRRSV N ELISA A450 |
| --- | --- | --- |
| 146 | 16 | 0.747 |
| 159 | 32 | 3.385 |
| 160 | 32 | 0.299 |
| 184 | 32 | 2.962 |
| 185 | 32 | 3.132 |
| 229 | 16 | 0.273 |
| 261 | 16 | 0.741 |
| 211 | 32 | 2.659 |
| 213 | 32 | 3.755 |
| 246 | 32 | 1.603 |
| 242 | 128 | 3.968 |
| 248 | 128 | 3.497 |

TABLE 2-continued

Serological Validation of PRRSV NC ELISA by Pedigreed PRRSV Serum Samples

| Swine ID# | PRRSV IFA Titers | UBI PRRSV N ELISA A450 |
|---|---|---|
| 249 | 128 | 4.000 |
| 250 | 128 | 3.912 |
| 254 | 128 | 1.841 |
| 130 | 128 | 1.067 |
| 134 | 128 | 3.532 |
| 135 | 128 | 3.246 |
| 136 | 128 | 1.526 |
| 138 | 128 | 0.699 |
| 289 | 1024 | 3.717 |
| 290 | 1024 | 3.870 |
| 291 | 1024 | 2.605 |
| 292 | 1024 | 3.738 |
| 293 | 1024 | 3.803 |
| 294 | 1024 | 3.923 |
| 295 | 1024 | 3.901 |
| 296 | 1024 | 3.898 |
| 297 | 1024 | 2.963 |
| 298 | 1024 | 4.000 |
| Negative 01 | <10 | 0.172 |
| Negative 02 | <10 | 0.151 |
| Negative 03 | <10 | 0.214 |
| Negative 04 | <10 | 0.095 |
| Negative 05 | <10 | 0.096 |
| Negative 06 | <10 | 0.111 |
| Negative 07 | <10 | 0.131 |
| Negative 08 | <10 | 0.137 |
| Negative 09 | <10 | 0.132 |
| Negative 10 | <10 | 0.199 |
| Negative 11 | <10 | 0.142 |
| Negative 12 | <10 | 0.211 |

A panel including 3 pooled and 30 individual PRRSV IFA positive (IFA titer >1:16) swine sera and 12 PRRSV IFA negative (titer <1:10) swine sera was used for serological validation of the PRRSV N [p4171e + 4172e] peptide-based ELISA. Sera were diluted 1:21 for ELISA testing.

TABLE 3

Alignments for homologous GP5, GP2, GP3 and GP4 derived B epitope sequences from various PRRSV strains GP5.3 B epitope: (V21-E65)

| | |
|---|---|
| MD001 | VPFCLAALVSAN--GNSSSHSQLIYNLTLCELNGTD (Seq ID No. 9) |
| JXA1 | VPFYLAVLVNAS--NNNSSHIQLIYNLTLCELNGTD (Seq ID No. 13) |
| NA | VPFCFAVLANAS--NDSSSHLQLIYNLTLCELNGTD (Seq ID No. 14) |
| EU | FSLCIGLSWSFADGNGNSSTYQYIYNLTICELNGTT (Seq ID No. 15) |
| Cons | VPFCLAVLVSASDGNNNSSHIQLIYNLTLCELNGTD (Seq ID No. 16) |

GP2 B epitope: (V111-L136)

| | |
|---|---|
| JXA1 | VSRRMYRIMEKAGQAAWKQVVSEATL (Seq ID No. 10) |
| MD001 | VSRRMYRIMEKAGQAAWKQVVNEATL (Seq ID No. 17) |
| NA | VSRRMYRIMEKAGQAAWKQVVSEATL (Seq ID No. 18) |
| EU | VSRRIYQTMEHSGQAAWKQVVSEATL (Seq ID No. 19) |
| Cons | VSRRMYRIMEKAGQAAWKQVVSEATL (Seq ID No. 20) |

GP3 B epitope: (C57-C75)

| | |
|---|---|
| JXA1 | CPTRQAAAEILEPGKSFWC (Seq ID No. 11) |
| MD001 | CLTRQAAAQLYEPSRSLWC (Seq ID No. 21) |
| NA | CLTRQAATEIYEPGRSLWC (Seq ID No. 22) |
| EU | CLTSQAAKQRLEPGRNMWC (Seq ID No. 23) |
| Cons | CLTRQAAAEILEPGRSLWC (Seq ID No. 24) |

GP4 B epitope: (C52-C69)

| | |
|---|---|
| JXA1 | CLRHGDSSSPTIRKSSQC (Seq ID No. 12) |
| MD001 | CLRHGNPSSEAIRKIPQC (Seq ID No. 25) |
| NA | CLRHRDSASEAIRKIPQC (Seq ID No. 26) |
| EU | CLRPYRTNTTQGKVPSQC (Seq ID No. 27) |
| Cons | CLRPGDSSSEAIRKISQC (Seq ID No. 28) |

TABLE 4

PRRSV GP5 ectodomain derived peptides employed for B cell epitope optimization based on four sequence frames (GP5.1 to GP5.4)

| Seq. ID No. | UBI PRRSV epitope description | Combinatorial Peptide Sequence |
|---|---|---|
| 29. | GP5.1 MD001(A26-E65) | AALVSANGNSSSHSQLIYNLTLCELNGTDWLAKKFDWAVE |
| 30. | GP5.2 MD001(V21-E65) | VPFCLAALVSANGNSSSHSQLIYNLTLCELNGTDWLAKKFDWAVE |
| 9. | GP5.3 MD001(V21-D54) | VPFCLAALVSANGNSSSYSQLIYNLTLCELNGTD |
| 31. | GP5.3 JXA1(V21-D54) | VPFCLAVLVNASNNNSSHIQLIYNLTLCELNGTD |
| 32. | GP5.3 JXA1/MD001 (V21-D54) | VPFCLAVLVNASNNNSSHIQLIYNLTLCELNGTD<br>      A  S NG S   YS |
| 33. | GP5.3 JXA1/NJ-a (V21-D54) | VPFCLAVLVNASNNNSSHIQLIYNLTLCELNGTD<br>    F A AS NGDS   YL<br>                 S |
| 34. | GP5.4 NJ-a/JXA/MD001 (C24-C48) | CFAALANASNDSSSHLQLIYNLTLC<br> L V VS NGNN   YI<br>             S |

TABLE 5

B cell epitope cluster peptides derived from PRRSV GP5, GP2, GP3 and GP4 proteins linked through spacer to artificial combinatorial Th peptide (UBITh3) for enhancement of respective peptide's immunogenicity.
Artificial combinatorial Th peptide (Seq. ID NO.: 35): ISISEIKGVIVHKIETILF
                          T   RT   TR
Spacer Sequence (Seq. ID No.: 36): KKK-εK

| Peptide code | Seq. ID No. | Peptide sequence |
|---|---|---|
| p4020kb (GP5.1) | 37 | AALVSANGNSSSHSQLIYNLTLCELNGTDWLAKKFDWAVE-εK-KKK-ISISEIKGVIVHKIETILF<br>                                                                     T   RT   TR |
| p4020kb (GP5.2) | 38 | VPFCLAALVSANGNSSSHSQLIYNLTLCELNGTDWLAKKFDWAVE-εK-KKK-ISISEIKGVIVHKIETILF<br>                                                                           T   RT   TR |
| p4048kb (GP5.3) | 39 | ISISEIKGVIVHKIETILF-KKK-εK-VPFCLAALVSANGNSSSYSQLIYNLTLCELNGTD<br>    T   RT   TR |
| p4050kb (GP5.3) | 40 | ISISEIKGVIVHKIETILF-KKK-εK-VPFCLAVLVNASNNNSSHIQLIYNLTLCELNGTD<br>    T   RT   TR |
| p4052kb (GP5.3) | 41 | ISISEIKGVIVHKIETILF-KKK-εK-VPFCLAVLVNASNNNSSHIQLIYNLTLCELNGTD<br>    T   RT   TR        A  S NG S   YS |
| p4124kb (GP5.3) | 42 | ISISEIKGVIVHKIETILF-KKK-εK-VPFCLAVLVNASNNNSSHIQLIYNLTLCELNGTD<br>    T   RT   TR      F A AS NGDS   YL<br>                                                      S |
| p4094Kb | 43 | ISISEIKGVIVHKIETILF-KKK-εK-CFAALANASNDSSSHLQLIYNLTLC<br>                                  L V VS NGNN   YI<br>                                            S |
| p4148kb (GP2B) | 44 | ISISEIKGVIVHKIETILF-εK-VSRRMYRIMEKAGQAAWKQVVSEATL<br>    T   RT   TR |
| p4151kb (GP3B) | 45 | ISISEIKGVIVHKIETILF-εK-CPTRQAAAEILEPGKSFWC<br>    T   RT   TR |
| P4152kb (GP4B) | 46 | ISISEIKGVIVHKIETILF-εK-<u>C</u>LRHGDSSSPTIRKSSQ<u>C</u><br>    T   RT   TR |

TABLE 6

Alignments for homologous PRRSV T helper epitope sequences from GP4, GP5, M and NC proteins in various PRRSV strains

| GP4 T1 epitope(F7-L15) | | | GP6 T3 epitope(F57-V71) | | |
|---|---|---|---|---|---|
| JXA1 | FLLVGFKCF | (Seq ID No. 47) | JXA1 | FGYMTFVHFESTNRV | (Seq ID No. 63) |
| MD001 | FLLVGFKCL | (Seq ID No. 48) | MD001 | FGYMTFTHFQSTNRV | (Seq ID No. 64) |
| NA | FLVVGFKCL | (Seq ID No. 49) | NA | FGYMTFAHFQSTNKV | (Seq ID No. 65) |
| EU | FLLAGAQHL | (Seq ID No. 50) | EU | FGYMTYVHFESTNRV | (Seq ID No. 66) |

| GP4 T2 epitope(C170-I178) | | | GP6 T4 epitope(R93-K107) | | |
|---|---|---|---|---|---|
| JXA1 | CLFAILLAI | (Seq ID No. 51) | JXA1 | KFITSRCRLCLLGRK | (Seq ID No. 67) |
| MD001 | CLFAILLAI | (Seq ID No. 51) | MD001 | RFITSRCRLCLLGRK | (Seq ID No. 68) |
| NA | CLFAILLAI | (Seq ID No. 51) | NA | KFITSRCRLCLLGRK | (Seq ID No. 67) |
| EU | CLFAILLAI | (Seq ID No. 51) | EU | KFVTSRCRLCCLGRR | (Seq ID No. 69) |

| GP5 T1 epitopes(L117-C131) | | | GP7 T1 epitope(G40-L57) | | |
|---|---|---|---|---|---|
| JXA1 | LAALICFVIRLAKNC | (Seq ID No. 52) | JXA1 | GPGKKNRKKNPEKPHFPL | (Seq ID No. 70) |
| MD001 | LAALICFVIRLAKNC | (Seq ID No. 52) | MD001 | GPGRKNKKKNPEKPHFPL | (Seq ID No. 71) |
| NA | LAALTCFVIRFAKNC | (Seq ID No. 53) | NA | GPGKKNKKKNPEKPHFPL | (Seq ID No. 72) |
| EU | FAAFVCFAIRATKNC | (Seq ID No. 54) | EU | PRGGQAKKRKPEKPHFPL | (Seq ID No. 73) |

| GP5 T2 epitope(K149-K163) | | | GP7 T2 epitope(V63-E71) | | |
|---|---|---|---|---|---|
| JXA1 | KGRLYRWRSPVIVEK | (Seq ID No. 55) | JXA1 | VRHHFTPSE | (Seq ID No. 74) |
| MD001 | KGRIYRWRSPVIIEK | (Seq ID No. 56) | MD001 | VRHHFTPSE | (Seq ID No. 74) |
| NA | KGRLYRWRSPVIIEK | (Seq ID No. 57) | NA | VRHHFTPSE | (Seq ID No. 74) |
| EU | RGRIHRWKSPIVIEK | (Seq ID No. 58) | EU | VRHHLTQTE | (Seq ID No. 75) |

| GP6 T1 epitope(C9-S23) | | | GP7 T3 epitope(S105-A123) | | |
|---|---|---|---|---|---|
| JXA1 | CNDSTAPQKVLLAFS | (Seq ID No. 59) | JXA1 | SLPTQHTVRLIRATASPSA | (Seq ID No. 76) |
| MD001 | CHDSTAPQKVLLAFS | (Seq ID No. 59) | MD001 | SLPTHHTVRLIRVTAPPSA | (Seq ID No. 77) |
| NA | CHDSTAPQKVLLAFS | (Seq ID No. 59) | NA | SLPTHHTVRLIRVTASPSA | (Seq ID No. 78) |
| EU | CHDPTAAQKLVLAFS | (Seq ID No. 60) | EU | MLPVAHTVRLIRVTSTSSA | (Seq ID No. 79) |

| GP6 T2 epitope(A33-L47) | | |
|---|---|---|
| JXA1 | ALKVSRGRLLGLLHL | (Seq ID No. 61) |
| MD001 | ALKVSRGRLLGLLHL | (Seq ID No. 61) |
| NA | ALKVSRGRLLGLLHL | (Seq ID No. 61) |
| EU | ALKVSRGRLLGLLHI | (Seq ID No. 62) |

TABLE 7

T helper epitope cluster peptides derived from PRRSV GP4, GP5, M and NC proteins

| Seq. ID No. | UBI PRRSV Th epitope description | Combinatorial Peptide Sequence |
|---|---|---|
| 80 | GP4 Th1 MD001(F7-L15) | KKK-FLLVGFKCL<br>      IV   R I |
| 81 | GP4 Th2 MD001(C170-I178) | KKK-CLFAILLAI<br>      I L  II L |
| 82 | GP5 Th1 JAX1(L117-C131) | KKK-LAALICFVIRLAKNC<br>      I  IL    KI R |
| 83 | GP5 Th2 MD001(K149-K163) | KKK-KGRIYRWRSPVIIEK<br>      R KL K K    LL R |
| 84 | M Th1 Cons. JXA1(C9-S23) | KKK-CNDSTAPQKVLLAFS<br>        H    F I<br>        Y    E |
| 85 | M Th2 Cons. JXA1(A33-L47) | KKK-ALKVSRGRLLGLLHL |
| 86 | M Th3 Cons. JXA1(F57-V71) | KKK-FGYMTFVHFESTNRV<br>        CA LQ   K<br>        T  N<br>        F<br>        M |
| 87 | M Th4 Cons. JXA1(K93-K107) | KKK-KFITSRCRLCLLGRK<br>      R        R |
| 88 | NC Th1 MD001/Lena (G40→L57) | KKK-GPGRKNKKKNPEKPHFPL<br>      P   GQA   K |
| 89 | NC Th2 Eu/Lena (V63→E71) | KKK-VRHHFTPSE<br>      L GT |
| 90 | NC Th3 MD001/Lena (S105→A123) | KKK-SLPTHHTVRLIRVTAPPSA<br>      N V        ST A |

TABLE 8

Optimization of Peptide Immunogens from PRRSV GP5 Protein

| | | | 0 wpi | | 5 wpi | |
|---|---|---|---|---|---|---|
| | Immunogen description | Animal No. | GP5.1 Peptide ELISA $A_{450}$@1:100 4020b (SEQ ID No. 29) | IFA Titer | GP5.1 Peptide ELISA $Log_{10}$ Titer 4020b | IFA Titer |
| Grp 1 | Peptide 4020Kb = Peptide Immunogen 4020b (MD001)-KKK-εK-UBITh3 SEQ ID No. 37 and PRRSV Th Pool 1 | D1-1<br>G1-2<br>G1-3 | 0.095<br>0.103<br>0.090 | <10 | 3.100<br>3.561<br>2.882 | <50 |

| | | | 0 wpi | | 5 wpi | |
|---|---|---|---|---|---|---|
| | Immunogen description | Animal No. | GP5.2 Peptide ELISA $A_{450}$@1:100 4020c (SEQ ID No. 30) | IFA Titer | GP5.2 Peptide ELISA $Log_{10}$ Titer 4020c | IFA Titer |
| Grp 2 | Peptide 4020Kc = Peptide Immunogen 4020c (MD001)-KKK-εK-UBITh3 SEQ ID No. 38 and PRRSV Th Pool 1 | G51<br>G52<br>G53 | 0.097<br>0.101<br>0.096 | <10 | 4.764<br>4.561<br>3.753 | <50<br>50<br>50 |

TABLE 8-continued

Optimization of Peptide Immunogens from PRRSV GP5 Protein

| | Immunogen description | Animal No. | GP5.3 Peptide ELISA $A_{450}$@1:100 4048a (SEQ ID No. 9) | IFA Titer | GP5.3 Peptide ELISA ELISA $Log_{10}$ Titer 4048a | IFA Titer |
|---|---|---|---|---|---|---|
| | | | 0 wpi | | 5 wpi | |
| Grp 3 | Peptide 4048Kb = Peptide Immunogen UBITh3-ε-KKKK-4048a (MDOO1/Taiwan) SEQ ID No. 39 and PRRSV Th Pool 1 | 7 | 0.079 | <10 | 4.571 | 50 |
| | | 8 | 0.071 | | 4.299 | 100 |
| | | 9 | 0.099 | | 3.151 | 100 |

| | Immunogen description | Animal No. | GP5.3 Peptide ELISA $A_{450}$@1:100 4050a (SEQ ID No. 31) | IFA Titer | GP5.3 Peptide ELISA ELISA $Log_{10}$ Titer 4050a | IFA Titer |
|---|---|---|---|---|---|---|
| | | | 0 wpi | | 5 wpi | |
| Grp 4 | Peptide 4050Kb = Peptide Immunogen UBITh3-εK-KKK-4050a (JXAI/Beijing) SEQ ID No. 40 and PRRSV Th Pool 1 | 16 | 0.071 | <10 | 4.571 | 50 |
| | | 17 | 0.070 | | 4.299 | 100 |
| | | 18 | 0.099 | | 3.151 | 100 |

| | | | 0 wpi | | | 5 wpi | | |
|---|---|---|---|---|---|---|---|---|
| | | | GP5.3 Peptide ELISA $A_{450}$@1:100 | | | GP5.3 Peptide ELISA ELISA $Log_{10}$ Titer | | |
| | Immunogen description | Animal No. | 4048a | 4050a | IFA Titer | 4048a | 4050a | IFA Titer |
| Grp 5 | Peptide 4052Kb = Peptide Immunogen UBITh3-εK-KKK-4052a (Consensies JXAI/MDOO1) SEQ ID No. 41 and PRRSV Th Pool 1 | 25 | 0.055 | 0.061 | <10 | 2.888 | 2.351 | 50 |
| | | 26 | 0.103 | 0.068 | | 4.695 | 4.080 | 100 |
| | | 27 | 0.051 | 0.055 | | 4.376 | 3.620 | 100 |

| | Immunogen description | Animal No. | GP5.3 Peptide ELISA $A_{450}$@1:100 4124a (SEQ ID No. 33) | IFA Titer | GP5.3 Peptide ELISA ELISA $Log_{10}$ Titer 4124a | IFA Titer |
|---|---|---|---|---|---|---|
| | | | 0 wpi | | 5 wpi | |
| Grp 6 | Peptide 4124a (JXAI/MDOO1/NJ-a) SEQ ID No. 33 and PRRSV Th Pool 1 | 3908 | 0.056 | <10 | 4.647 | 80 |
| | | 3909 | 0.057 | | 3.324 | |
| | | 3910 | 0.057 | | 3.986 | |

| | Immunogen description | Animal No. | GP5.3 Peptide ELISA $A_{450}$@1:100 4124a | IFA Titer | GP5.3 Peptide ELISA ELISA $Log_{10}$ Titer 4124a | IFA Titer |
|---|---|---|---|---|---|---|
| | | | 0 wpi | | 5 wpi | |
| Grp 7 | Peptide 4124Kb = Peptide Immunogen UBITh3-εK-KKK-4124a (JXAI/MDOO1/NJ-a) SEQ ID No. 42 and PRRSV Th Pool 1 | 3912 | 0.052 | <10 | 4.132 | 320 |
| | | 3913 | 0.051 | | 4.362 | |
| | | 3914 | 0.052 | | 4.247 | |

| | Immunogen description | Animal No. | GP5.4 Peptide ELISA $A_{450}$@1:100 4094a | IFA Titer | GP5.4 Peptide ELISA ELISA $Log_{10}$ Titer 4094a | IFA Titer |
|---|---|---|---|---|---|---|
| | | | 0 wpi | | 5 wpi | |
| Grp 8 | Peptide 4094a (JXAI/MDOO1/NJ-a) SEQ ID No. 34 and PRRSV Th Pool 1 | 302 | 0.145 | <10 | 2.548 | 80 |
| | | 315 | 0.121 | | 2.919 | |
| | | 330 | 0.212 | | 2.695 | |

TABLE 8-continued

Optimization of Peptide Immunogens from PRRSV GP5 Protein

|   | Immunogen description | Animal No. | 0 wpi GP5.4 Peptide ELISA $A_{450}$@1:100 4094a | 0 wpi IFA Titer | 5 wpi GP5.4 Peptide ELISA $\text{Log}_{10}$ Titer 4094a | 5 wpi IFA Titer |
|---|---|---|---|---|---|---|
| Grp 9 | Peptide 4094Kb = Peptide Immunogen UBITh3-εK-KKK-4094a (JXAI/MDOO1/NJ-a) SEQ ID No. 43 and PRRSV Th Pool 1 | 310 | 0.070 | <10 | 3.868 | 200 |
|  |  | 321 | 0.058 |  | 3.735 |  |
|  |  | 331 | 0.063 |  | 3.450 |  |

* Peptide immunogens 4020Kc, 4052Kb, 4124Kb, 4094Ka and 4094Kb were used in various challenge studies against AMERVAC-PRRS, PRRS MD001 and PRRS JXA1 strains as described in the respective examples.

TABLE 9

Effect of PRRSV Ectodomain M Peptide on GP5 B Epitope Cluster Peptide Antigens' Immunogenicity

| Grp 1 G.P. | Immunogen description | Animal No. | 0 wpi GP5.1/M Peptide ELISA $A_{450}$ @ 1:100 4020b | 0 wpi GP5.1/M Peptide ELISA $A_{450}$ @ 1:100 M | 0 wpi IFA Titer | 6 wpi GP5.1/M Peptide ELISA $\text{Log}_{10}$ Titer 4020b | 6 wpi GP5.1/M Peptide ELISA $\text{Log}_{10}$ Titer M | 6 wpi IFA Titer |
|---|---|---|---|---|---|---|---|---|
|  | 4020Kb (SEQ ID No. 37) | 4473 | 0.046 | 0.071 | NA | 3.755 | 0.000 | N/A |
|  |  | 4474 | 0.054 | 0.075 |  | 4.027 | 0.000 |  |
|  |  | 4475 | 0.069 | 0.080 |  | 4.746 | 0.000 |  |
| Grp 2 G.P. | Immunogen description | Animal No. | 0 wpi GP5.1/M Peptide ELISA $A_{450}$ @ 1:100 4020b | 0 wpi GP5.1/M Peptide ELISA $A_{450}$ @ 1:100 M | 0 wpi IFA Titer | 6 wpi GP5.1/M Peptide ELISA $\text{Log}_{10}$ Titer 4020b | 6 wpi GP5.1/M Peptide ELISA $\text{Log}_{10}$ Titer M | 6 wpi IFA Titer |
|  | 4020Kb (SEQ ID No. 37) + M (SEQ ID No. 93) at 1:1 ratio | 4464 | 0.071 | 0.087 | NA | 3.267 | 7.891 | NA |
|  |  | 4465 | 0.056 | 0.062 |  | 0.000 | 4.815 |  |
|  |  | 4466 | 0.053 | 0.075 |  | 1.728 | 6.672 |  |
| Grp 3 piglet | Immunogen description | Animal No. | 0 wpi GP5.2/M Peptide ELISA $A_{450}$ @ 1:100 4020c | 0 wpi GP5.2/M Peptide ELISA $A_{450}$ @ 1:100 M | 0 wpi IFA Titer | 6 wpi GP5.2/M Peptide ELISA $\text{Log}_{10}$ Titer 4020c | 6 wpi GP5.2/M Peptide ELISA $\text{Log}_{10}$ Titer M | 6 wpi IFA Titer |
|  | 4020Kc (SEQ ID No. 38) | F-1 | 0.146 | 0.270 | <10 | 3.831 | 1.051 | 100 |
|  |  | F-2 | 0.294 | 0.280 |  | 5.023 | 1.964 | 100 |
|  |  | F-3 | 0.111 | 0.196 |  | 4.754 | 1.032 | 200 |
| Grp 4 piglet | Immunogen description | Animal No. | 0 wpi GP5.2/M Peptide ELISA $A_{450}$ @ 1:100 4020c | 0 wpi GP5.2/M Peptide ELISA $A_{450}$ @ 1:100 M | 0 wpi IFA Titer | 6 wpi GP5.2/M Peptide ELISA $\text{Log}_{10}$ Titer 4020c | 6 wpi GP5.2/M Peptide ELISA $\text{Log}_{10}$ Titer M | 6 wpi IFA Titer |
|  | 4020Kc (SEQ ID No. 38) + M (SEQ ID No. 93) at 1:1 ratio | A-1 | 0.254 | 0.331 | <10 | 3.817 | 5.480 | <50 |
|  |  | A-2 | 0.298 | 0.333 |  | 4.584 | 5.699 | <50 |
|  |  | A-3 | 0.290 | 0.314 |  | 3.486 | 6.027 | <50 |
| Grp 5 piglet | Immunogen description | Animal No. | 0 wpi GP5.2/M Peptide ELISA $A_{450}$ @ 1:100 4020c | 0 wpi GP5.2/M Peptide ELISA $A_{450}$ @ 1:100 M | 0 wpi IFA Titer | 6 wpi GP5.2/M Peptide ELISA $\text{Log}_{10}$ Titer 4020c | 6 wpi GP5.2/M Peptide ELISA $\text{Log}_{10}$ Titer M | 6 wpi IFA Titer |
|  | 4020Kc (SEQ ID No. 38) + M (SEQ ID No. 93) at 10:1 ratio | E-1 | 0.250 | 0.069 | <10 | 4.115 | 2.282 | <50 |
|  |  | E-2 | 0.168 | 0.366 |  | 5.020 | 5.020 | 100 |
|  |  | E-3 | 0.280 | 0.304 |  | 3.109 | 3.109 | 50 |

TABLE 10

Effect of Varying Doses of PRRSV Th Pool 1 on the IFA titers of the PRRSV B Cell Epitope Cluster Peptide Antigen 4094a in Piglets

| | | | 0 wpi | | 6 wpi | |
|---|---|---|---|---|---|---|
| Immunogen description | | Animal No. | GP5.4 Peptide ELISA $A_{450}$@1:100 4094a | IFA Titer | GP5.4 Peptide ELISA ELISA $Log_{10}$ Titer 4094a | IFA Titer |
| Grp 1 | 4094a (SEQ ID No 34) + 5% PRRSV Th pool 1* | B124 | 0.020 | <10 | 3.845 | 50 |
| | | O23 | 0.010 | | 3.250 | 50 |
| | | O24 | 0.020 | | 2.950 | 100 |

| | | | 0 wpi | | 6 wpi | |
|---|---|---|---|---|---|---|
| Immunogen description | | Animal No. | GP5.4 Peptide ELISA $A_{450}$@1:100 4094a | IFA Titer | GP5.4 Peptide ELISA ELISA $Log_{10}$ Titer 4094a | IFA Titer |
| Grp 2 | 4094a + 10% PRRSV Th pool 1 | B125 | 0.040 | <10 | 3.207 | 100 |
| | | B113 | 0.040 | | 3.032 | 100 |
| | | B112 | 0.050 | | 3.397 | 50 |

| | | | 0 wpi | | 6 wpi | |
|---|---|---|---|---|---|---|
| Immunogen description | | Animal No. | GP5.4 Peptide ELISA $A_{450}$@1:100 4094a | IFA Titer | GP5.4 Peptide ELISA ELISA $Log_{10}$ Titer 4094a | IFA Titer |
| Grp 3 | 4094a + 20% PRRSV Th pool 1 | B115 | 0.005 | <10 | 3.924 | 100 |
| | | B116 | 0.030 | | 2.888 | 50 |
| | | O207 | 0.010 | | 2.777 | 200 |

| | | | 0 wpi | | 6 wpi | |
|---|---|---|---|---|---|---|
| Immunogen description | | Animal No. | GP5.4 Peptide ELISA $A_{450}$@1:100 4094a | IFA Titer | GP5.4 Peptide ELISA ELISA $Log_{10}$ Titer 4094a | IFA Titer |
| Grp 4 | 4094a + 50% PRRSV Th pool 1 | B118 | 0.010 | <10 | 3.236 | 200 |
| | | B119 | 0.040 | | 3.369 | 200 |
| | | B120 | 0.020 | | 2.005 | 200 |

| | | | 0 wpi | | 6 wpi | |
|---|---|---|---|---|---|---|
| Immunogen description | | Animal No. | GP5.4 Peptide ELISA $A_{450}$@1:100 4094a | IFA Titer | GP5.4 Peptide ELISA ELISA $Log_{10}$ Titer 4094a | IFA Titer |
| Grp 5 | Peptide 4094 Kb (SEQ ID No. 43) = UBITh3-εK-KKK-4094a (JXAI/MDOO1/NJ-a) | 310 | 0.010 | <10 | 3.868 | 200 |
| | | 321 | 0.070 | | 3.735 | 200 |
| | | 331 | 0.010 | | 3.450 | 200 |

*PRRSV Th pool 1 (SEQ ID Nos 47, 51, 52, 55, 59, 61, 63, 67, 70, 74, 76 at equal ratio)

TABLE 11

Immunogenicity of GP2, GP3 and GP4 B ell Cluster Peptide Antigens in Guinea Pigs after Single Adminsitration

| | | | 0 wpi | | 3 wpi | |
|---|---|---|---|---|---|---|
| Immunogen description | | Animal No. | SEQ ID No. 10 $A_{450}$@1:100 | IFA Titer | SEQ ID No. 10 ELISA $Log_{10}$ Titer | IFA Titer |
| Grp 1 | GP2 B epitope (V111-L136) SEQ ID No. 10 | 4955 | 0.048 | <10 | 0.000 | <10 |
| | | 4956 | 0.049 | | 0.000 | |
| | | 4957 | 0.054 | | 0.000 | |

TABLE 11-continued

Immunogenicity of GP2, GP3 and GP4 B ell Cluster Peptide Antigens in Guinea Pigs after Single Adminsitration

| Immunogen description | Animal No. | 0 wpi SEQ ID No. 10 $A_{450}$@1:100 | IFA Titer | 3 wpi SEQ ID No. 10 ELISA $Log_{10}$ Titer | IFA Titer |
|---|---|---|---|---|---|
| Grp 2 UBITh-εK-GP2 B epitope (V111-L136) SEQ ID No. 44 | 4958 | 0.059 | <10 | 2.945 | 80 |
| | 4959 | 0.056 | | 4.350 | |
| | 4960 | 0.052 | | 3.650 | |

| Immunogen description | Animal No. | 0 wpi SEQ ID No. 11 $A_{450}$@1:100 | IFA Titer | 3 wpi SEQ ID No. 11 ELISA $Log_{10}$ Titer | IFA Titer |
|---|---|---|---|---|---|
| Grp 3 GP3 B epitope (C57-C75) SEQ ID No. 11 | 4969 | 0.048 | <10 | 0.000 | <10 |
| | 4970 | 0.047 | | 0.000 | |
| | 4971 | 0.044 | | 0.000 | |

| Immunogen description | Animal No. | 0 wpi SEQ ID No. 11 $A_{450}$@1:100 | IFA Titer | 3 wpi SEQ ID No. 11 ELISA $Log_{10}$ Titer | IFA Titer |
|---|---|---|---|---|---|
| Grp 4 UBITh-εK-GP3 B epitope (C57-C75) SEQ ID No. 45 | 4962 | 0.059 | <10 | 4.222 | 80 |
| | 4963 | 0.056 | | 3.888 | |
| | 4964 | 0.052 | | 4.285 | |

| Immunogen description | Animal No. | 0 wpi SEQ ID No. 12 $A_{450}$@1:100 | IFA Titer | 3 wpi SEQ ID No. 12 ELISA $Log_{10}$ Titer | IFA Titer |
|---|---|---|---|---|---|
| Grp 5 GP4 B epitope (C52-C69) SEQ ID No. 12 | 4972 | 0.046 | <10 | 0.000 | <10 |
| | 4973 | 0.046 | | 0.000 | |
| | 4974 | 0.044 | | 0.000 | |

| Immunogen description | Animal No. | 0 wpi SEQ ID No. 12 $A_{450}$@1:100 | IFA Titer | 3 wpi SEQ ID No. 12 ELISA $Log_{10}$ Titer | IFA Titer |
|---|---|---|---|---|---|
| Grp 6 UBITh-εK-GP4 B epitope (C52-C69) SEQ ID No. 46 | 4966 | 0.053 | <10 | 4.561 | 80 |
| | 4967 | 0.053 | | 4.830 | |
| | 4968 | 0.056 | | 4.695 | |

TABLE 12

Immunogenicity Assessment for PRRSV GP5.3, GP2, GP3 and GP4 Antigenic Peptides in Guinea Pigs by target peptide based ELISAs and IFA

| | | | 0 wpi | | | | 5 wpi | | | | |
|---|---|---|---|---|---|---|---|---|---|---|---|
| | | PRRSV Peptide ELISA $A_{450}$@1:100 | | | | | PRRSV Peptide ELISA $Log_{10}$ Titer | | | | |
| Grp # Immunogen description | Animal No. | GP2 (SEQ ID No. 10) | GP3 (SEQ ID No. 11) | GP4 (SEQ ID No. 12) | GP5.3 (SEQ ID No. 33) | IFA Titer | GP2 | GP3 | GP4 | GP5.3 | IFA Titer |
| 1 PRRSV GP4 Peptide Immunogen (SEQ ID No. 46) | 4926 | 0.047 | 0.048 | 0.048 | 0.049 | <10 | <1 | <1 | 4.598 | <1 | 80 |
| | 4927 | 0.047 | 0.050 | 0.050 | 0.050 | | <1 | <1 | 3.791 | <1 | |
| 2 PRRSV GP3/4 Peptide Immunogens (SEQ ID No. 45 and 46) | 4916 | 0.050 | 0.048 | 0.051 | 0.053 | <10 | <1 | 4.585 | 4.656 | <1 | 160 |
| | 4917 | 0.049 | 0.049 | 0.049 | 0.051 | | <1 | 5.087 | 4.811 | <1 | |
| 3 PRRSV GP3/4/5 Peptide Immunogens (SEQ ID No. 45, 46 and 42) | 4910 | 0.005 | 0.047 | 0.047 | 0.049 | <10 | <1 | 3.661 | 2.349 | 4.608 | 160 |
| | 4911 | 0.046 | 0.048 | 0.048 | 0.050 | | <1 | 4.741 | 3.662 | 4.276 | |
| 4 PRRSV GP2/3/4 Peptide Immunogens (SEQ ID No. 44, 45 and 46) | 4922 | 0.047 | 0.049 | 0.048 | 0.052 | <10 | 4.207 | 4.289 | 3.147 | <1 | 160 |
| | 4923 | 0.052 | 0.050 | 0.053 | 0.052 | | 4.181 | 4.787 | 3.556 | <1 | |

TABLE 13

Animal study schedule

| Practice | Performance time (WPI) (weeks post initial immunization) |
|---|---|
| Grouping, Ear tagging, Blood sampling | W0 |
| Vaccine administration: Intramuscular injection was placed at a site which is located directly behind the ear on the side of the pig's neck muscle. | |
| Blood sampling | W4 |
| Boost | |
| Blood sampling | W6 |
| Animals moved out into challenge site | W7 |
| Challenge study by intra-nasal administration 10 doses AMERVAC®-PRRS ($10^{6.8}$ TCID$_{50}$/head) or PRRS MD-001 ($10^5$ TCID$_{50}$/head) | W7 |
| Blood sampling | W9, End of the challenge study |

TABLE 14

Summary results of PRRSV challenge studies

| Group # | # of Animals/ group | Shot No. | IFA titer at 4 wpi | IFA titer at 6 wpi | IFA titer at 2 wpc[2] | Lung lesion score at 2 wpc[3] |
|---|---|---|---|---|---|---|
| 1[1] | 5 | 2 | 50 | 100 | | 0 |
| | | | <50 | 100 | | 0 |
| | | | 50 | 100 | | 0 |
| | | | 100 | 200 | | 0 |
| | | | 100 | 100 | | 0 |
| 2[1] | 5 | 2 | 50 | 50 | 50 | 0 |
| | | | <50 | 50 | 50 | 0 |
| | | | <50 | <50 | 50 | 0 |
| | | | 50 | 50 | 50 | 0 |
| | | | 100 | 50 | 50 | 0 |
| 3[1] | 5 | 2 | <50 | | <50 | 1 |
| | | | 50 | | 50 | 0 |
| | | | <50 | | <50 | 0 |
| | | | 50 | | 100 | 0 |
| | | | 50 | | 100 | 0 |
| 4[1] | 5 | 2 | 50 | | 100 | 0 |
| | | | <50 | | <50 | 1 |
| | | | 100 | | 200 | 0 |
| | | | 50 | | 50 | 0 |
| | | | 200 | | 200 | 0 |
| Control[1] | 5 | 0 | <50 | | <50 | 3 |
| | | | <50 | | <50 | 3 |
| | | | <50 | | <50 | 0 |
| | | | <50 | | <50 | 3 |
| | | | <50 | | <50 | 3 |

[1] Data from group 1 (PRRS-10-01S), group 2 (PRRS-10-02S), groups 3 & 4 (PRRS-10-03S), and Control group (PRRS-10-02S).
[2] AMERVAC-PRRS strain challenge: group 1; MD-001 strain challenge: groups 2, 3 and 4.
[3] Lesion score: 0, no lesion; 1, slight lesion; 2, mild lesion; 3, severe lesion.

TABLE 15

Animal Group and Dosage

| Group | Vaccine Formulation | Number of Animals/Group | Volume of Vaccine | Number of Innoculations |
|---|---|---|---|---|
| 1 | Formula 1 | 5 | 1 ml | 2 |
| 2 | Formula 2 | 5 | 1 ml | 2 |
| 3 | Formula 3 | 5 | 1 ml | 2 |
| 4 | Formula 4 | 5 | 1 ml | 2 |
| 5 | Formula 5 | 5 | 1 ml | 1 |
| 6 | Formula 6 | 5 | 0 | 0 |

Note:
No immunization for control group 6;
immunization at 0 wpi only for group 5
two immunizations for groups 1-4 at 0 wpi and 2 wpi.
All dosage formulations for immunization are the same (1 mL).
1.2.4 Immunogenicity: Test the PRRS antigen ata 4 wpi (day 28) before viral challenges
1.2.5 Viral challenge: use PRRS virulent strain (NVCD-JXA1) after 4 wpi (day 28)
1.2.6 Measure body temperature: each day from the 21$^{st}$ day after viral innoculation

TABLE 16

Result of PRRSV ELISA OD$_{450\,nm}$
Prior to Immunization

| | | | | | Pos Con | Neg Con |
|---|---|---|---|---|---|---|
| 0.264 | 0.122 | 0.094 | 0.160 | 0.200 | | |
| 0.249 | 0.210 | 0.087 | 0.245 | 0.193 | 2.182 | 0.233 |
| 0.241 | 0.262 | 0.094 | 0.164 | 0.174 | 2.179 | 0.302 |
| 0.292 | 0.222 | 0.141 | 0.191 | | | |
| 0.225 | 0.112 | 0.195 | 0.205 | | | |
| 0.350 | 0.095 | 0.226 | 0.202 | | | |
| 0..213 | 0.137 | 0.219 | 0.188 | | | |

Note:
The above are average OD values by testing animal samples with PRRSV ELISA. Both positive and negative controls are provided by the ELISA kit. According to the assay kit, the positive and negative values are considered valid if "positive average value"/"negative average value" = S/N >4.0.
The tested results showed that all samples are negative for PRRS antibody (OD) prior to the immunization.

TABLE 17

Animal Number and Groups

| Group 1 | Group 2 | Group 3 | Group 4 | Group 5 | Group 6 |
|---|---|---|---|---|---|
| 7 | 16 | 2 | 4 | 1 | 13 |
| 14 | 17 | 8 | 5 | 10 | 20 |
| 50 | 21 | 51 | 9 | 12 | 25 |
| 27 | 54 | 55 | 11 | 15 | 26 |
| 30 | 28 | 57 | 32 | 49 | 31 |

TABLE 18

Result of PRRS Antibody Reactivity (OD)
4 week post-immunization

| Pig No. | 1 | 2 | 4 | 5 | 7 | 8 | 9 | 10 | 11 | 12 | 13 | 14 |
|---|---|---|---|---|---|---|---|---|---|---|---|---|
| 2wpi | 0.574 | 0.862 | 0.736 | 0.562 | 0.479 | 0.457 | 0.347 | 0.305 | 0.611 | 0.487 | 0.816 | 1.911 |
| 4wpi | 0.926 | 0.557 | 0.595 | 0.476 | 1.377 | 2.377 | 0.564 | 0.670 | 2.187 | 0.129 | 0.530 | 0.515 |

| Pig No. | 15 | 16 | 17 | 20 | 21 | 25 | 26 | 27 | 28 | 30 | 31 | 32 |
|---|---|---|---|---|---|---|---|---|---|---|---|---|
| 2wpi | 0.686 | 0.68 | 1.101 | 0.482 | 0.172 | 0.367 | 0.307 | 0.286 | 0.549 | 0.345 | 0.306 | 0.667 |
| 4wpi | 0.549 | 0.876 | 0.243 | 0.584 | 0.334 | 0.284 | 0.575 | 0.684 | 0.338 | 0.364 | 0.306 | 0.328 |

| Pig No. | 49 | 50 | 51 | 54 | 55 | 57 |
|---|---|---|---|---|---|---|
| 2wpi | 1.254 | 0.309 | 0.960 | 0.522 | 2.361 | 0.462 |
| 4wpi | 1.736 | 0.602 | 3.094 | 0.542 | 1.198 | 1.310 |
| Pos | 2.764 | 2.740 | | | | |
| Con | 0.283 | 0.253 | | | | |

Note:
OD >0.4995 is scored as positive

TABLE 19

Body Temperature Observations and Mortality (X) after Challenge

| | | Temp C.° | | | | | | | | | | |
|---|---|---|---|---|---|---|---|---|---|---|---|---|
| GP | Pig No. | 04-03 | 04-04 | 04-05 | 04-06 | 04-07 | 04-08 | 04-09 | 04-10 | 04-11 | 04-12 | 04-13 |
| 1 | 7 | 39.8 | 39.4 | 39.9 | 40.3 | 40.5 | 41.2 | 41.6 | 41.5 | 41.3 | 41.2 | 40.2 |
| | 14 | 40.6 | 40.3 | 41.2 | 41.2 | 41.0 | 40.6 | 40.6 | 41.1 | 41.2 | 41.0 | 40.8 |
| | 50 | 39.8 | 40.3 | 40.7 | 41.2 | 40.0 | 40.4 | 41.2 | 40.8 | 41.2 | 41.2 | 40.8 |
| | 27 | 39.2 | 39.8 | 40.0 | 40.0 | 40.0 | 40.7 | 40.6 | 41.0 | 41.5 | 41.3 | 40.5 |
| | 30 | 39.0 | 40.2 | 41.0 | 41.5 | 40.0 | 40.8 | 40.8 | 40.7 | 40.9 | 41.0 | 40.2 |
| 2 | 16 | 39.9 | 39.3 | 41.2 | 41.3 | 40.5 | 41.5 | 41.4 | 41.0 | 41.6 | 41.8 | 40.7 |
| | 17 | 40.3 | 40.0 | 40.5 | 41.3 | 40.4 | 41.2 | 40.8 | 41.0 | 41.2 | 41.7 | 41.0 |
| | 21 | 38.8 | 40.7 | 40.8 | 39.5 | 39.7 | 39.9 | 39.8 | 40.0 | 40.9 | 41.2 | 40.0 |
| | 54 | 39.6 | 40.3 | 41.1 | 41.6 | 39.7 | 40.7 | 41.2 | 41.0 | 41.0 | 41.0 | 40.5 |
| | 28 | 39.9 | 40.2 | 40.6 | 40.3 | 40.0 | 41.0 | 41.2 | 40.8 | 41.2 | 40.7 | 40.3 |
| 3 | 2 | 39.1 | 39.5 | 40.1 | 40.0 | 40.3 | 40.6 | 40.7 | 41.3 | 41.1 | 41.0 | 41.0 |
| | 8 | 39.5 | 39.5 | 40.0 | 40.2 | 40.5 | 40.3 | 40.6 | 40.7 | 41.0 | 40.5 | 40.0 |
| | 51 | 40.3 | 40.6 | 41.5 | 40.8 | 41.0 | 40.7 | 41.7 | 41.0 | 40.2 | 40.8 | 40.5 |
| | 55 | 39.4 | 40.3 | 41.2 | 40.1 | 39.8 | 41.2 | 41.0 | 41.0 | 40.9 | 41.2 | 40.7 |
| | 57 | 39.2 | 40.0 | 39.7 | 39.9 | 40.2 | 40.3 | 40.2 | 40.5 | 41.0 | 41.1 | 40.3 |
| 4 | 4 | 39.5 | 39.4 | 39.8 | 40.6 | 41.2 | 41.2 | 40.9 | 40.8 | 41.6 | 40.8 | 40.6 |
| | 5 | 40.5 | 40.0 | 40.7 | 41.0 | 40.5 | 41.3 | 40.6 | 40.7 | 41.0 | 40.8 | 40.4 |
| | 9 | 39.0 | 41.5 | 41.0 | 41.0 | 40.8 | 40.5 | 40.3 | 41.0 | 41.0 | 40.8 | 40.6 |
| | 11 | 39.0 | 40.1 | 40.0 | 39.9 | 40.2 | 39.8 | 40.3 | 40.5 | 40.8 | 41.0 | 40.6 |
| | 32 | 40.0 | 40.3 | 40.4 | 40.5 | 41.2 | 40.5 | 40.4 | 41.5 | 41.5 | 41.3 | 41.0 |
| 5 | 1 | 39.0 | 40.0 | 40.2 | 40.3 | 40.4 | 40.8 | 40.8 | 41.6 | 42.0 | 41.5 | 40.6 |
| | 10 | 39.6 | 39.8 | 39.8 | 40.1 | 40.8 | 40.7 | 40.3 | 41.2 | 41.0 | 41.0 | 40.8 |
| | 12 | 39.8 | 40.4 | 41.5 | 41.3 | 41.3 | 41.3 | 41.0 | 41.2 | 40.8 | 41.0 | 40.8 |
| | 15 | 39.8 | 40.2 | 41.2 | 41.3 | 40.5 | 40.8 | 40.3 | 41.0 | 41.5 | 41.0 | 42.0 |
| | 49 | 39.5 | 40.4 | 40.3 | 40.2 | 40.3 | 40.3 | 40.8 | 40.7 | 40.9 | 41.0 | 40.5 |
| 6 | 13 | 39.7 | 40.0 | 41.0 | 41.5 | 41.0 | 40.6 | 40.7 | 41.3 | 41.4 | 41.3 | 40.8 |
| | 20 | 39.5 | 40.7 | 41.2 | 40.2 | 40.1 | 40.0 | 40.7 | 41.2 | 41.8 | 42.0 | 41.3 |
| | 25 | 39.9 | 40.3 | 40.0 | 40.2 | 39.9 | 40.8 | 40.2 | 41.2 | x | | |
| | 26 | 39.4 | 39.7 | 40.3 | 40.3 | 39.9 | 40.3 | 40.3 | 40.5 | 41.0 | 41.3 | 41.1 |
| | 31 | 39.4 | 39.7 | 41.0 | 40.5 | 41.2 | 41.3 | 41.5 | 41.3 | 40.9 | x | |

TABLE 19-continued

Body Temperature Observations and Mortality (X) after Challenge

| GP | Pig No. | 04-14 | 04-15 | 04-16 | 04-17 | 04-18 | 04-19 | 04-20 | 04-21 | 04-22 | 04-23 | 04-24 |
|---|---|---|---|---|---|---|---|---|---|---|---|---|
| 1 | 7 | 40.3 | 40.2 | 40.2 | 40.2 | 40.5 | 39.7 | 39.5 | 39.3 | 39.6 | 39.5 | 39.6 |
|   | 14 | 40.8 | 40.7 | 40.5 | 40.2 | 40.2 | 40.2 | 40.7 | 40.4 | x | | |
|   | 50 | 40.0 | 40.2 | 39.9 | 39.8 | 40.2 | 40.5 | 39.2 | 39.5 | 39.7 | 39.5 | 39.4 |
|   | 27 | 40.7 | 40.6 | 40.3 | 40.7 | 40.2 | 40.3 | 39.6 | 39.9 | 39.8 | 39.6 | 39.6 |
|   | 30 | 40.0 | 40.0 | 40.3 | 41.0 | 40.6 | 40.6 | 40.3 | 39.4 | 39.8 | 39.7 | 39.4 |
| 2 | 16 | 40.6 | 40.5 | 40.2 | 39.8 | 39.8 | 39.6 | 39.8 | 39.4 | 39.2 | 39.6 | 39.5 |
|   | 17 | 40.6 | 41.1 | 39.8 | 40.5 | 39.0 | 39.4 | 39.2 | 39.2 | 39.5 | 39.2 | 39.3 |
|   | 21 | 39.8 | 39.8 | 39.3 | 39.5 | 39.7 | 39.2 | 40.5 | 39.9 | 40.1 | 39.9 | 39.7 |
|   | 54 | 40.2 | 40.7 | 40.2 | 39.8 | 39.5 | 39.7 | 39.2 | 39.7 | 39.8 | 39.7 | 39.6 |
|   | 28 | 40.4 | 40.7 | 40.3 | 40.2 | 40.2 | 40.2 | 40.2 | 40.0 | 40.0 | 39.9 | 39.9 |
| 3 | 2 | 40.5 | 40.3 | 40.9 | 40.8 | 40.5 | 39.9 | 39.8 | 39.7 | 39.5 | 39.2 | 39.5 |
|   | 8 | 40.8 | 40.6 | 40.0 | 40.2 | 40.4 | 40.6 | 39.7 | 39.7 | 39.5 | 39.3 | 39.5 |
|   | 51 | 40.8 | 40.7 | 40.4 | 40.4 | 39.9 | 40.7 | 40.4 | 39.7 | 39.2 | 39.6 | 39.4 |
|   | 55 | 40.2 | 40.9 | 41.0 | 40.6 | 40.5 | 40.5 | 40.4 | 40.1 | 40.2 | 40.0 | 39.9 |
|   | 57 | 40.5 | 40.4 | 40.3 | 40.2 | 39.9 | 40.2 | 40.5 | 40.1 | 40.0 | 40.2 | 40.1 |
| 4 | 4 | 40.4 | 39.9 | 40.2 | 40.1 | 41.2 | 40.5 | 40.1 | 39.9 | 39.8 | 39.7 | 39.8 |
|   | 5 | 40.7 | 40.3 | 40.0 | 40.0 | 40.7 | 40.0 | 39.6 | 39.4 | 39.2 | 39.3 | 39.5 |
|   | 9 | 40.0 | 39.5 | 39.0 | 39.4 | 40.2 | 39.5 | 39.6 | 39.4 | 39.2 | 39.4 | 39.2 |
|   | 11 | 40.3 | 40.0 | 40.3 | 39.7 | 39.5 | 40.2 | 39.2 | 39.3 | 39.5 | 39.2 | 39.5 |
|   | 32 | 41.0 | 39.8 | 40.0 | 40.5 | 40.4 | 39.6 | 39.5 | 39.4 | 39.6 | 39.4 | 39.7 |
| 5 | 1 | 41.0 | 40.7 | 39.7 | 40.0 | 39.7 | 39.5 | 39.2 | 39.3 | 39.7 | 39.6 | 39.4 |
|   | 10 | 40.7 | 40.5 | 40.3 | 39.9 | 40.6 | 40.3 | 39.8 | 39.6 | 39.4 | 39.3 | 39.2 |
|   | 12 | 40.5 | 39.9 | 40.4 | 40.7 | 40.6 | 39.7 | 39.7 | 39.9 | 39.5 | 39.3 | 39.2 |
|   | 15 | 40.6 | 41.2 | 39.8 | 40.2 | 39.7 | 39.5 | 39.7 | 39.6 | 39.9 | 39.8 | 39.6 |
|   | 49 | 40.3 | 40.3 | 39.8 | 39.8 | 40.2 | 39.8 | 39.3 | 39.4 | 39.5 | 39.3 | 39.4 |
| 6 | 13 | 41.2 | 41.3 | 40.7 | 41.2 | 40.7 | 41.2 | 40.5 | 40.3 | 40.2 | 40.0 | 39.8 |
|   | 20 | 40.8 | 40.7 | 40.4 | 40.2 | 39.8 | 39.5 | 39.2 | 39.1 | 39.0 | 40.2 | 40.0 |
|   | 25 | | | | | | | | | | | |
|   | 26 | 40.5 | 40.5 | 40.2 | 40.2 | 40.2 | 39.8 | 39.5 | 39.3 | 39.6 | 39.7 | 39.4 |
|   | 31 | | | | | | | | | | | |

TABLE 20

Results of PRRS Viral challenge Test

| Group No. | Number of Animals | Number dead | Mortality Rate |
|---|---|---|---|
| 1 | 5 | 1 | 20% |
| 2 | 5 | 0 | 0% |
| 3 | 5 | 0 | 0% |
| 4 | 5 | 0 | 0% |
| 5 | 5 | 0 | 0% |
| 6 | 5 | 2 | 40% |

For groups 1 to 5 combined, 24 out of 25 pigs survived the PRRSV JAX1 challenge with a 4% mortality rate. In the control group 6, 2 out of 5 pigs died during early days of the challenge study with a mortality rate of 40%. In the control group 6, all animals became sick, i.e. a morbidity rate of 100%. The challenge study was considered valid based on the PRC Ministry of Agriculture guidelines.

TABLE 21

| | Sample Size Requirement PRRS prevalence rate in the herd | |
|---|---|---|
| Number of pigs raised in a farm | 10% | 5% |
| <100 | 25 | 45 |
| 200 | 27 | 51 |
| 300 | 28 | 54 |
| 400 | 28 | 55 |
| 500 | 28 | 56 |
| 1000 | 29 | 57 |
| ≥5000 | 29 | 59 |

1. Farms operated according to SOP, sow and regular pigs should be separated into two groups for blood collection.
2. Random sampling method is based on probability calculation.

TABLE 22

Clearance of PRRSV infection in piglets by immunizations (0, 4, 8 wpi) with PRRSV peptide immunogen based vaccine formulations

| | | O.D 450 value/Cut-Off value(C.O = 0.15) | | | | | |
|---|---|---|---|---|---|---|---|
| Group | Animals ID No. | 0 wpi Bleed | 4 wpi Bleed | 6 wpi Bleed | 8 wpi Bleed | 10 wpi Bleed | 13 wpi Bleed |
| 1 | 317 | 2.93 | 4.92 | 6.51 | 3.07 | 0.23 | 0.38 |
|   | 312 | 5.75 | 1.05 | 3.49 | 4.42 | 0.12 | −0.03 |
|   | 309 | 2.73 | 2.65 | 3.35 | 1.53 | −0.1 | 0.08 |
| 2 | 331 | 1.89 | 6.91 | 10.57 | 8.75 | 2.38 | 0.81 |
|   | 336 | 7.79 | 1.29 | 0.72 | 0.04 | −0.05 | −0.08 |
|   | 341 | 1.77 | 1.79 | 7.04 | 2.31 | −0.04 | −0.08 |
| 3 | 339 | 2.53 | 3.18 | 6.42 | 3.81 | 0.39 | 0.09 |
|   | 343 | 3.28 | 5.91 | 12.2 | 3.84 | 0.78 | 0.55 |
|   | 345 | 3.92 | 6.52 | 9.76 | 7.19 | 0.58 | 0.35 |
| 4 | 340 | 2.02 | 4.18 | 10.78 | 4.39 | −0.01 | 0.62 |
|   | 342 | 2.44 | 3.93 | 6.26 | 8.21 | 0.13 | 0.16 |
|   | 344 | 2.27 | 5.55 | 10.29 | 7.63 | 0.74 | 0.16 |
| 5 | 306 | 15.49 | 12.74 | 10.12 | 13.54 | 9.34 | 15.45 |
|   | 314 | 7.81 | 5.3 | 10.64 | 15.93 | 16.56 | 18.38 |
|   | 322 | 2.23 | 2.39 | 10.45 | 10.38 | 17.2 | 11.93 |

Piglets at 4 weeks of age were immunized three times at 0, 4 and 8 weeks post initial immunization.
If S/C.O. ≥1, the sample is classified as POSITIVE for PRSSV antibodies.
If S/C.O. <1, the sample is classified as NEGATIVE for PRSSV antibodies.
S: O.D450 value of sample
C.O.: cut-off value

The invention claimed is:

1. A Porcine Reproductive and Respiratory Syndrome (PRRS) vaccine composition, comprising a peptide antigen and a veterinarily acceptable delivery vehicle or adjuvant, wherein the peptide antigen is:
   a GP5.3B cell epitope cluster amino acid sequence represented by SEQ ID NOs: 9, 13, 14, 15, 16, 31, 32, or 33
   covalently linked, with or without a spacer, to a foreign T helper epitope.

2. The PRRS vaccine according to claim 1, wherein the GP5.3B cell epitope cluster amino acid sequence is SEQ ID NO: 9.

3. The PRRS vaccine according to claim 1, wherein the GP5.3B cell epitope cluster amino acid sequence is selected from the group consisting of SEQ ID NOs: 13, 14, 15, 16, 31, 32, and 33.

4. The PRRS vaccine according to claim 1, wherein the composition further comprises an additional peptide antigen selected from the group consisting of:
   i) an amino acid sequence comprising a GP2 B cell epitope cluster represented by SEQ ID NOs: 10, 17, 18, 19, or 20;
   ii) an amino acid sequence comprising a GP3 B cell epitope cluster represented by SEQ ID NOs: 11, 21, 22, 23, or 24;
   iii) an amino acid sequence comprising a GP4 B cell epitope cluster represented by SEQ ID NOs: 12, 25, 26, 27, or 28; and
   iv) any combination of (i), (ii), and/or (iii).

5. The PRRS vaccine according to claim 4, wherein the additional peptide antigen is an amino acid sequence represented by SEQ ID NOs: 44, 45, 46, or any combination thereof.

6. The PRRS vaccine according to claim 1, wherein the composition comprises more than one peptide antigen.

7. The PRRS vaccine according to claim 1, wherein the foreign T helper epitope is covalently linked to the amino- or carboxyl-terminus of the peptide antigen through a spacer.

8. The PRRS vaccine according to claim 7, wherein the foreign T helper epitope is SEQ ID NO: 35.

9. The PRRS vaccine according to claim 7, wherein the foreign T helper epitope is covalently linked to the peptide antigen through a spacer comprising an epsilon lysine residue.

10. The PRRS vaccine according to claim 9, wherein the spacer is SEQ ID NO: 36.

11. The PRRS vaccine according to claim 1, further comprising a PRRS T helper epitope that is unlinked to the peptide antigen, wherein the PRRS T helper epitope is selected from the group consisting of SEQ ID NOs: 47-90 and any combination thereof.

12. The PRRS vaccine according to any of claim 1, wherein the total amount of peptide antigen is between about 10 µg to about 1 mg.

13. The PRRS vaccine according to claim 1, wherein the delivery vehicle or adjuvant is selected from a group consisting of an oil vaccine adjuvant composition comprised of vegetable oil and mannide oleate for production of water-in-oil emulsions, Polyoxyethylene (20) sorbitan monooleate, and a CpG oligonucleotide.

14. A method for protecting a piglet against PRRS infection, comprising administering the PRRS vaccine according to claim 1 to the piglet.

15. A PRRS vaccine composition, comprising
   a) a peptide antigen consisting of:
      i) a GP5.3B cell epitope cluster amino acid sequence represented by SEQ ID NOs: 9, 13, 14, 15, 16, 31, 32, or 33
      covalently linked, with or without a spacer, to a foreign T helper epitope;
   b) an additional peptide antigen selected from the group consisting of:
      i) an amino acid sequence comprising a GP2B cell epitope cluster represented by SEQ ID NOs: 10, 17, 18, 19, or 20;
      ii) an amino acid sequence comprising a GP3 B cell epitope cluster represented by SEQ ID NOs: 11, 21, 22, 23, or 24;
      iii) an amino acid sequence comprising a GP4 B cell epitope cluster represented by SEQ ID NOs: 12, 25, 26, 27, or 28; and
      iv) any combination of (i), (ii), and/or (iii);
   c) a PRRS T helper epitope selected from the group consisting of SEQ ID NOs: 47-90 and any combination thereof; and
   d) a veterinarily acceptable delivery vehicle or adjuvant.

16. The PRRS vaccine composition according to claim 15, wherein the additional peptide of (b) is an amino acid sequence represented by SEQ ID NOs: 44, 45, 46, or any combination thereof.

17. A method for protecting a piglet against PRRS infection, comprising administering the PRRS vaccine according to claim 15 to the piglet.

18. A method for protecting a piglet against PRRS infection, comprising administering the PRRS vaccine according to claim 16 to the piglet.

* * * * *